US012716075B2

(12) United States Patent
Hellal et al.

(10) Patent No.: US 12,716,075 B2
(45) Date of Patent: Aug. 25, 2026

(54) COMPOSITIONS FOR TRANSFECTING A NUCLEIC ACID MOLECULE INTO A CELL COMPRISING BENZO-FUSED HETEROCYCLIC COMPOUNDS GRAFTED TO A CATIONIC POLYMER, AND THEIR APPLICATIONS

(71) Applicant: POLYPLUS TRANSFECTION, Illkirch-Graffenstaden (FR)

(72) Inventors: Malik Hellal, Illkirch-Gaffenstaden (FR); Fabrice Stock, Benfeld (FR); Patrick Erbacher, Benfeld (FR); Yann Philipson, Brumath (FR); Mégane Denu, Illkrich-Graffenstaden (FR); Marine Ricordel, Dambach la Ville (FR); Fanny Premartin, Illkirch-Graffenstaden (FR); Thibaut Benchimol, Erstein (FR); Mathieu Porte, Lingolsheim (FR); Valérie Toussaint Moreau, Illkirch-Graffenstaden (FR); Jonathan Havard, Illkirch-Graffenstaden (FR)

(73) Assignee: SARTORIUS POLYPLUS, Illkirch-Graffenstaden (FR)

( * ) Notice: Subject to any disclaimer, the term of this patent is extended or adjusted under 35 U.S.C. 154(b) by 1189 days.

(21) Appl. No.: 17/632,921

(22) PCT Filed: Aug. 5, 2020

(86) PCT No.: PCT/EP2020/072065
§ 371 (c)(1),
(2) Date: Feb. 4, 2022

(87) PCT Pub. No.: WO2021/023796
PCT Pub. Date: Feb. 11, 2021

(65) Prior Publication Data

US 2022/0325299 A1 Oct. 13, 2022

(30) Foreign Application Priority Data

Aug. 5, 2019 (EP) .................................... 19315083

(51) Int. Cl.
*C12N 15/87* (2006.01)
*A61K 47/59* (2017.01)
(Continued)

(52) U.S. Cl.
CPC .............. *C12N 15/87* (2013.01); *A61K 47/59* (2017.08); *C08G 73/02* (2013.01);
(Continued)

(58) Field of Classification Search
CPC .................... C12N 15/87; C12N 15/86; C12N 2740/15051; C12N 2740/16043;
(Continued)

(56) References Cited

U.S. PATENT DOCUMENTS

| | | | |
|---|---|---|---|
| 8,658,150 | B2 | 2/2014 | Cheradame et al. |
| 2011/0091407 | A1 | 4/2011 | Cheradame |

(Continued)

FOREIGN PATENT DOCUMENTS

| | | | |
|---|---|---|---|
| CN | 1290178 | A | 4/2001 |
| CN | 1665544 | A | 9/2005 |

(Continued)

OTHER PUBLICATIONS

Wundt, E. Derivatives of Phenylenediamines. Ph.D. Dissertation, p. 15, Kiel University, Kiel, Germany, 1878. (Year: 1878).*

Pangon, A. et al. Polyethyleneimine Containing Benzimidazole Branching: A Model System Providing a Balance of Hydrogen Bond Network or Chain Mobility Enhances Proton Conductivity. J. Phys. Chem. B 2011, 115, 11359-11367. (Year: 2011).*

Smith, L. I. et al. Studies on the Polymethylbenzenes. XI. The Nitration of Pentamethylbenzene and of Hexamethyl- and Hexaethylbenzene. J. Am. Chem. Soc. 1935, 57, 1289-1292. (Year: 1935).*

McKim, et al. Dimethyl Sulfoxide USP, PhEur in Approved Pharmaceutical Products and Medical Devices. Pharmaceutical Technology 2008, 32. (Year: 2008).*

(Continued)

*Primary Examiner* — Jeffrey H Murray
*Assistant Examiner* — Kristen W Romero
(74) *Attorney, Agent, or Firm* — NIXON & VANDERHYE

(57) ABSTRACT

Compositions for transfecting a nucleic acid molecule into a cell are described. Each composition includes at least one benzimidazole or benzotriazole compound of general formula (II):

(II)

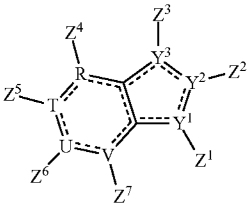

in which the benzimidazole or benzotriazole ring is substituted at a ring nitrogen by a graft cationic polymer $P^+$ that is a linear or branched polyethyleneimine (PEI) via a $—CH_2—(CH_2)_m—CO—$ linker, where m is 1-3. The remaining ring positions can be unsubstituted or substituted by alkyl, alkoxy, aryl, or related groups. The compositions can further include a nucleic acid molecule together with an acceptable excipient, buffering agent, cell culture medium, or transfection medium, and are useful for in vitro or ex vivo gene delivery with high transfection efficiency and reduced cytotoxicity.

41 Claims, 8 Drawing Sheets

(51) Int. Cl.
*C08G 73/02* (2006.01)
*C12N 15/86* (2006.01)

(52) U.S. Cl.
CPC ......... *C08G 73/0206* (2013.01); *C12N 15/86* (2013.01); *C12N 2740/15051* (2013.01); *C12N 2740/16043* (2013.01); *C12N 2740/16051* (2013.01); *C12N 2750/14143* (2013.01); *C12N 2750/14151* (2013.01)

(58) Field of Classification Search
CPC ........... C12N 2740/16051; C12N 2750/14143; C12N 2750/14151; A61K 47/59; C08G 73/02; C08G 73/0206
See application file for complete search history.

(56) References Cited

U.S. PATENT DOCUMENTS

| | | | |
|---|---|---|---|
| 2014/0323556 | A1 | 10/2014 | Qu |
| 2018/0002347 | A1 | 1/2018 | Yonemura et al. |

FOREIGN PATENT DOCUMENTS

| | | | | |
|---|---|---|---|---|
| JP | 2008529544 A | 8/2008 | | |
| JP | 2009532056 A | 9/2009 | | |
| JP | 2011505826 A | 3/2011 | | |
| JP | 2016512700 A | 5/2016 | | |
| JP | 2018074984 A | 5/2018 | | |
| WO | 2006087243 A1 | 8/2006 | | |
| WO | 2008004058 A2 | 1/2008 | | |
| WO | 2009074970 A2 | 6/2009 | | |
| WO | WO-2017089512 A1 * | 6/2017 | .............. | A61K 9/19 |
| WO | 2020161375 A2 | 8/2020 | | |

OTHER PUBLICATIONS

Salmasi, Z. Heterocyclic amine-modified polyethylenimine as gene carriers for transfection of mammalian cells. Eur. J. Pharm. Biopharm. 2015, 96, 76-88. (Year: 2015).*

Liu, J. cRGD-Modified Benzimidazole-based pH-Responsive Nanoparticles for Enhanced Tumor Targeted Doxorubicin Delivery. ACS Appl. Mater. Interfaces 2016, 8, 10726-10736. (Year: 2016).*

Hao, F. et al. Polyethylenimine-based Formulations for Delivery of Oligonucleotides. Current Medicinal Chemistry 2019, 26, 2264-2284.; published Apr. 1, 2019. (Year: 2019).*

Federal Register, vol. 76, No. 27, Wednesday, Feb. 9, 2011 (Year: 2011).*

Questions and Answers on Ethanol in the context of the revision of the guideline on 'Excipients in the label and package leaflet of medicinal products for human use.' European Medicines Agency, 2014. (Year: 2014).*

Gao et al., "Reversal of multidrug resistance by reduction-sensitive linear cationic click polymer/iMDR1-pDNA complex nanoparticles," Biomaterials, vol. 32, 2011, pp. 1738-1747.

Putnam D. et al., Polymer-Based Gene Delivery with Low Cytotoxicity by a Unique Balance of Side-chain Termini, Proceedings of the National Academy of Sciences, vol. 98, No. 3, Jan. 30, 2001, pp. 1200-1205.

Putnam D. et al., "Polyhistidine-PEG: DNA nanocomposites for gene delivery", Biomaterials, vol. 24, No. 24, Nov. 1, 2003, pp. 4425-4433.

Caroline Diana Sherly M. et al., "Efficiacy of vinyl imidazole grafted cationized pullulan and dextran as gene delivery vectors: A comparative study", International Journal of Biological Macromolecules, vol. 105, Jul. 22, 2017, pp. 947-955.

Abbas Zakeri et al., "Polyethylenimine-based nanocarriers in co-delivery of drug and gene: a developing horizon", Nano Reviews & Experiments, vol. 9, 1488497, Jan. 1, 2018, 14 pages.

Pan Guo et al., "Dual functionalized amino poly(glycerol methacrylate) with guanidine and Schiff-base linked imidazole for enhanced gene transfection and minimized cytotoxicity", Journal of Materials Chemistry B, vol. 3, No. 34, Jan. 1, 2015, pp. 6911-6918.

Sonia Gutierrez-Granados et al., "Advancements in mammalian cell transient gene expression (TGE) technology for accelerated production of biologics", Critical Reviews in Biotechnology, vol. 38, No. 6, Jan. 2, 2018, pp. 918-940.

International Search Report for PCT/EP2020/072065 mailed Oct. 9, 2020, 5 pages.

Written Opinion of the ISA for PCT/EP2020/072065 mailed Oct. 9, 2020, 10 pages.

Putnam D et al., Polymer-Based Gene Delivery with Low Cytotoxicity by a Unique Balance of Side-chain Termini, Proceedings of the National Academy of Sciences, vol. 98, No. 3, Jan. 30, 2001, pp. 1200-1205. (submission pending).

Putnam D et al., "Polyhistidine-PEG: DNA nanocomposites for gene delivery", Biomaterials, vol. 24, No. 24, Nov. 1, 2003, pp. 4425-4433. (submission pending).

Caroline Diana Sherly M et al., "Efficiacy of vinyl imidazole grafted cationized pullulan and dextran as gene delivery vectors: A comparative study", International Journal of Biological Macromolecules, vol. 105, Jul. 22, 2017, pp. 947-955. (submission pending).

Abbas Zakeri et al., "Polyethylenimine-based nanocarriers in co-delivery of drug and gene: a developing horizon", Nano Reviews & Experiments, vol. 9, No. 1, Jan. 1, 2018, p. 1488497. (submission pending).

Pan Guo et al., "Dual functionalized amino poly(glycerol methacrylate) with guanidine and Schiff-base linked imidazole for enhanced gene transfection and minimized cytotoxicity", Journal of Materials Chemistry B, vol. 3, No. 34, Jan. 1, 2015, pp. 6911-6918. (submission pending).

Sonia Gutierrez-Granados et al., "Advancements in mammalian cell transient gene expression (TGE) technology for accelerated production of biologics", CRC Critical Reviews in Biotechnology, vol. 38, No. 6, Jan. 2, 2018, pp. 918-940, (submission pending).

Office Action, issued in Japanese Patent Application No. 2022-507478 dated May 13, 2024.

Office Action, issued in Japanese Patent Application No. 2022-507483 dated Jul. 16, 2024.

Song et al., "Modulation of polypeptide conformation through donor-acceptor transformation of side-chain hydrogen bonding ligands", Nature Communications, 2017, vol. 8, No. 92, pp. 1-8.

Movahedi et al., "Cu(I) stabilizing crosslinked polyethyleneimine", Phys. Chem. Chem. Phys., 2015, vol. 17, pp. 18327-18336.

Office Action, issued in Australian Patent Application No. 2020324543 dated May 1, 2025.

Office Action, issued in Australian Patent Application No. 2020325705 dated May 8, 2025.

Pangon et al., "Polyethylenimine Containing Benzimidazole Branching: A Model System Providing a Balance of Hydrogen Bond Network or Chain Mobility Enhances Proton Conductivity", The Journal of Physical Chemistry B, 2011, vol. 115, pp. 11359-11367.

* cited by examiner

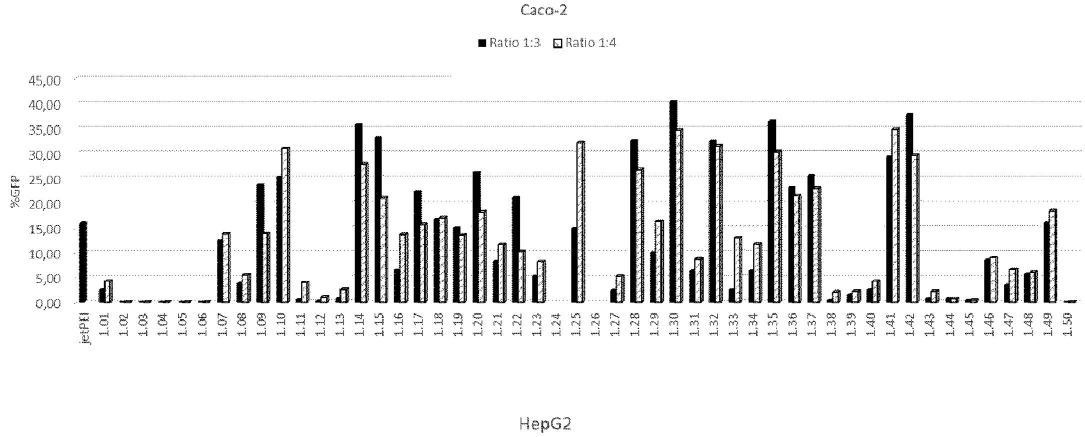
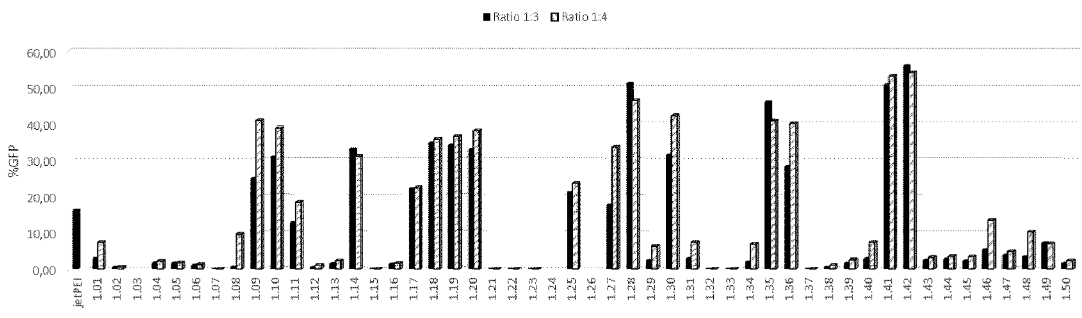
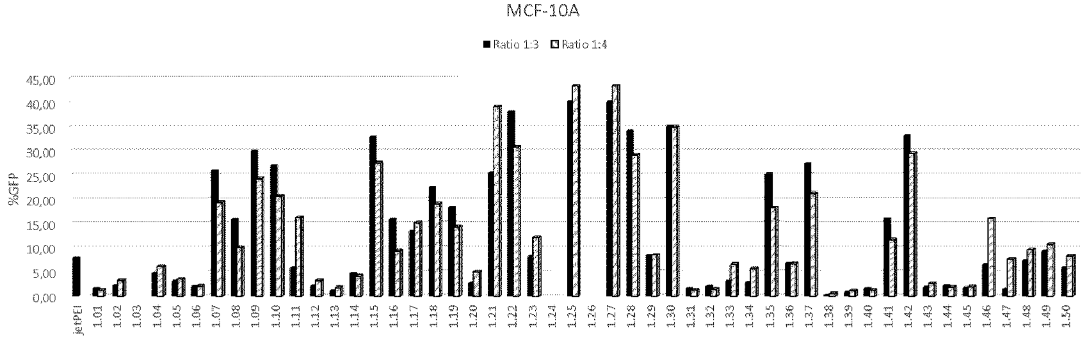
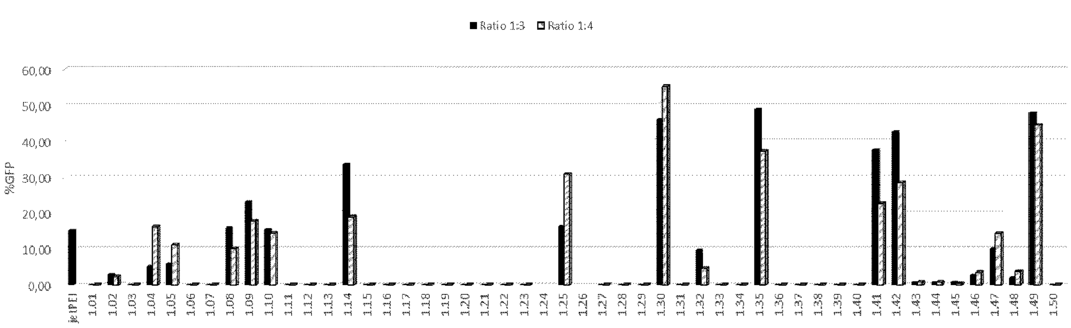
Figure 1

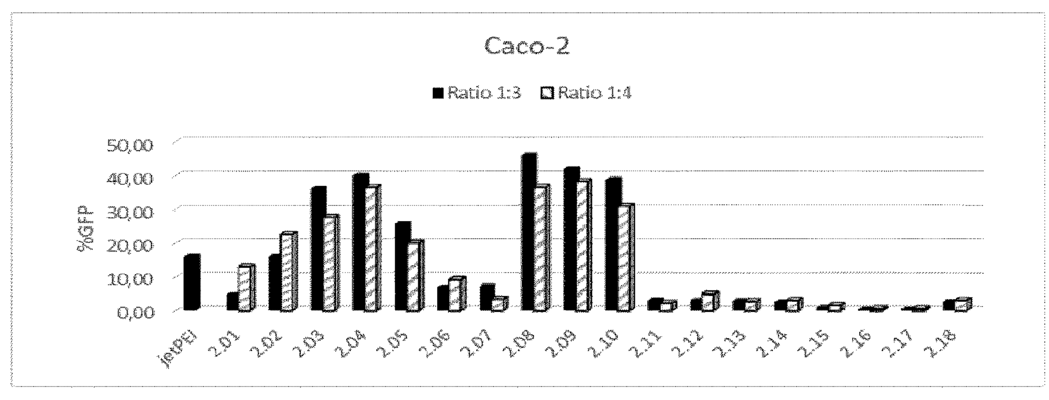
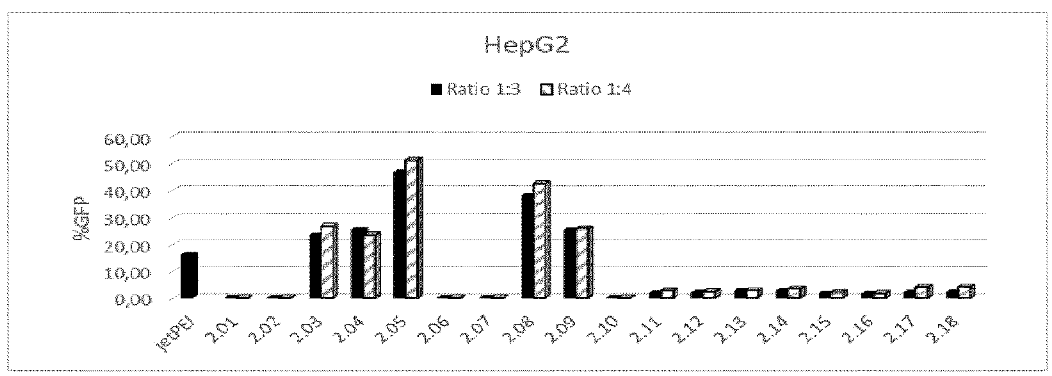
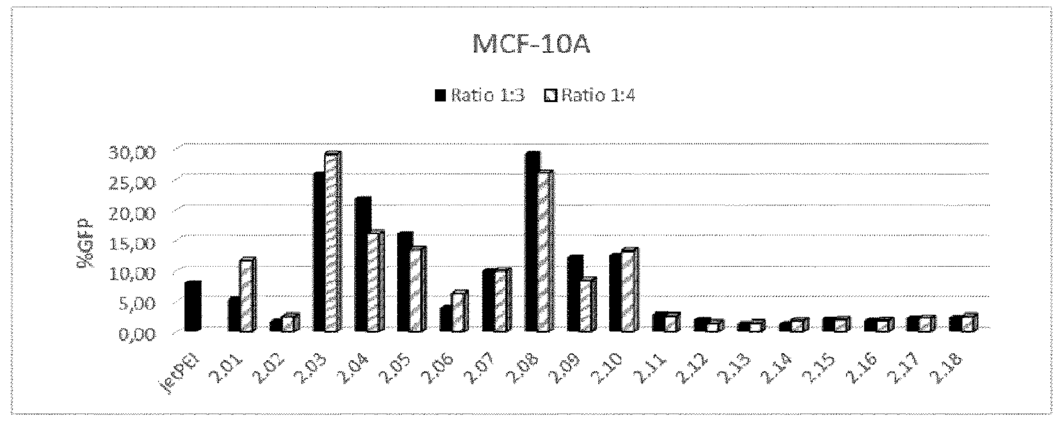
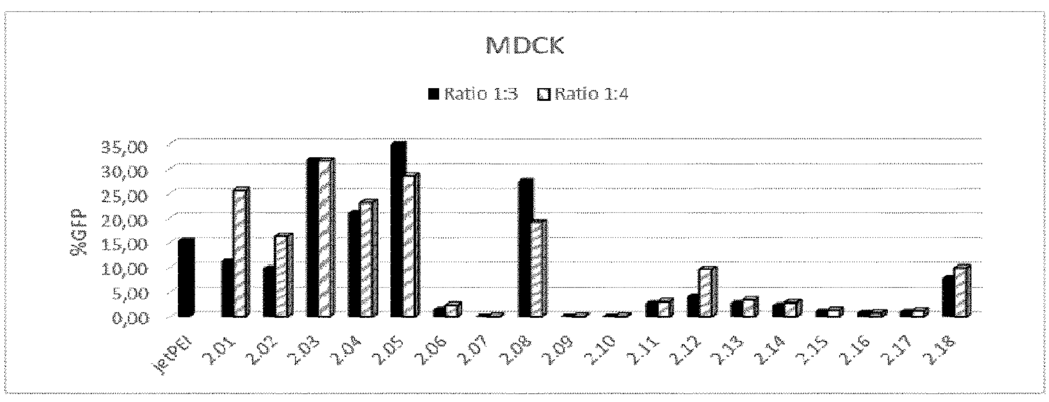
Figure 2

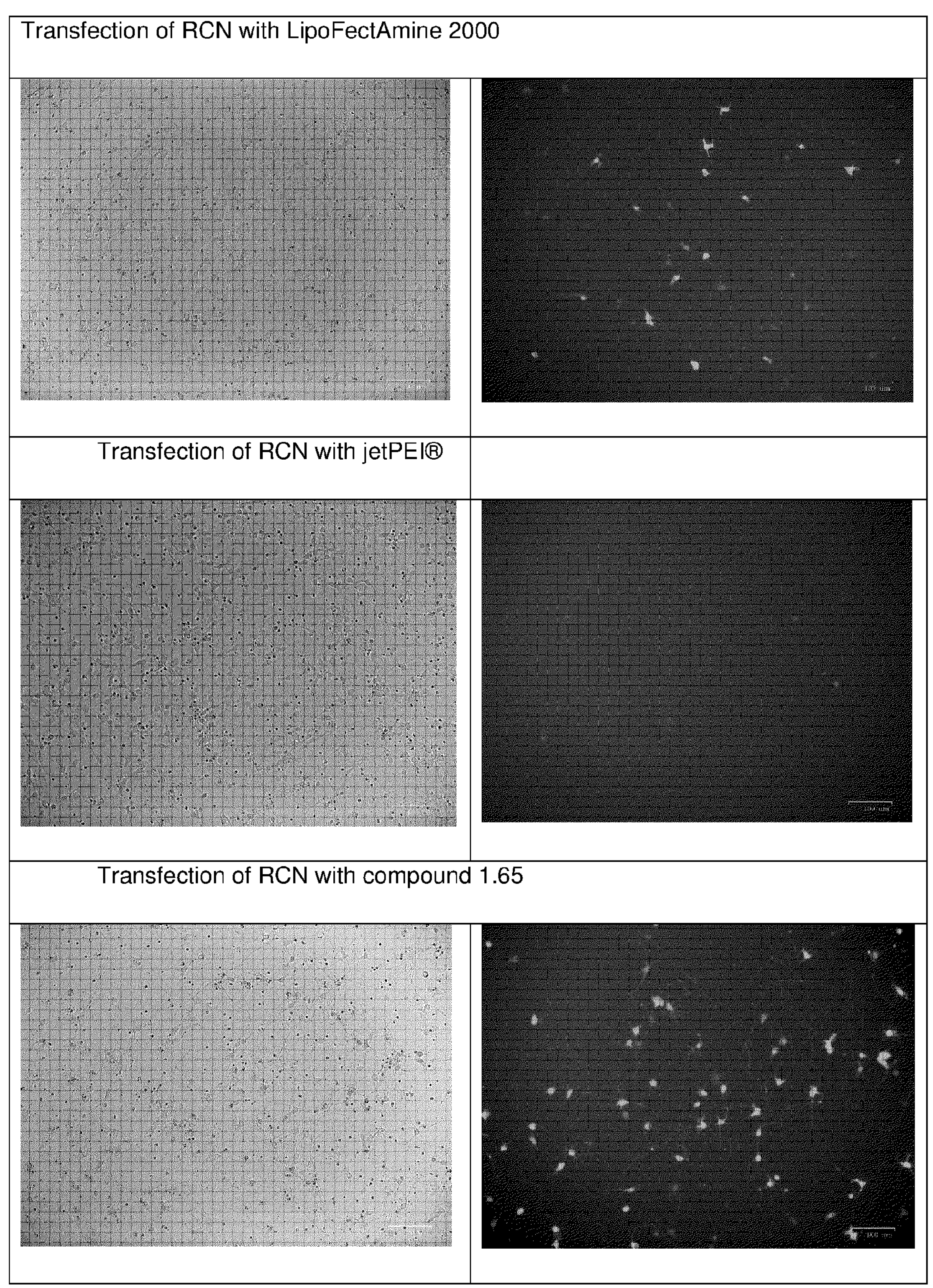
Figure 5 (1/2)

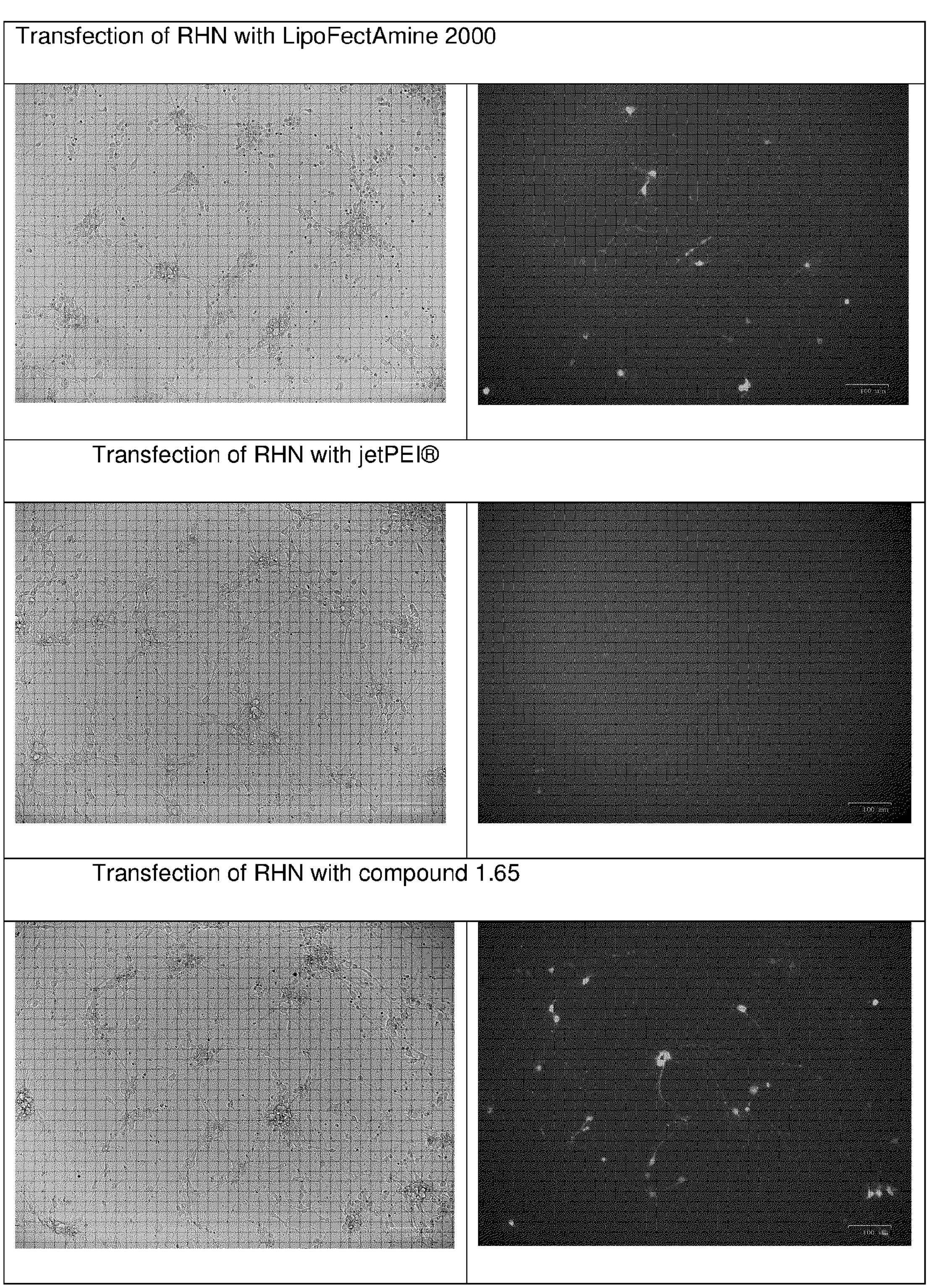
Figure 5 (2/2)

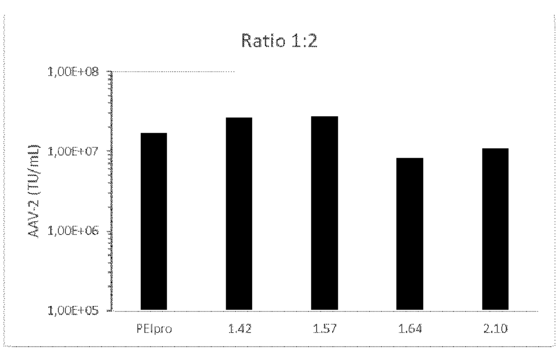
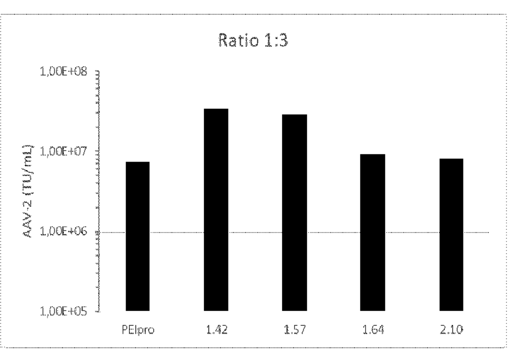
Figure 6
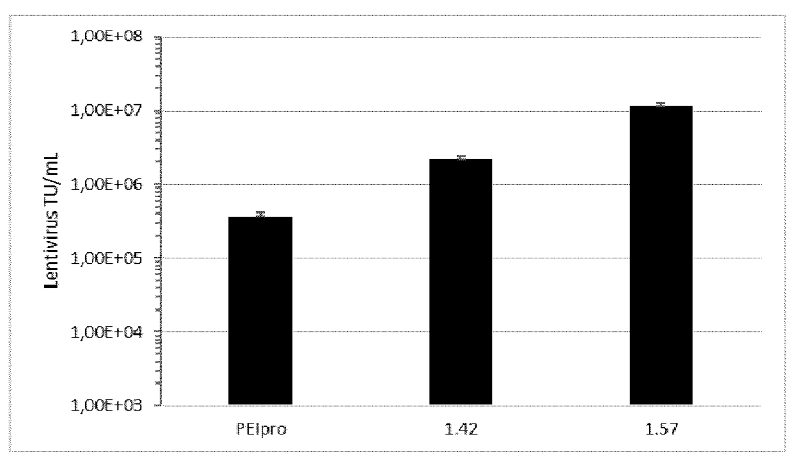
Figure 7
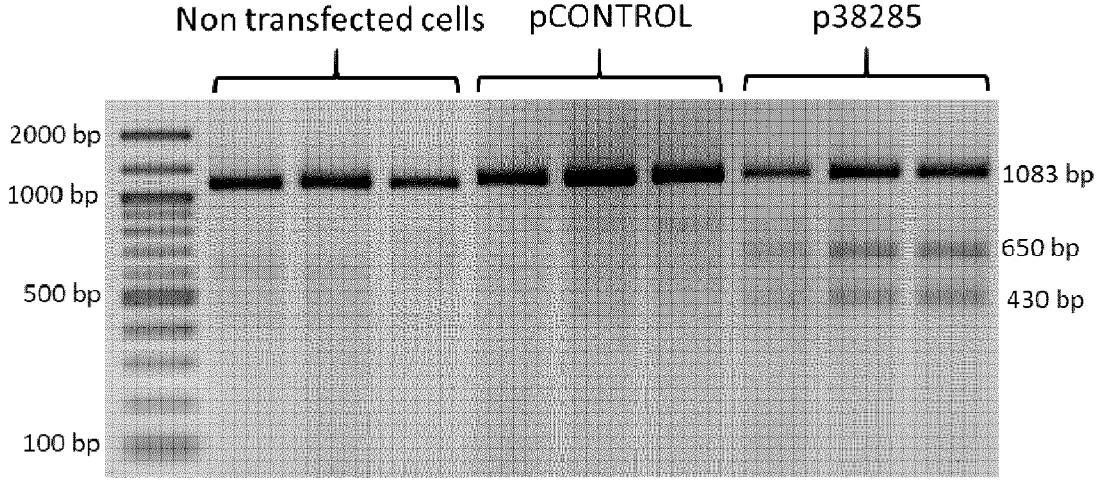
Figure 8

Transfection of human mesenchymal stem cells (hMSC)
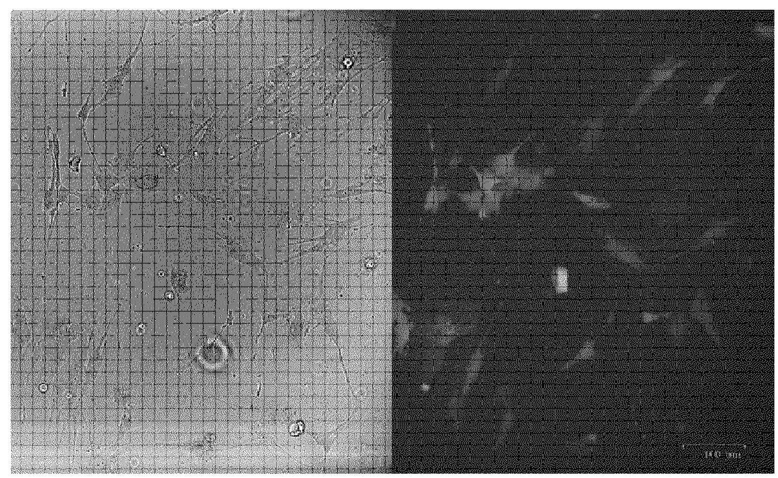
400 ng DNA
2 µL Compound 1.42
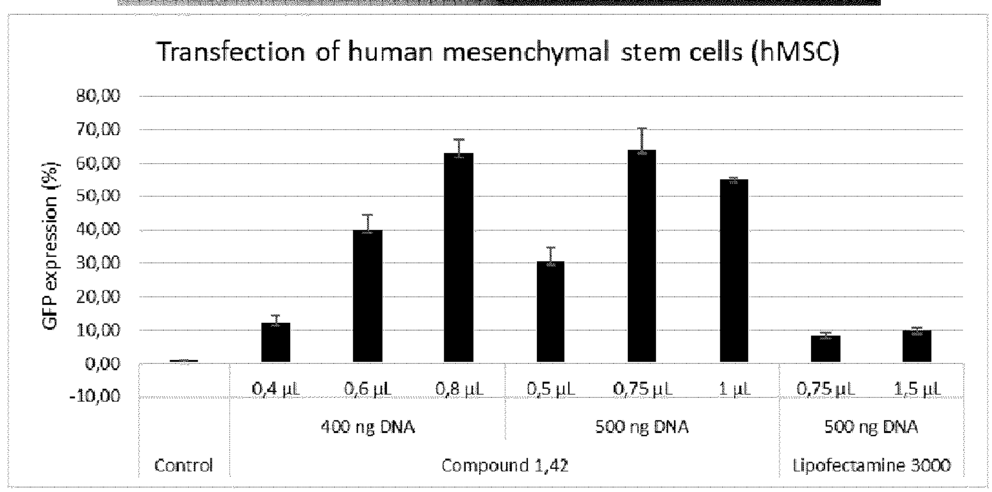
Figure 9
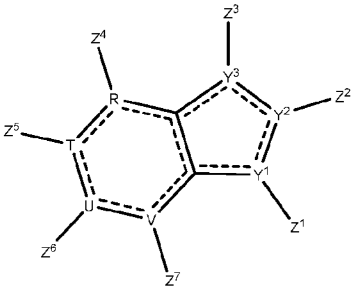
(II)
Figure 10

COMPOSITIONS FOR TRANSFECTING A NUCLEIC ACID MOLECULE INTO A CELL COMPRISING BENZO-FUSED HETEROCYCLIC COMPOUNDS GRAFTED TO A CATIONIC POLYMER, AND THEIR APPLICATIONS

BACKGROUND OF THE INVENTION

Field of the Invention

The present invention relates to compositions for transfecting a nucleic acid molecule into a cell comprising benzo-fused heterocyclic compounds grafted to a cationic polymer, and their applications. The present invention is directed to a composition suitable for transfecting a nucleic acid molecule into a cell, preferably a eukaryotic cell, comprising (i) at least one compound of general formula (II) or a tautomer, mesomer, racemate, enantiomer, diastereomer, or mixture thereof, or an acceptable salt thereof, and (ii) an acceptable excipient, buffering agent, cell culture medium, or transfection medium, wherein $Y^1$, $Y^2$, $Y^3$, $Z^1$, $Z^2$, $Z^3$, $X^1$, $X^2$, $R^3$, $P^+$, R and V are as defined in the description. The present invention also relates to uses of said composition and to a method for in vitro or ex vivo transfection of live cells.

Description of the Related Art

The gene transfer is the process of introducing copies of exogenous genes into living cells in order to induce synthesis of the gene's products. Transfection is the process of deliberately and artificially introducing nucleic acids (DNA or RNA) into eukaryotic cells, utilizing means of non-viral methods. The transfection is of fundamental importance to developments in modern biology and medicine, and has provided much of our knowledge of gene function and regulation.

The transfection according to the invention can be achieved in various cells, including mammalian and insect cells, in primary cells, cell lines, stable cells or tumoral cells. The transfection is a powerful tool for in vitro genomic studies by offering the possibility to express in cells new exogenous proteins or to over-express or silence naturally occurring proteins.

Transfection according to the invention can be applied in therapy through ex vivo or in vivo protocols. Nucleic acid-based therapy with non-viral vectors can target different diseases, genetic diseases, immune diseases, cancers or viral infections in various tissues/organs or tumors. The cell targeting is achieved through different mechanisms and depends on the nature and properties of the transfection reagent, method or protocol composition or formulation and the route of administration (Kaestner et al., 2015).

In bioproduction, transfection according to the invention can be used to generate stable cell clones over-producing recombinant proteins, peptides or antibodies. More recently, the transfection allowing transient gene expression (TGE) is becoming a valuable method for the fast production of moderate level of recombinant proteins or antibodies useful for research and process development phases. Transient gene expression processes are advantageously applied for the production of recombinant viruses such as adeno-associated viruses (AAV), lentiviruses (LV) or adenoviruses (Merten et al., 2016; Van Der Loo and Wright, 2015). Such processes consist of transfecting many expression vectors (plasmids) expressing in cells the different components necessary to produce the viruses including capsid proteins, helper proteins, envelop proteins, viral polymerase or regulators, or viral genomes. High producing cells are used in viral production such as HEK293 and derivative cells, HeLa, BHK-21, A549 or insect cells. The transfection can be achieved in adherent or suspension-adapted cells at high cell density cultured in media containing serum or in protein-free, chemically defined or completely synthetic media.

Transfection is a method to introduce the different components in cells necessary to induce genome modification, engineering or editing such as zing finger nucleases, CRE/LOX proteins or CRISPR Cas-9 proteins.

DNA transfection uses plasmid DNA which triggers the gene expression driven by a promoter of a protein or peptide and/or a nucleic acid such as messenger RNA, long RNA, microRNA, short hairpin RNA, short interfering RNA, . . .

In mainly all cases plasmid DNA has been used for transfection purposes because of its inherent stability and its ability to integrate into the host genome to produce stable gene expression or to remain in the nucleus under an episomal form providing transient gene expression. However, some cells, named 'hard to transfect' cells (HTT) are refractory to DNA transfection or exhibit low levels of transfection and gene expression when compared to standard transformed cells lines routinely used in laboratory settings. These "hard to transfect" cells exhibit less than 50% transfection efficiency when transfected with the last generation of commercially available transfection reagents such as LipoFectAmine® 2000 & 3000 (ThermoFisher) a DOSPA/DOPE cationic lipid formulation), TransIT reagents® (proprietary polymer-based DNA and RNA delivery reagents) (MirusBio), FuGene® (a proprietary lipid-based DNA transfection reagent in 80% ethanol) (Promega), XtremeGene® (a proprietary lipid-based DNA transfection reagent in 80% ethanol) (Roche), jetPRIME® (Polyplus-transfection) or ViaFect® (a proprietary DNA transfection reagent for mammalian cells) (Promega).

Recent progresses to improve the gene expression efficiency of HTT cells are the transfection with messenger RNA (mRNA) sequences rather than plasmid DNA constructs which showed significant increase of transfection and gene expression levels in a majority of cell types, and particularly in challenging HTT cells. The benefice is explained by the fact that the transfected mRNA does not need to reach the nucleus for cellular action contrasting with DNA transfection where the major limitation is to reach and penetrate the nucleus. The plasmid DNA import is not well understood but an efficient DNA transfection is mainly correlated with an active proliferation rate of cells where the transfected DNA may diffuse in the nuclear space during the nuclear membrane breakdown. In most post-mitotic cells or non-dividing cells, DNA transfection is not effective. Most of the HTT cells exhibits a low level or absence of mitosis such as neuronal cells or other cell types derived from neural tissue, primary blood cells like dendritic cells or macrophages, or primary hepatocytes. However, for other HTT cells, the low transfection efficiency might be explained by other factors such as the cell fragility, the low binding of transfection material to the cell plasma membrane, the low endocytosis capacity or a non-efficient intracellular trafficking towards the nucleus of the transfected DNA.

Transfection of plasmid DNA is the most common method to overexpress proteins in cells grown in culture. Most of the methods to introduce genetic DNA material into cells include the use of reagents such as calcium phosphate, cationic liposomes, peptides or polymers. When the transfection fails, the reagent is generally recognized as the culprit. There is still a need to improve the efficiency of transfection reagents particularly for the HTT cells, with new concepts and generation of reagents.

DNA transfection in eukaryotic cells involves combining or mixing the polyanionic DNA molecule with a reagent to form transfection complexes or aggregates. Among the most commonly used reagents, cationic lipids, peptides or polymers are suitable to interact with the negatively charged DNA. If an excess of the cationic reagents is used, complexes or aggregates having a positive character are generated. Such complexes are able to interact with the negatively charged glycosaminoglycans such as heparan sulfates present on the cell plasma membranes (Labatmoleur et al., 1996, Mislick and Baldeschwieler, 1996). The cell membrane binding of complexes induces a cell internalization or uptake by endocytosis mechanism. Transfection complexes are transported into endosomes where transfection reagents exhibit membrane destabilization though fusogenic activity and/or endosomolysis to release DNA in the cytoplasm. Following the release from the endosomes, the transfected DNA has to diffuse towards the perinuclear space and penetrate in the nucleus. The nuclear import is a limiting step as plasmid DNA is not able to diffuse through the nuclear pore complexes because of its large size.

Among the non-viral vectors for DNA transfection, cationic liposomes or aggregates are one of the major classes which consist of combining or formulating cationic lipids with other types of lipids, such as phospholipids or cholesterol, to generate positively charged liposomes, vesicles or micelles that can bind negatively charged DNA and bind negatively charged cell membranes ending by cell transfection. In the prior art, the first synthetic cationic lipid is N-[1-(2,3-dioleoyloxy) propyl]-N,N, N-trimethylammonium chloride (DOTMA) by Felgner et al. When combined with dioleoylphosphatidylethanolamine at a ratio of 1:1, DOTMA formed cationic liposomes that were able to transfect cells in vitro. Based on the positively charged trimethylammonium polar head other monocationic lipids were developed such as 1,2bis(oleoyloxy)-3,3-(trimethylammonium) propane chloride (DOTAP). Other prior art compounds are based on polycationic polar head such as lipids described by Behr et al., 1989, dioctadecylamidoglycylspermine (DOGS) or dipalmitoyl phosphatidylethanolamidospermine (DPPES) where the carboxyspermine was used instead of ammonium group or the phospholipid moiety was replaced by a cholesterol derivative (Gao & Huang, 1991) such as 3β-[N-(N',N'-dimethylaminoethane)-carbamoyl] cholesterol hydrochloride (DC-CHOL). Since these pioneer works, many cationic lipids were designed with the goal to generate novel cationic lipid reagents with increased transfection efficiencies. Many of these reagents are commercially available and the recent LipoFectAmine3000® reagent represents the most advanced reagent of cationic lipids available on the market. However, limitations are still observed as transfection is not effective in all cell types and cell toxicity is still a major concern of cationic lipid systems.

Cationic polymers represent the second major class of transfection reagents with the advantage to offer a large density of charged amino groups in their backbones. Cationic polymers having a positive charge at physiological pH are able to complex DNA into particles or aggregates, initiate cell binding and trigger cell internalisation through endocytosis. Polylysine (PLL) was the first polymer used but showed very limited transfection efficiencies (Wu and Wu, 1987, Zenke et al., 1990). Its efficiency can be improved when additives such as weak bases like chloroquine (Erbacher et al., 1996) or fusogenic peptide like influenza peptides (Planck et al., 1994) were added in order to buffer the acidic pH of destabilize endosomes, respectively, and induce more release of DNA in the cytoplasm. Behr et al. has showed that the polyethylenimine (PEI) was a more effective polymer than PLL in transfection (Boussif et al., 1995). PEI has a high density of amino groups and is not fully protonated at physiological pH. After endocytosis of DNA complexed with PEI, the polymer has buffering capacity which induces a 'proton sponge' activity resulting in vesicles swelling and endosomolysis ending by the release of DNA in the cytoplasm without the help of additives (Boussif et al., 1995; Sonawane et al., 2003). Both branched and linear PEI are efficient in transfection but the linear topology was shown to be more efficient (Itaka et al., 2004), not inhibited by the presence of serum and less toxic when compared to the branched form. Since two decades, many strategies were developed to increase the transfection efficiency of PEI, reduce its toxicity or propose alternative of biodegradable PEI-based polymers.

Many works were concentrated on the optimisation of the intrinsic proton-sponge endosomolytic activities of PEI by grafting histidyl or benzyl residues (U.S. Pat. No. 8,658,150, Chandrashekhar et al., 2012) to the polymers. Other modifications were explored like addition of hydrophilic groups (EP2070970) to increase the solubility of DNA/PEI complexes and reduce the cell toxicity. Hydrophobic functionalities were added to PEI to increase the biodegradability of the polymer using N-acyl groups (EP0262641) or to generate lipopolymers (US20090022746, WO2006/041617). Higher gene transfection efficiencies were observed in various cell lines. However, the efficiency in "hard to transfect" cells remained very limited.

Other cationic polymers were described for DNA transfection such as chitosan (Erbacher et al., 1998), polyamidoamine (PAMAM) dendrimers (Tomalia et al., 1985, Haensler and Szoka, 2003), degraded or fractured dendrimers (Tang et al., 1996), structurally flexible dendrimers (Liu et al., 2011), polyaminoesters (Little et al., 2004), poly(a [4-aminobutyl]-L-glycolic acid) (Akinc et al., 2003), cationic cyclodextrin amphiphiles (Cryan et al., 2004), poly(N-methylvinylamine) (Dréan et al., 2018), poly(2-N-dimethylaminoethyl) methacrylate (PDMAEMA), polyallylamine (Boussif et al., 1999), polyornithine (Dong et al., 1993), polyarginine (Alhakamy et al., 2013), polyhistidine (Putman et al., 2003) and cell penetrating peptides (CPPs) (Gupta, 2005).

It was reported that cationic polymers such as PEI were able to transfect post-mitotic cells (Brunner et al.). However, in the absence of mitosis and the subsequent breakdown of the nuclear membrane, it was shown that plasmid DNA, because of its large size >1 kbp, was not able to enter the nucleus through the nuclear pore complexes (Lukacs et al. 2000). Once released from endosomes, DNA was still associated with some cationic polymers which contributed to protect it against the nuclease degradation (Lechardeur et al., 1999). It is known that DNA is able to interact with proteins present in the cytoplasm, particularly dynein, allowing a microtubule-based movement towards the nucleus or binding of transcription factors having NLS signals, which may direct DNA to the nuclear pore complexes through the importin pathway (Bai et al., 2017).

Cationic polymers represent one class of delivery reagents suitable for in vivo applications for gene therapy approach where DNA/cationic polymer complexes are directly injected through different routes of administration, such as intravenous, intraperitoneal, intradermal, intratumoral or intracacerebral injection. Cationic polymers formulated with an acceptable excipient and/or bufeering agent are suitable for in vivo gene transfer. Particularly, PEI was reported as an efficient polymer for in vivo applications (Boussif et al., 1995).

Due to their special structural features and electron-rich environment, benzimidazole-containing derivatives bind to a variety of targets, such as DNA or proteins, and exhibit a broad spectrum of bioactivities (Gaba and Mohan, 2016). Benzimidazole ring is structurally similar to purine bases. Many benzimidazole derivatives were found to be minor groove binders of DNA (Ivanov et al., 2013; Gao et al., 2013). Changing the chemical structure of the benzimidazole ligands may modulate DNA binding mode and the sequence selectivity (Bazhulina et al., 2009; Tari et al., 2017). Benzimidazole derivatives have also the ability to accumulate in the nucleus such as the Hoechst 33258 compound. Other derivatives were found to inhibit the H/K ATPase activity (Fellenius et al., 1981). Minor modifications of benzimidazole ring, like methyl, ethyl, amino groups, may modulate the pKa value where a range of 5-6 should be of interest for buffering capacity (Brown and Mora-Diez, 2006).

SUMMARY OF THE INVENTION

The inventors provide a way to improve transfection reagent by using benzo-fused heterocyclic compounds to fine-tune the affinity and binding to a nucleic acid molecule, e.g. DNA, optimize the buffering capacity in acidic conditions and/or increase the diffusion, binding and uptake in the nucleus.

Thus it is an object of the present invention to provide a more efficient transfection composition or a formulation for transfecting a nucleic acid molecule into a cell.

It is another object of the present invention to provide a method for transfecting a nucleic acid molecule using said composition or formulation comprising such composition for administration to cells.

The inventors carried out a structure-based screening of substituted heterocyclic compounds, in particular benzimidazole, benzopyrazole, benzotriazole, to improve the efficiency of transfection by cationic polymers. Such substituted heterocyclic compounds were grafted to cationic polymers, in particular polyethylenimine (PEI) polymers, of various molecular weight in order to fine-tune the conjugates. Many variations were proposed in order to define optimal structures facilitating transfection of a nucleic acid molecule, e.g. DNA. Heterocycles exhibiting hydrophobic properties were developed and may represent binding motifs to cytoplasmic proteins promoting potentially the nuclear import.

The present invention relates to a composition suitable for transfecting a nucleic acid molecule, preferably a deoxyribonucleic acid (DNA) into a cell, preferably a eukaryotic cell, comprising (i) at least one compound of general formula (II) or a tautomer, mesomer, racemate, enantiomer, diastereomer, or mixture thereof, or an acceptable salt thereof, and (ii) an acceptable excipient, buffering agent, cell culture medium, or transfection medium:

(II)

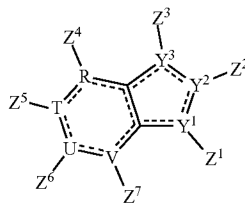

wherein:

$Y^1$, $Y^2$ and $Y^3$, which may be identical or different, represent C or N, with the proviso that at least two of $Y^1$, $Y^2$ and $Y^3$ are N, and with the further proviso that at least one, but no more than two, of $Y^1$, $Y^2$ and $Y^3$ are substituted by $Z^1$, $Z^2$ and $Z^3$ respectively;

$Z^1$ represents H, $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$; or $Z^1$ is absent;

$Z^2$ represents H, a linear or branched, saturated or unsaturated $C_1$-$C_{18}$ alkyl, $C_6$-$C_{18}$ aryl, a linear or branched, saturated or unsaturated $C_6$-$C_{18}$ aryl-$C_1$-$C_{18}$ alkyl, a linear or branched, saturated or unsaturated $C_2$-$C_{18}$ heteroalkyl, $C_5$-$C_{10}$ heteroaryl, halogen, OH, a linear or branched, saturated or unsaturated $C_1$-$C_{18}$ alkylamine, a $C_1$-$C_{12}$ alkoxy, a linear or branched, saturated or unsaturated $C_1$-$C_{18}$ alkyl-$C_1$-$C_{12}$ alkoxy, $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$; or $Z^2$ is absent;

$Z^3$ represents H, a linear or branched, saturated or unsaturated $C_1$-$C_{18}$ alkyl, $C_6$-$C_{18}$ aryl, a linear or branched, saturated or unsaturated $C_6$-$C_{18}$ aryl-$C_1$-$C_{18}$ alkyl, $C_5$-$C_{10}$ heteroaryl, a linear or branched, saturated or unsaturated $C_2$-$C_{18}$ heteroalkyl, $C_2$-$C_{18}$ alkylidene, OH, guanidine, halogen, $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$; or $Z^3$ is absent;

$X_1$ and $X_2$, which may be identical or different, represent CO or $CH_2$;

$R_3$ represents $(CH_2)_m$, $(CH_2)_m—CHCH_3—(CH_2)_n—$, $(CH_2)_m—C(CH_3)_2—(CH_2)_n—$, $(CH_2)_m—O—(CH_2)_n—$, $(CH_2)_m—S—(CH_2)_n—$, $(CH_2)_m—CH_2—O—$, with m representing an integer between 1 and 3 and n representing an integer between 1 and 3;

$P^+$ represents a graft cationic polymer, which is a polyamine comprising secondary amines, tertiary amines, a mixture of primary and secondary amines, a mixture of primary and tertiary amines, a mixture of secondary and tertiary amines, or a mixture of primary, secondary and tertiary amines;

R, T, U and V, which may be identical or different, represent C or N, with the proviso that the six-membered ring of (II) contains no more than 2 N atoms;

$Z^4$, $Z^5$, $Z^6$ and $Z^7$, which may be identical or different, represent H, a linear or branched, saturated or unsaturated $C_1$-$C_{18}$ alkyl, $C_6$-$C_{18}$ aryl, a linear or branched, saturated or unsaturated $C_6$-$C_{18}$ aryl-$C_1$-$C_{18}$ alkyl, $C_5$-$C_{10}$ heteroaryl, a linear or branched, saturated or unsaturated $C_2$-$C_{18}$ heteroalkyl, an amine, a linear or branched, saturated or unsaturated $C_1$-$C_{18}$ alkylamine, a $C_1$-$C_{12}$ alkoxy, $C_2$-$C_{18}$ alkylidene, OH, guanidine, or halogen; or (i) $Z^4$ and $Z^5$ or (ii) $Z^5$ and $Z^6$ or (iii) $Z^6$ and $Z^7$ together form a fused, optionally substituted 6-membered aryl or heteroaryl;

with the proviso that:

only one of $Z^1$, $Z^2$ or $Z^3$ represents $X_1$—$R_3$—$X_2$—$P^+$, $X_1$—$R_3$—$P^+$, $X_1$—$X_2$—$P^+$, $R_3$—$X_2$—$P^+$, $X_1$—$P^+$, $R_3$—$P^+$, or $X_2$—$P^+$.

As defined herein, the term "tautomer" refers to structural isomers differing only in the positions of hydrogen atoms and electrons. Examples of tautomers include, but are not limited to, ketone-enol, enamine-imine, amide-imidic acid, lactam-lactim, nitroso-oxime, ketene-ynol, amino acid, or phosphite-phosphonate.

As defined herein, the term "mesomer" or "meso compound" refers to a stereoisomer that has two or more chiral centers but is optically inactive.

As defined herein, the term "racemate" or "racemic mixtures" refers to a mixture of two enantiomers in equal proportions.

As defined herein, the term "enantiomer" refers stereoisomers that are mirror images, i.e. mirror image isomers.

As defined herein, the term "diastereomer" refers to isomers of compounds with more than one chiral center that are not mirror images of one another.

As defined herein, the term "acceptable excipient" refers to a pharmaceutically acceptable vehicle, which is any substance or combination of substances physiologically acceptable i.e., appropriate for its use in a composition in contact with a host, especially a human, and thus non-toxic. It can refer to a solid, semi-solid or liquid filler, diluent, encapsulating material or formulation auxiliary of any conventional type. Examples of suitable acceptable excipients include, but are not limited to, glucose, galactose, lactose, dextrose, maltose, mannitol, sucrose, trehalose, polyethyleneglycol, or pluronic acid.

As defined herein, the term "buffering agent" refers to an agent that adjusts, maintains or controls the pH of a solution. Buffering agents can be either the weak acid or weak base that would comprise a buffer solution. Examples of suitable buffering agents include, but are not limited to, sodium carbonate, sodium bicarbonate, sodium hydroxide, calcium bicarbonate, calcium citrate, sodium citrate, magnesium hydroxide, magnesium bicarbonate, potassium acetate, Tris acetate, sodium acetate, potassium phosphate monobasic, potassium carbonate, potassium bicarbonate, potassium citrate, or magnesium oxide.

As defined herein, the term "cell culture medium" or "transfection medium" refers to a medium containing serum, synthetic medium, animal-free component medium or chemically defined medium, in particular medium for maintaining cells alive, or for growing, for differentiating or for expanding cells, or for enhancing transfection.

As defined herein, the term "$C_1$-$C_{18}$ alkyl" represents any monovalent radical of a linear or branched hydrocarbon chain comprising 1 to 18 carbon atoms. The term "$C_1$-$C_6$ alkyl" represents an alkyl group having 1 to 6 carbon atoms. Examples of suitable $C_1$-$C_{18}$ alkyl groups include, but are not limited to, $C_1$-$C_4$ alkyl groups such as methyl, ethyl, n-propyl, i-propyl, n-butyl, i-butyl, s-butyl or t-butyl, $C_6$-$C_8$ alkyl groups such as n-hexyl, n-heptyl or n-octyl, as well as n-pentyl, 2-ethylhexyl, 3,5,5-trimethylhexyl, n-nonyl, n-decyl, n-undecyl, n-dodecyl or n-octadecyl.

As defined herein, the term "$C_1$-$C_{12}$ alkoxy" represents a radical of formula —OR', wherein R' is a $C_1$-$C_{12}$ alkyl. Examples of suitable $C_1$-$C_{12}$ alkoxy groups include, but are not limited to, $C_1$-$C_6$ alkoxy groups such as methoxy ($—OCH_3$), ethoxy ($—OCH_2CH_3$), t-butoxy ($—OC(CH_3)_3$), or $—O(CH_2)_5CH_3$.

As defined herein, the term "$C_6$-$C_{18}$ aryl" represents any monovalent radical of an aromatic hydrocarbon comprising 6 to 18 carbon atoms. Examples of suitable $C_6$-$C_{18}$ aryl groups include, but are not limited to, phenyl, naphthyl, anthracenyl or phenanthrenyl.

As defined herein, the term "$C_6$-$C_{18}$ aryl-$C_1$-$C_{18}$ alkyl" represents an aryl group as defined herein combined to an alkyl group as defined herein. Examples of suitable $C_6$-$C_{18}$ aryl-$C_1$-$C_{18}$ alkyl groups include, but are not limited to, benzyl, phenylethyl (or phenethyl), phenylpropyl, phenylbutyl, phenylpentyl, phenylhexyl, naphthylmethyl, naphthylethyl, naphthylpropyl, naphthylbutyl, naphthylpentyl, naphthylhexyl, anthracenylmethyl, anthracenylethyl, anthracenylpropyl, anthracenylbutyl, anthracenylpentyl, anthracenylhexyl, phenanthrenylmethyl, phenanthrenylethyl, phenanthrenylpropyl, phenanthrenylbutyl, phenanthrenylpentyl or phenanthrenylhexyl.

As defined herein, the term "$C_2$-$C_{18}$ heteroalkyl" represents an alkyl group as defined herein substituted by one or more heteroatoms such as O, N, or S.

As defined herein, the term "$C_5$-$C_{10}$ heteroaryl" represents any monovalent radical of a monocyclic or bicyclic 5 to 10 membered aromatic group comprising from 1 to 3 heteroatoms independently selected from oxygen, nitrogen and sulfur. Examples of suitable $C_5$-$C_{10}$ heteroaryl groups include, but are not limited to, furyl, thienyl, pyrrolyl, pyrazoyl, imidazolyl, isoxazolyl, isothiazoyl, thiazolyl, oxazolyl, 1,2,3-triazolyl, 1,2,4-triazolyl, 1-benzofuryl, 1-benzothienyl, indolyl, benzimidazolyl, indazolyl, 1,2-benzisoxazolyl, 2,1-benzisoxazolyl, 1,2-benzisothiazolyl, 2,1-benzisothiazolyl, benzothiazolyl, benzoxazolyl, benzotriazolyl, pyridyl, pyridinium, quinolinyl, quinolinium, isoquinolinyl, isoquinolinium, pyridazinyl, cinnolinyl, phthalazinyl, pyrimidinyl, quinazolinyl, pyrazinyl or quinoxalinyl.

As defined herein, the term "$C_1$-$C_{18}$ alkylamine" represents any monovalent radical of a linear or branched hydrocarbon chain comprising 1 to 18 carbon atoms, in which one of the hydrogen atom bonded to a carbon atom is replaced by an amino group. Examples of suitable $C_1$-$C_{18}$ alkylamine include, but are not limited to, $—(CH_2)_n—NH_2$, with n representing an integer between 1 and 18, $—CH_2NHCH_3$, $—CH_2CH(CH_3)—NH_2$, or $—(CH_2)_n N(CH_3)_2$, with n representing an integer between 1 and 6.

As defined herein, the term "$C_1$-$C_{18}$ alkyl-$C_1$-$C_{12}$ alkoxy" represents an alkyl group as defined herein combined to an alkoxy group as defined herein.

As defined herein, the term "$C_2$-$C_{18}$ alkylidene" refers to a divalent group derived from an alkane by removal of two hydrogen atoms from the same carbon atom, the free valencies being part of a double bond ($=CR_2$). Examples of suitable $C_2$-$C_{18}$ alkylidene include, but are not limited to, $=CH_2$, $=CH(CH_2CH_3)$, or $=C(CH_3)_2$.

As defined herein, the term "halogen" represents an atom of F, Cl, Br or I.

As defined herein, the term "$C_1$-$C_{24}$ ester" represents a radical of formula —C(O) OR", wherein R" is a $C_1$-$C_{24}$ alkyl, in particular a $C_1$-$C_{18}$ alkyl as defined herein.

As defined herein, the term "$C_5$-$C_{10}$ heterocyclyl" refers to any monovalent radical of a monocyclic or bicyclic 5 to 10 membered ring containing one or more heteroatoms such as O, N, or S. Examples of suitable heterocyclyl groups include, but are not limited to, piperidinyl, piperazinyl, tetrahydropyranyl, morpholinyl, thiomorpholinyl or azepanyl.

Unless mentioned otherwise, the groups and radicals defined hereinabove may be unsubstituted or substituted by one or more substituents such as, for example, halogen, alkyl, alkoxy, aryl, heteroaryl, haloalkyl, haloalkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino.

In a particular embodiment of the invention, the composition further comprises at least one nucleic acid molecule to be transfected in a cell. Preferably said nucleic acid molecule is selected from the group consisting of a deoxyribonucleic acid (DNA), a ribonucleic acid (RNA), a DNA/RNA hybrid, a short interfering RNA (siRNA), a microRNA (miRNA), a short hairpin RNA (shRNA), a messenger RNA (mRNA), a CRISPR guide RNA, and an expression vector encoding said nucleic acid molecule, in particular a plasmid encoding said nucleic acid molecule, or a plasmid expressing said nucleic acid molecule such as siRNA, microRNA, shRNA, CRISPR guide RNA. Even more preferably, said nucleic acid molecule is a deoxyribonucleic acid (DNA).

When distinct nucleic acids are provided in the composition of the invention, they may be all DNA molecules or all RNA molecules or may be mixtures of DNA and RNA molecules or molecules comprising an association of DNA and RNA strands.

Said nucleic acid molecule may be single stranded or double stranded, and may contain modified or unmodified bases.

The terms "polynucleotide", "nucleic acid", "oligonucleotide", and "nucleic acid molecule" are used interchangeably herein to designate these nucleic acid molecules.

The composition according to the invention may be used as a formulation of the nucleic acid molecule with the at least one compound of general formula (II) (including any of its particular embodiments disclosed herein) and the acceptable excipient, buffering agent, cell culture medium, or transfection medium, in accordance with the disclosure provided herein. It may alternatively be used as a cell culture or as expanded cells, wherein prior to being provided as a culture and/or as expanded cells, isolated cells have been treated with said formulation for transfection. Otherwise stated, the composition of the invention encompasses, as an embodiment, a cell or a cell culture or expanded cells wherein said formulation has been introduced by transfection according to the invention. The cells are in particular mammalian cells, preferably human cells. The cells may be dividing cells or non-dividing cells.

In a particular embodiment of the invention, the composition according to the invention comprises from 1 to 5, preferably at least two distinct compounds of general formula (II), or a tautomer, mesomer, racemate, enantiomer, diastereomer, or mixture thereof, or an acceptable salt thereof.

In a particular embodiment of the invention, the at least one preferred compound of general formula (II) as defined herein is one wherein: (i) $Y^1$ and $Y^3$ represent N, $Y^2$ represents C; or (ii) $Y^1$ and $Y^2$ represent N, $Y^3$ represents C; or (iii) $Y^2$ and $Y^3$ represent N, $Y^1$ represents C; or (iv) $Y^1$, $Y^2$ and $Y^3$ represent N.

In a particular embodiment of the invention, the at least one preferred compound of general formula (II) as defined herein is one wherein (i) $Z^1$ represents H; or (ii) $Z^1$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined herein; more preferably $Z^1$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2.

In a particular embodiment of the invention, the at least one preferred compound of general formula (II) as defined herein is one wherein (i) $Z^2$ represents H, a $C_1$-$C_{12}$ alkoxy, or a linear or branched, saturated or unsaturated $C_1$-$C_{18}$ alkyl, preferably a linear or branched, saturated or unsaturated $C_1$-$C_6$ alkyl; more preferably $Z^2$ represents H, $CH_3$, $CF_3$ or $OCH_3$; even more preferably $Z^2$ represents $CH_3$; or (ii) $Z^2$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined herein; more preferably $Z^2$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2.

In a particular embodiment of the invention, the at least one preferred compound of general formula (II) as defined herein is one wherein (i) $Z^3$ represents H, a linear or branched, saturated or unsaturated $C_1$-$C_{18}$ alkyl, preferably a linear or branched, saturated or unsaturated $C_1$-$C_6$ alkyl, or a linear or branched, saturated or unsaturated $C_6$-$C_{18}$ aryl-$C_1$-$C_{18}$ alkyl, preferably fluorobenzyl or 4-hydroxyphenethyl; or (ii) $Z^3$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined herein; more preferably $Z^3$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2.

In a preferred embodiment of the invention, if (i) $Z^1$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined herein; more preferably $Z^1$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2 then (ii) $Z^2$ represents H, a $C_1$-$C_{12}$ alkoxy, or a linear or branched, saturated or unsaturated $C_1$-$C_{18}$ alkyl, preferably a linear or branched, saturated or unsaturated $C_1$-$C_6$ alkyl; more preferably $Z^2$ represents H, $CH_3$, $CF_3$ or $OCH_3$; and/or (iii) $Z^3$ represents H, a linear or branched, saturated or unsaturated $C_1$-$C_{18}$ alkyl, preferably a linear or branched, saturated or unsaturated $C_1$-$C_6$ alkyl, or a linear or branched, saturated or unsaturated $C_6$-$C_{18}$ aryl-$C_1$-$C_{18}$ alkyl, preferably fluorobenzyl or 4-hydroxyphenethyl.

In another preferred embodiment of the invention, if (i) $Z^2$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined herein; more preferably $Z^2$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2 then (ii) $Z^1$ represents H; and/or (iii) $Z^3$ represents H, a linear or branched, saturated or unsaturated $C_1$-$C_{18}$ alkyl, preferably a linear or branched, saturated or unsaturated $C_1$-$C_6$ alkyl, or a linear or branched, saturated or unsaturated $C_6$-$C_{18}$ aryl-$C_1$-$C_{18}$ alkyl, preferably fluorobenzyl or 4-hydroxyphenethyl.

In another preferred embodiment of the invention, if (i) $Z^3$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined herein; more preferably $Z^3$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2 then (ii) $Z^1$ represents H; and/or (iii) $Z^2$ represents H, a $C_1$-$C_{12}$ alkoxy, or a linear or branched, saturated or unsaturated $C_1$-$C_{18}$ alkyl, preferably a linear or branched, saturated or unsaturated $C_1$-$C_6$ alkyl; more preferably $Z^2$ represents H, $CH_3$, $CF_3$ or $OCH_3$.

In a particular embodiment of the invention, the at least one preferred compound of general formula (II) as defined herein is one wherein: (i) only one of $Z^1$, $Z^2$ or $Z^3$ represents $X_1$—$R_3$—$X_2$—$P^+$, $X_1$—$R_3$—$P^+$, $X_1$—$X_2$—$P^+$, $R_3$—$X_2$—$P^+$, $X_1$—$P^+$, $R_3$—$P^+$, or $X_2$—$P^+$, preferably $X_1$—$R_3$—$X_2$—$P^+$, wherein $X_1$, $X_2$, $R_3$ and $P^+$ are as defined herein; more preferably only one of $Z^1$, $Z^2$ or $Z^3$ represents $X_1$—$R_3$—$X_2$—$P^+$, wherein $X_1$ represents $CH_2$, $X_2$ represents CO, and $R_3$ represents $(CH_2)_m$, with m representing an integer between 1 and 3, preferably m is equal to 2; and/or (ii) $Z^1$ represents H; and/or (iii) $Z^2$ represents H, a $C_1$-$C_{12}$ alkoxy, or a linear or branched, saturated or unsaturated $C_1$-$C_{18}$ alkyl, preferably a linear or branched, saturated or unsaturated $C_1$-$C_6$ alkyl; more preferably $Z^2$ represents H, $CH_3$, $CF_3$ or $OCH_3$; and/or (iv) $Z^3$ represents H, or a linear or branched, saturated or unsaturated $C_1$-$C_{18}$ alkyl, preferably a linear or branched, saturated or unsaturated $C_1$-$C_6$ alkyl.

In a particular embodiment of the invention, the at least one preferred compound of general formula (II) as defined herein is one wherein the graft cationic polymer is selected from the group consisting of a linear or branched polyethyleneimine (PEI), PEI dendrimers, a polypropyleneimine (PPI), Poly(amidoamine) (PAA) and dendrimers (PAMAM), cationic cyclodextrin, polyalkylamine, a polyhydroxyalkylamine, poly(butyleneimine) (PBI), spermine, a N-substituted polyallylamine, N-substituted chitosan, a N-substituted polyornithine, a N-substituted polylysine (PLL), a N-substituted polyvinylamine, poly(β-amino ester), hyperbranched poly(amino ester) (h-PAE), networked poly(amino ester) (n-PAE), poly(4-hydroxy-1-proline ester) (PHP-ester) and a poly-β-aminoacid, preferably is a linear or branched PEI, more preferably is a linear PEI.

The graft cationic polymer may have a grafting ratio ranging from 1 to 50%, preferably from 5 to 30%, more preferably is 20%.

As defined herein, the term "grafting ratio" refers to the number of grafted monomers on primary, secondary or tertiary amino groups by side chains, divided by the number of total monomers present in the original cationic polymer. The grafting ratio will depend upon the molecular weight of the cationic polymer, the chemical reactivity of the grafted side chains onto the polymer, or the obtained biological effect. Said grafting ratio may be determined by a measurement method well known in the art, for example by NMR.

The graft cationic polymer may have an average molecular weight (Mw) ranging from 1 kDa to 500 kDa, preferably from 1 kDa to 50 kDa, more preferably from 5 kDa to 50 kDa or from 1 kDa to 15 kDa. In particular the graft cationic polymer may have an average molecular weight (Mw) of 6, 8, 10, 15, 22 or 30 kDa, preferably of 6, 8, 10, 15 or 30 kDa.

The graft cationic polymer can be associated with a counterion such as chloride, phosphate, citrate, acetate, propionate, carbonate, succinate, sulfonate, sulfate, or carboxylate.

In one embodiment of the invention, the at least one preferred compound of formula (II) as defined herein is one wherein (i) R, T, U and V represent C; or (ii) R, T, U and V, which may be identical or different, represent C or N, with the proviso that the six-membered ring of (II) contains no more than 1 N atom; preferably, one of R, T, U or V represents N; or (iii) R and U represent N, and T and V represent C; or R and T represent N, and U and V represent C; or R and V represent N, and T and U represent C; or T and U represent N, and R and V represent C; or T and V represent N, and R and U represent C. In one preferred embodiment of this first particular embodiment of the invention, the at least one preferred compound of formula (II) as defined herein is one wherein (i) R, T, U and V represent C.

In one embodiment of the invention, the at least one preferred compound of formula (II) as defined herein is one wherein $Z^4$, $Z^5$, $Z^6$ and $Z^7$, which may be identical or different, represent H, OH, halogen, halogen-substituted $C_1$-$C_{12}$ alkyl, an amine, a linear or branched, saturated or unsaturated $C_1$-$C_{18}$ alkylamine, a $C_1$-$C_{12}$ alkoxy, or a linear or branched, saturated or unsaturated $C_1$-$C_{18}$ alkyl, preferably a linear or branched, saturated or unsaturated $C_1$-$C_6$ alkyl; more preferably $Z^4$, $Z^5$, $Z^6$ and $Z^7$, which may be identical or different, represent H, $CH_3$, $NH_2$, or $OCH_3$.

In one particular embodiment of the invention, the at least one preferred compound of formula (II) as defined herein is one wherein $Z^4$, $Z^5$, $Z^6$ and $Z^7$ represent H.

In one particular embodiment of the invention, the at least one preferred compound of formula (II) as defined herein is one wherein $Z^1$ represents $X_1$—$R_3$—$X_2$—$P^+$, wherein $X_1$, $X_2$, $R_3$ and $P^+$ are as defined above; more preferably $Z^1$ represents $X_1$—$R_3$—$X_2$—$P^+$, wherein $X_1$ represents $CH_2$, $X_2$ represents CO, and $R_3$ represents $(CH_2)_m$, with m representing an integer between 1 and 3, preferably m is equal to 2 and $P^+$ represents a linear or branched PEI, preferably a linear PEI.

In one particular embodiment of the invention, the at least one preferred compound of formula (II) as defined herein is one wherein $Z^2$ represents a linear or branched, saturated or unsaturated $C_1$-$C_6$ alkyl, preferably $Z^2$ represents $CH_3$.

In one particular embodiment of the invention, the at least one preferred compound of formula (II) as defined herein is one wherein one of $Z^4$, $Z^5$, $Z^6$ or $Z^7$ represents a linear or branched, saturated or unsaturated $C_1$-$C_6$ alkyl, preferably one of $Z^4$, $Z^5$, $Z^6$ or $Z^7$ represents $CH_3$.

In one particular embodiment of the invention, the at least one preferred compound of formula (II) as defined herein is one wherein $Z^4$ and $Z^6$ represent a linear or branched, saturated or unsaturated $C_1$-$C_6$ alkyl, preferably $Z^4$ and Ze represent $CH_3$.

In one particular embodiment of the invention, the at least one preferred compound of formula (II) as defined herein is one wherein $Z^5$ and $Z^6$ represent a linear or branched, saturated or unsaturated $C_1$-$C_6$ alkyl, preferably $Z^5$ and Ze represent $CH_3$.

In one particular embodiment of the invention, the at least one preferred compound of formula (II) as defined herein is one wherein:

- $Y^1$ and $Y^3$ represent N, $Y^2$ represents C; and
- R, T, U and V represent C; and
- $Z^2$, $Z^4$ and $Z^6$ represent a linear or branched, saturated or unsaturated $C_1$-$C_6$ alkyl, preferably $Z^2$, $Z^4$ and $Z^6$ represent $CH_3$.

In one particular embodiment of the invention, the at least one preferred compound of formula (II) as defined herein is one wherein:

- $Y^1$ and $Y^3$ represent N, $Y^2$ represents C; and
- R, T, U and V represent C; and
- $Z^2$, $Z^4$ and $Z^6$ represent a linear or branched, saturated or unsaturated $C_1$-$C_6$ alkyl, preferably $Z^2$, $Z^4$ and $Z^6$ represent $CH_3$; and
- $Z^1$ represents $X_1$—$R_3$—$X_2$—$P^+$, $X_1$—$R_3$—$P^+$, $X_1$—$X_2$—$P^+$, $R_3$—$X_2$—$P^+$, $X_1$—$P^+$, $R_3$—$P^+$, or $X_2$—$P^+$, preferably $X_1$—$R_3$—$X_2$—$P^+$, wherein $X_1$, $X_2$, $R_3$ and $P^+$ are as defined above; preferably $Z^1$ represents $X_1$—$R_3$—$X_2$—$P^+$, wherein $X_1$ represents $CH_2$, $X_2$ represents CO, and $R_3$ represents $(CH_2)_m$, with m representing an integer between 1 and 3, preferably m is equal to 2.

In one preferred embodiment of the invention, the at least one compound of formula (II) is a benzimidazole derivative, wherein:

$Y^1$ and $Y^3$ represent N, $Y^2$ represents C; and $Z^1$ or $Z^3$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined above; more preferably $Z^1$ or $Z^3$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2; and wherein:

(i) R, T, U and V represent C; preferably R, T, U and V represent C, and/or $Z^2$ represents H, $CH_3$, $SCH_3$, $CF_3$, phenyl, isopropyl, propyl, $CH_2—NH—CH_3$, $CH_2—O—CH_3$, or $CH_2—F$, and/or $Z^4$ represents H, $CH_3$, and/or $Z^5$ represents H, F, $OCH_3$, carboxyphenyl, tert-butyl, Cl, OH, or $CH_3$, and/or $Z^6$ represents H, $CH_3$, or F, and/or $Z^7$ represents H; or (ii) T and V represent N, and R and U represent C; preferably T and V represent N, and R and U represent C, and/or $Z^2$ represents H, $CH_3$, and/or $Z^4$ represents H, $NH_2$, $N(CH_3)_2$, and at least one of $Z^5$, $Z^6$ or $Z^7$ represents H; or (iii) R and U represent N, and T and V represent C; preferably R and U represent N, and T and V represent C, and/or $Z^2$ represents H, $CH_3$, and/or $Z^4$ represents H, $NH_2$, $N(CH_3)_2$, and at least one of $Z^5$, $Z^6$ or $Z^7$ represents H; or (iv) one of R, T, U or V represents N; preferably one of R, T, U or V represents N and at least one of $Z^2$, $Z^4$, $Z^5$, $Z^6$ or $Z^7$ represents H; or (v) R, T, U and V represent C, and $Z^5$ and $Z^6$ together form an optionally substituted naphtalene; preferably R, T, U and V represent C, $Z^5$ and $Z^6$ together form a naphtalene, and/or $Z^2$ represents $CH_3$, and/or $Z^4$ represents H, and/or $Z^7$ represents H.

Preferred benzimidazole derivatives according to the invention correspond to compounds 1.01 to 1.42, 1.51 to 1.72, 1.74 to 1.77 and 1.79 as disclosed in Table 1.

In another preferred embodiment of the invention, the at least one compound of formula (II) is a benzopyrazole derivative, wherein:

$Y^1$ and $Y^2$ represent N, $Y^3$ represents C; or $Y^2$ and $Y^3$ represent N, $Y^1$ represents C; and $Z^1$ or $Z^3$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined above; more preferably $Z^1$ or $Z^3$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2; and wherein:

(i) R, T, U and V represent C; preferably R, T, U and V represent C, and at least one of $Z^4$, $Z^5$, $Z^6$ or $Z^7$ represents H; or (ii) R, T, U and V, which may be identical or different, represent C or N, with the proviso that the six-membered ring contains no more than 1 N atom; preferably, one of R, U or V represents N and at least one of $Z^4$, $Z^5$, $Z^6$ or $Z^7$ represents H.

Preferred benzopyrazole derivatives according to the invention correspond to compounds 1.43 to 1.50 as disclosed in Table 1.

In another preferred embodiment of the invention, the at least one compound of formula (II) is a benzotriazole derivative, wherein:

$Y^1$, $Y^2$ and $Y^3$ represent N; and $Z^1$ or $Z^2$ represents $X_1—R_3—X_2—P^+$, $X_1—R_3—P^+$, $X_1—X_2—P^+$, $R_3—X_2—P^+$, $X_1—P^+$, $R_3—P^+$, or $X_2—P^+$, preferably $X_1—R_3—X_2—P^+$, wherein $X_1$, $X_2$, $R_3$ and $P^+$ are as defined above; more preferably $Z^1$ or $Z^2$ represents $X_1—R_3—X_2—P^+$, wherein $X_1$ represents $CH_2$, $X_2$ represents CO, and $R_3$ represents $(CH_2)_m$, with m representing an integer between 1 and 3, preferably m is equal to 2; and wherein:

(i) R, T, U and V represent C; preferably R, T, U and V represent C, and/or $Z^4$ represents H, and/or $Z^5$ represents H, $CH_3$, $OCH_3$, and/or $Z^6$ represents H, $CH_3$, and/or $Z^7$ represents H; or (ii) R, T, U and V, which may be identical or different, represent C or N, with the proviso that the six-membered ring contains no more than 1 N atom; preferably, one of R, T or U represents N and at least one of $Z^4$, $Z^5$, $Z^6$ or $Z^7$ represents H.

Preferred benzotriazole derivatives according to the invention correspond to compounds 2.01 to 2.18 as disclosed in Table 1.

According to a particular embodiment of the invention, preferred compounds of formula (II) correspond to compounds 1.01 to 1.72, 1.74 to 1.77 and 1.79, and compounds 2.01 to 2.18, more preferably compounds 1.42, 1.57 and 1.65, as disclosed in Table 1.

TABLE 1

Structures of preferred compounds of formula (II) of the invention.

| Compound | Structure | Polymer Molecular weight | Heterocycle Grafting |
|---|---|---|---|
| 1.01 | 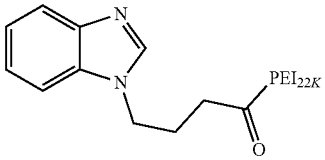 | 22k | 10% |

TABLE 1-continued
Structures of preferred compounds of formula (II) of the invention.
| Compound | Structure | Polymer Molecular weight | Heterocycle Grafting |
|---|---|---|---|
| 1.02 | 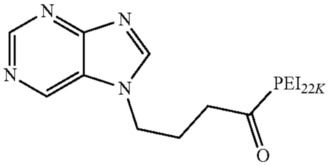 | 22k | 17% |
| 1.03 | 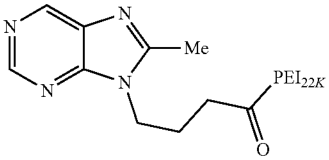 | 22k | 21% |
| 1.04 | 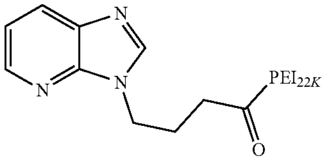 | 22k | 11% |
| 1.05 | 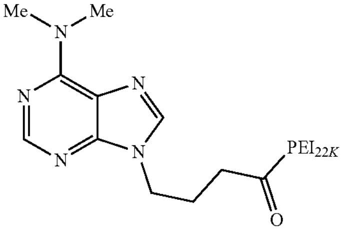 | 22k | 28% |
| 1.06 | 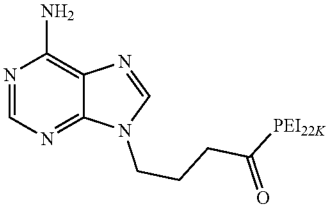 | 22k | 13% |
| 1.07 | 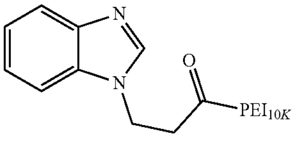 | 10k | 15% |
| 1.08 | 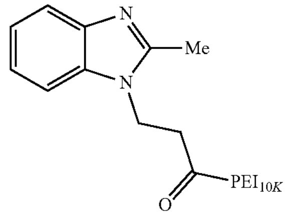 | 10k | 9% |

TABLE 1-continued
| Structures of preferred compounds of formula (II) of the invention. | | | |
|---|---|---|---|
| Compound | Structure | Polymer Molecular weight | Heterocycle Grafting |
| 1.09 | 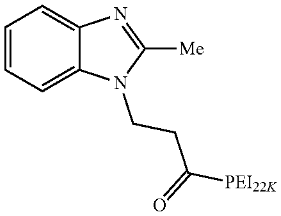 | 22k | 17% |
| 1.10 | 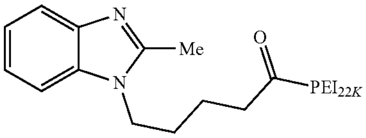 | 22k | 26% |
| 1.11 | 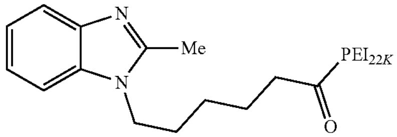 | 22k | 34% |
| 1.12 | 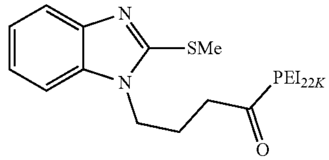 | 22k | 40% |
| 1.13 | 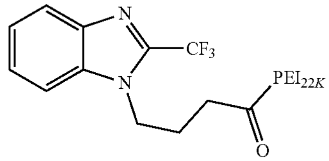 | 22k | 36% |
| 1.14 | 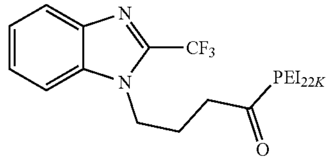 | 22k | 18% |
| 1.15 | 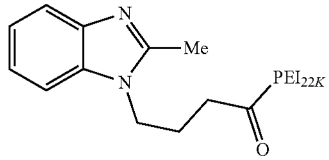 | 22k | 20% |
| 1.16 | 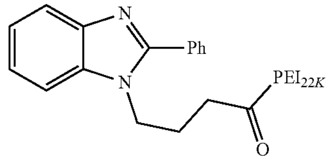 | 10k | 21% |

TABLE 1-continued
| Structures of preferred compounds of formula (II) of the invention. | | | |
|---|---|---|---|
| Compound | Structure | Polymer Molecular weight | Heterocycle Grafting |
| 1.17 | 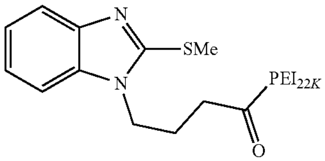 | 22k | 24% |
| 1.18 | 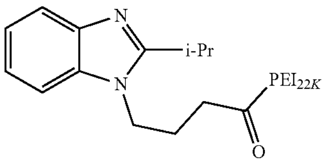 | 22k | 27% |
| 1.19 | 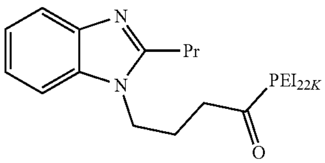 | 22k | 26% |
| 1.20 | 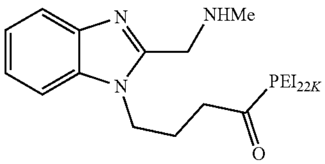 | 22k | 26% |
| 1.21 | 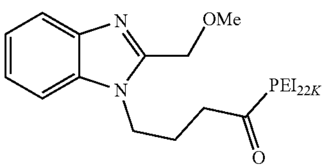 | 22k | 29% |
| 1.22 | 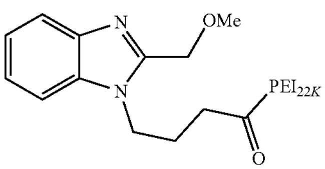 | 22k | 22% |
| 1.23 | 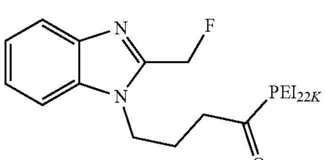 | 22k | 24% |
| 1.24 | 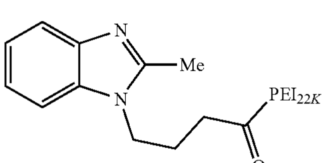 | 22k | 25% |

TABLE 1-continued
| Structures of preferred compounds of formula (II) of the invention. | | | |
|---|---|---|---|
| Compound | Structure | Polymer Molecular weight | Heterocycle Grafting |
| 1.25 | 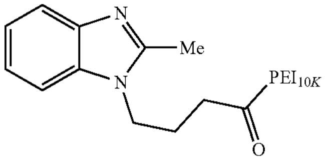 | 10k | 25% |
| 1.26 | 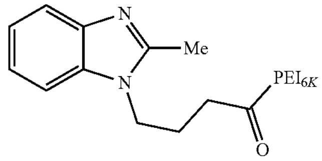 | 6k | 25% |
| 1.27 | 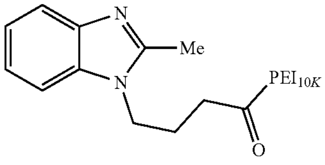 | 10k | 40% |
| 1.28 | 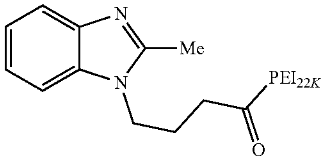 | 10k | 19% |
| 1.29 | 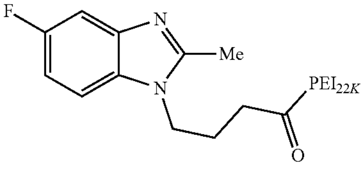 | 22k | 28% |
| 1.30 | 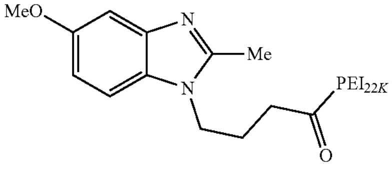 | 22k | 24% |
| 1.31 | 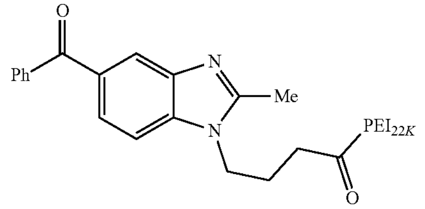 | 22k | 27% |
| 1.32 | 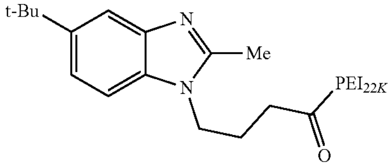 | 22k | 25% |

TABLE 1-continued
| Structures of preferred compounds of formula (II) of the invention. | | | |
|---|---|---|---|
| Compound | Structure | Polymer Molecular weight | Heterocycle Grafting |
| 1.33 | 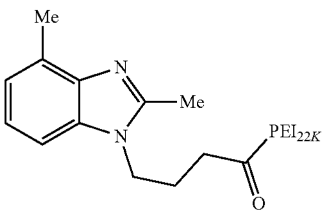 | 22k | 31% |
| 1.34 | 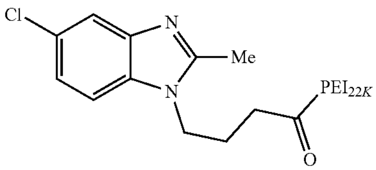 | 22k | 30% |
| 1.35 | 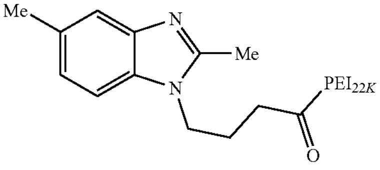 | 22k | 22% |
| 1.36 | 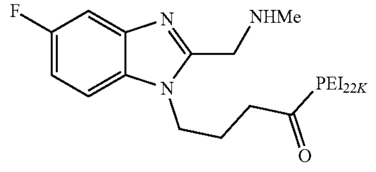 | 22k | 26% |
| 1.37 | 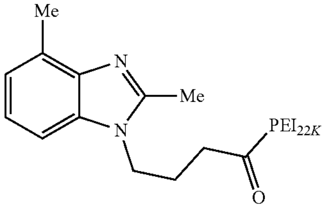 | 22k | 24% |
| 1.38 | 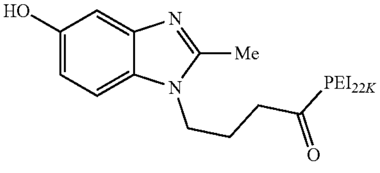 | 10k | 31% |
| 1.39 | 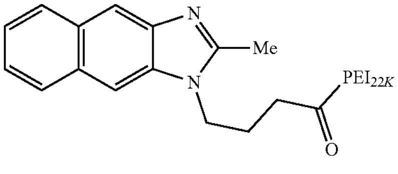 | 22k | 31% |
| 1.40 | 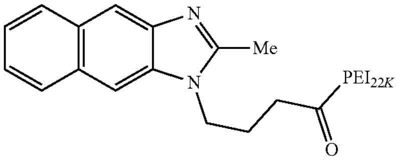 | 22k | 26% |

TABLE 1-continued
| Structures of preferred compounds of formula (II) of the invention. | | | |
|---|---|---|---|
| Compound | Structure | Polymer Molecular weight | Heterocycle Grafting |
| 1.41 | 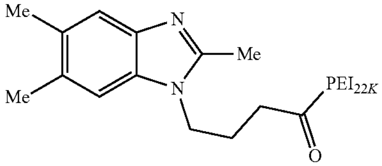 | 22k | 22% |
| 1.42 | 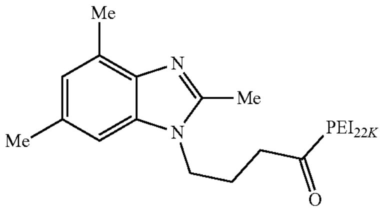 | 22k | 22% |
| 1.43 | 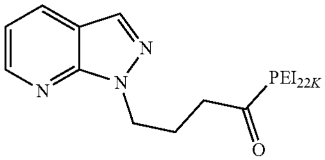 | 22K | 55% |
| 1.44 | 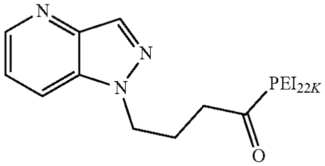 | 22K | 47% |
| 1.45 | 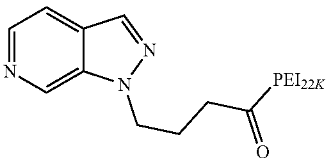 | 22K | 25% |
| 1.46 | 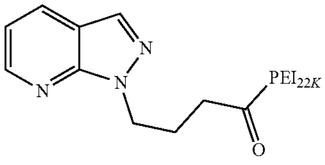 | 22K | 22% |
| 1.47 | 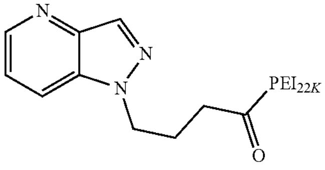 | 22K | 21% |
| 1.48 | 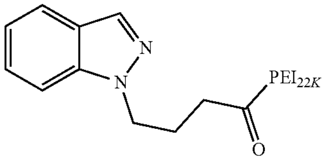 | 22k | 9% |

TABLE 1-continued
| Compound | Structure | Polymer Molecular weight | Heterocycle Grafting |
|---|---|---|---|
| Structures of preferred compounds of formula (II) of the invention. | | | |
| 1.49 | 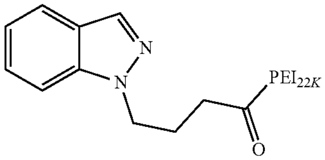 | 22k | 21% |
| 1.50 | 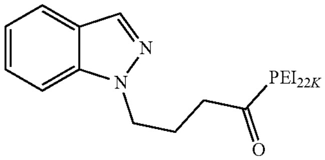 | 22k | 24% |
| 1.51 | 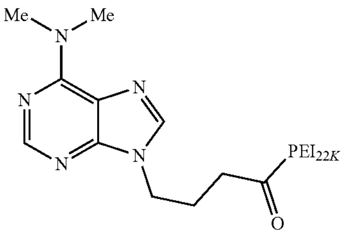 | 22k | 13% |
| 1.52 | 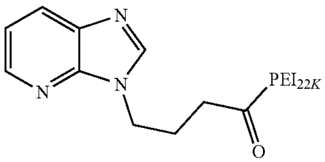 | 22k | 27% |
| 1.53 | 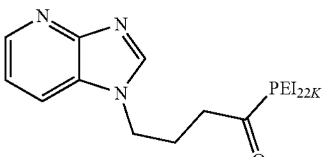 | 22k | 22% |
| 1.54 | 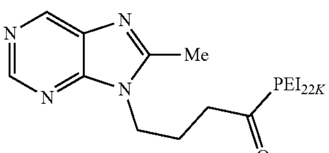 | 22k | 17% |
| 1.55 | 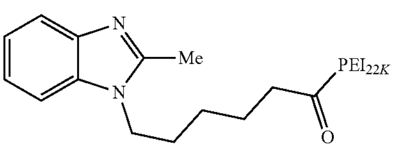 | 22k | 26% |
| 1.56 | 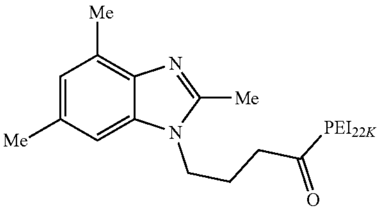 | 22k | 30% |

TABLE 1-continued
Structures of preferred compounds of formula (II) of the invention.
| Compound | Structure | Polymer Molecular weight | Heterocycle Grafting |
|---|---|---|---|
| 1.57 | 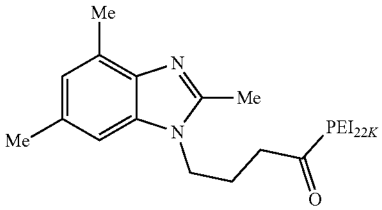 | 22k | 7% |
| 1.58 | 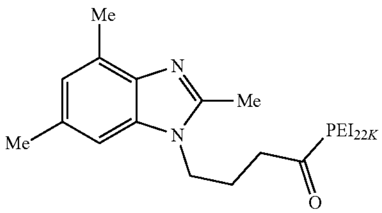 | 22k | 11% |
| 1.59 | 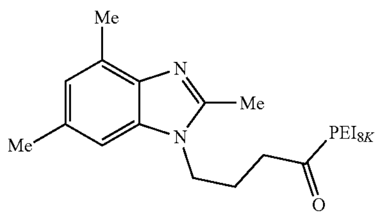 | 8k | 20% |
| 1.60 | 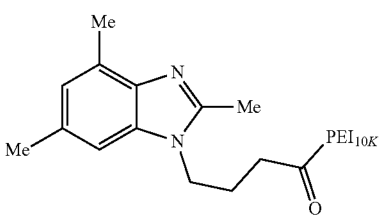 | 10k | 20% |
| 1.61 | 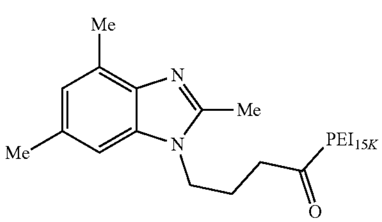 | 15k | 17% |
| 1.62 | 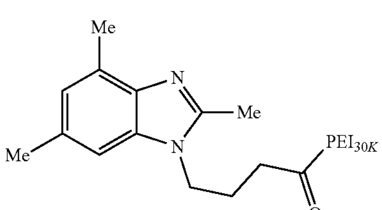 | 30k | 18% |

TABLE 1-continued
| Structures of preferred compounds of formula (II) of the invention. | | | |
|---|---|---|---|
| Compound | Structure | Polymer Molecular weight | Heterocycle Grafting |
| 1.63 | 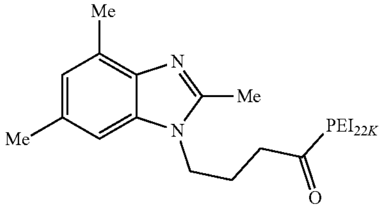 | 22k | 30% |
| 1.64 | 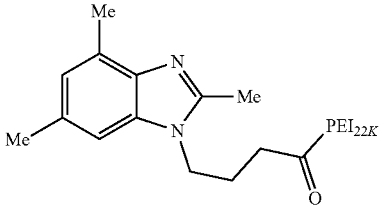 | 22k | 14% |
| 1.65 | 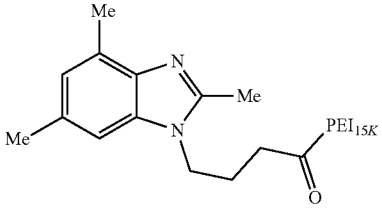 | 15k | 23% |
| 1.66 | 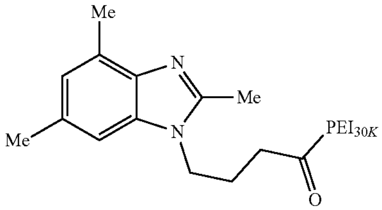 | 30k | 21% |
| 1.67 | 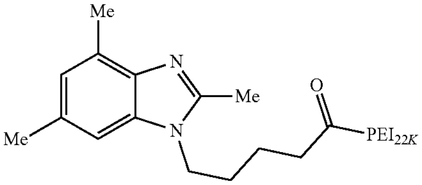 | 22k | 19% |
| 1.68 | 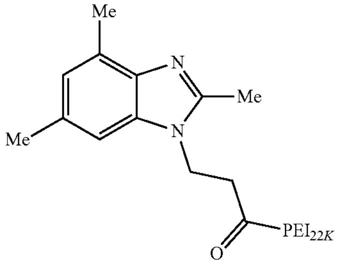 | 22k | 21% |

TABLE 1-continued
| Structures of preferred compounds of formula (II) of the invention. | | | |
|---|---|---|---|
| Compound | Structure | Polymer Molecular weight | Heterocycle Grafting |
| 1.69 | 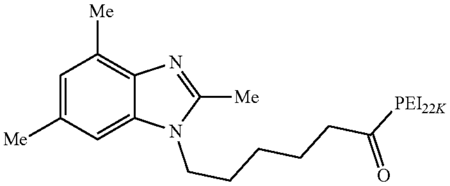 | 22k | 32% |
| 1.70 | 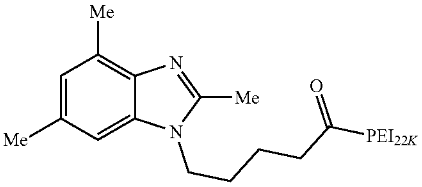 | 22k | 20% |
| 1.71 | 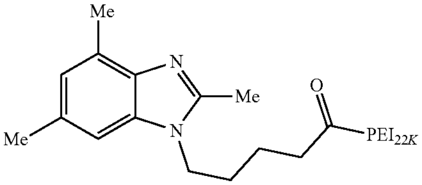 | 22k | 25% |
| 1.72 | 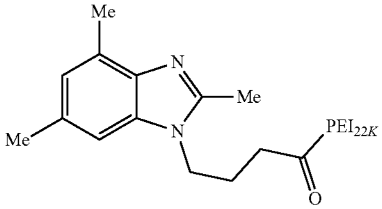 | 22k | 26% |
| 1.74 | 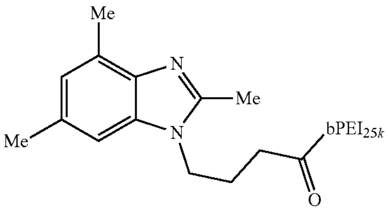 | 25k | 22% |
| 1.75 | 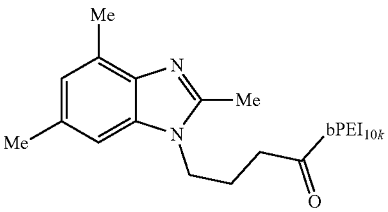 | 10k | 29% |
| 1.76 | 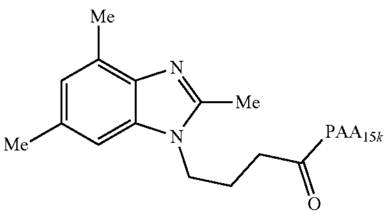 | 15k | 19% |

TABLE 1-continued
Structures of preferred compounds of formula (II) of the invention.
| Compound | Structure | Polymer Molecular weight | Heterocycle Grafting |
|---|---|---|---|
| 1.77 | 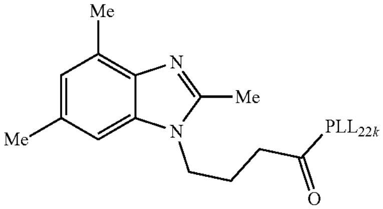 | 22k | 27% |
| 1.79 | 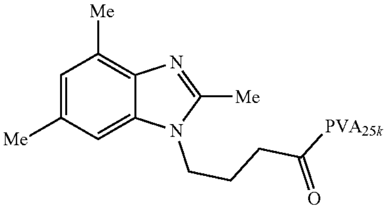 | 25k | 27% |
| 2.01 | 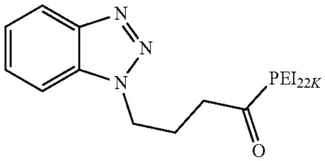 | 22k | 35% |
| 2.02 | 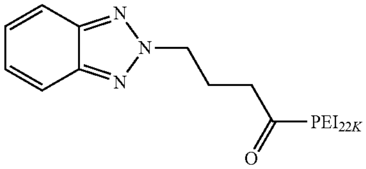 | 22k | 35% |
| 2.03 | 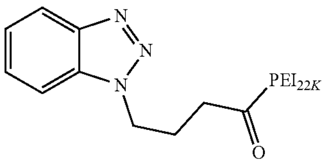 | 22k | 23% |
| 2.04 | 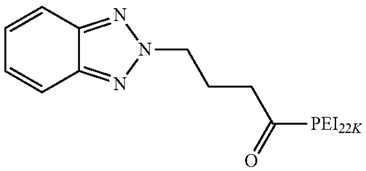 | 22k | 23% |
| 2.05 | 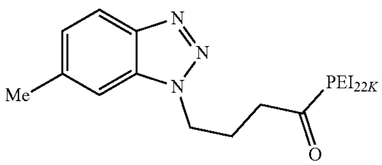 | 22k | 23% |
| 2.06 | 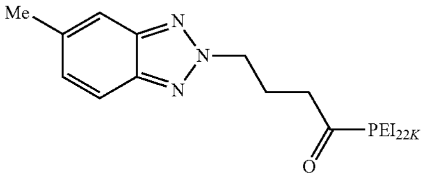 | 22k | 24% |

TABLE 1-continued
| Structures of preferred compounds of formula (II) of the invention. | | | |
|---|---|---|---|
| Compound | Structure | Polymer Molecular weight | Heterocycle Grafting |
| 2.07 | 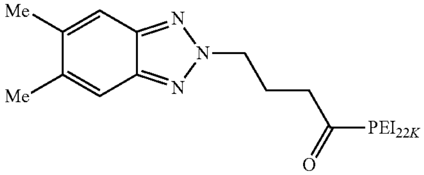 | 22k | 22% |
| 2.08 | 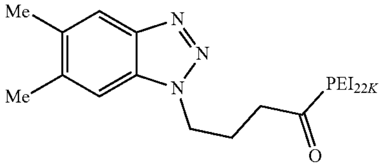 | 22k | 22% |
| 2.09 | 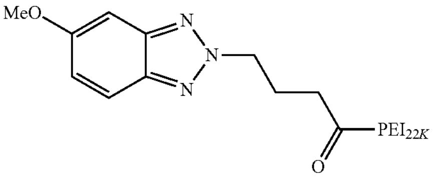 | 22k | 23% |
| 2.10 | 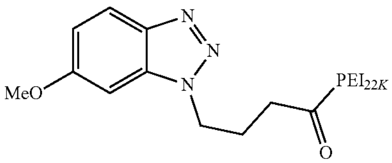 | 22k | 22% |
| 2.11 | 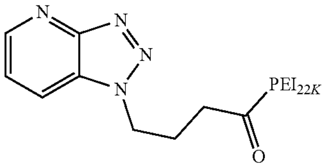 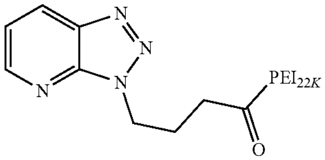 | 22k | 22% |
| 2.12 | 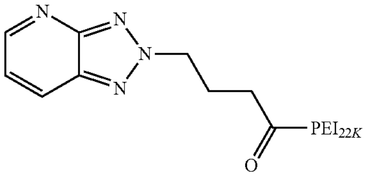 | 22k | 18% |
| 2.13 | 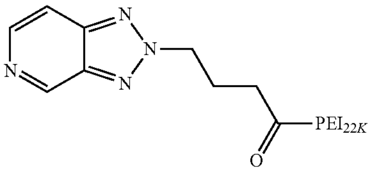 | 22k | 15% |

TABLE 1-continued
| Compound | Structure | Polymer Molecular weight | Heterocycle Grafting |
| --- | --- | --- | --- |
| Structures of preferred compounds of formula (II) of the invention. | | | |
| 2.14 | 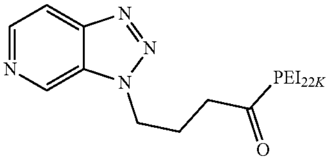 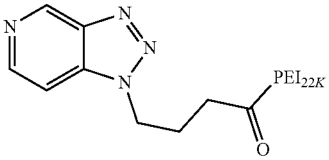 | 22K | 17% |
| 2.15 | 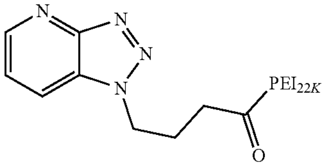 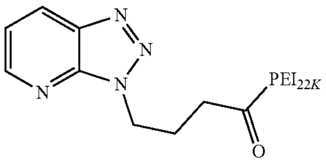 | 22K | 28% |
| 2.16 | 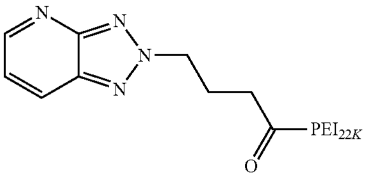 | 22K | 34% |
| 2.17 | 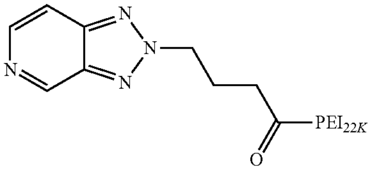 | 22K | 28% |
| 2.18 | 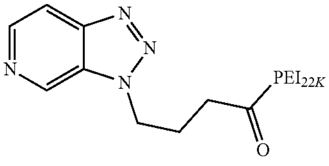 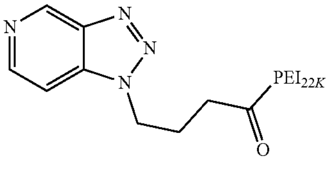 | 22K | 27% |

Thus, in a particular embodiment of the invention, the at least one compound of general formula (II) is selected from the group consisting of the following compounds:
1.01
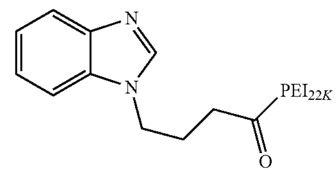
1.02
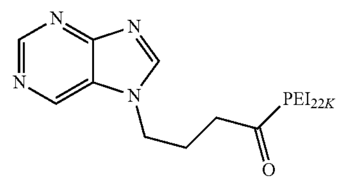
1.03
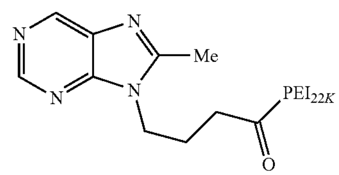
1.04
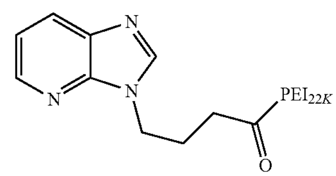
1.05
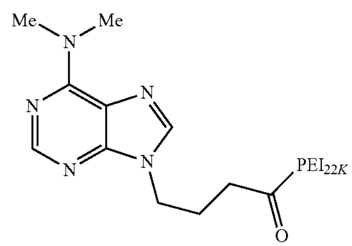
1.06
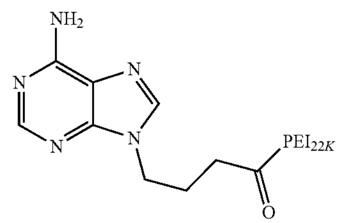
1.07
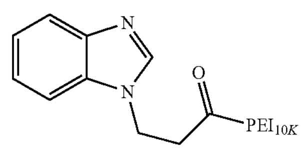
-continued
1.08
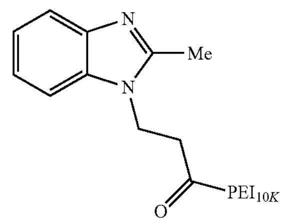
1.09
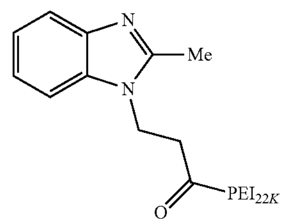
1.10
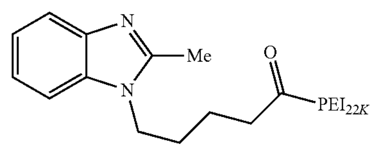
1.11
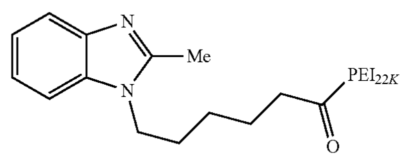
1.12
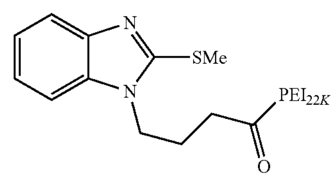
1.13
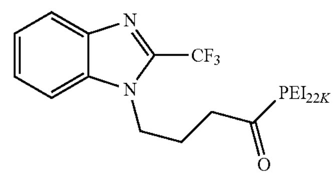
1.14
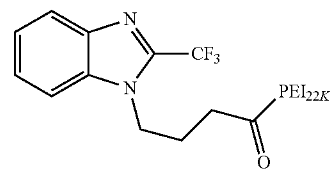
1.15
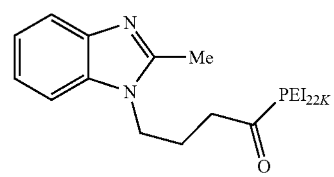

-continued
1.16
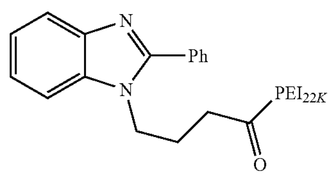
1.17
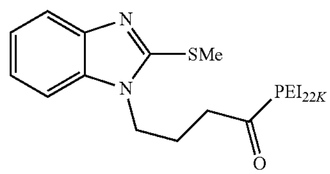
1.18
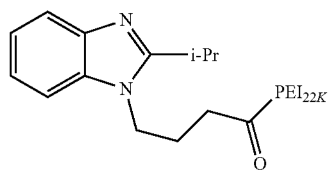
1.19
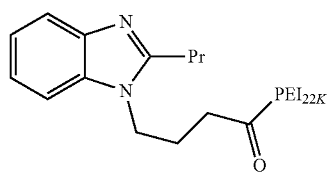
1.20
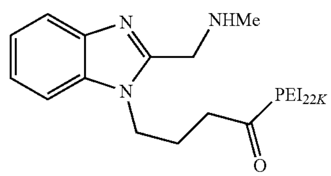
1.21
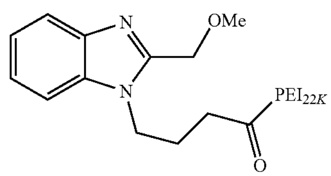
1.22
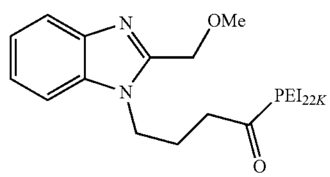
1.23
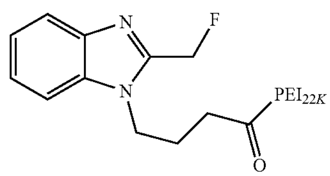
1.24
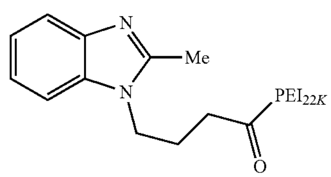
-continued
1.25
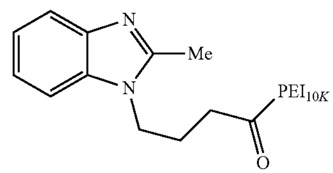
1.26
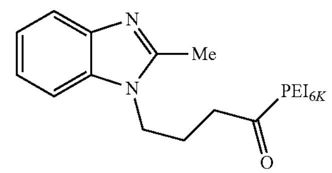
1.27
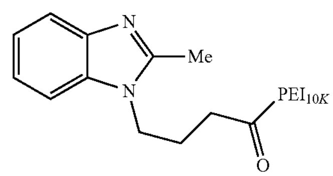
1.28
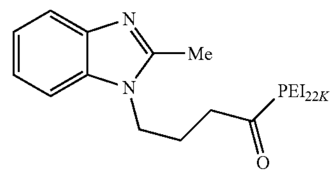
1.29
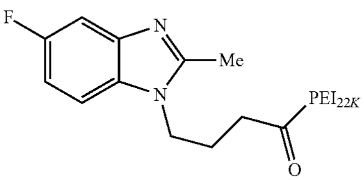
1.30
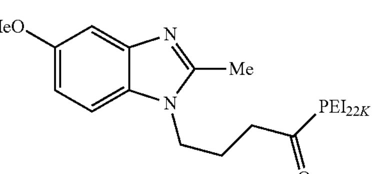
1.31
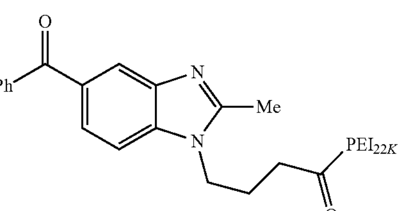
1.32
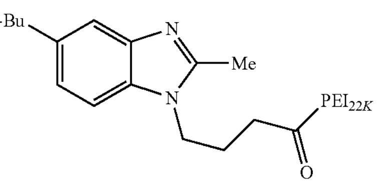
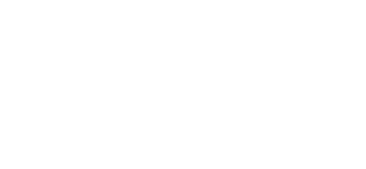

-continued
1.33
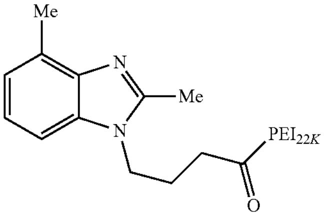
1.34
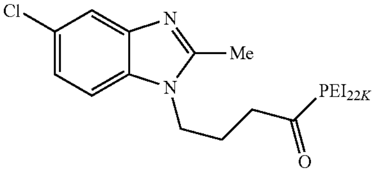
1.35
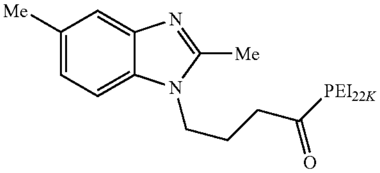
1.36
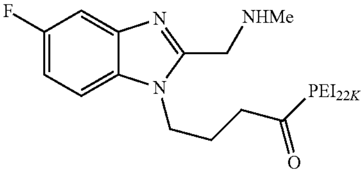
1.37
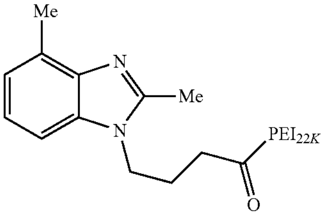
1.38
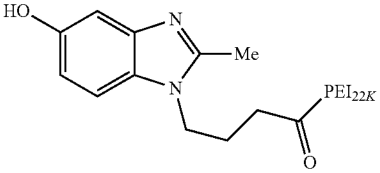
1.39
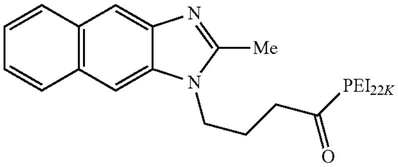
1.40
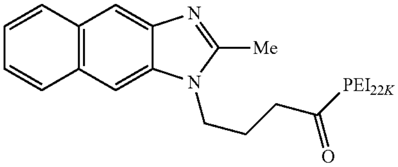
-continued
1.41
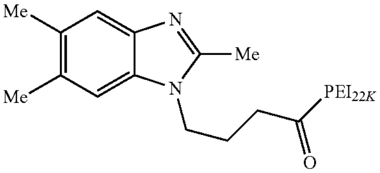
1.42
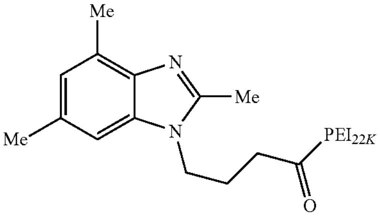
1.43
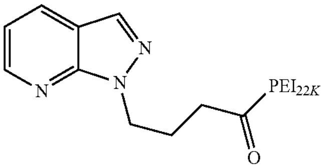
1.44
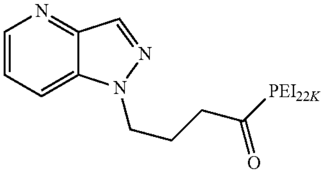
1.45
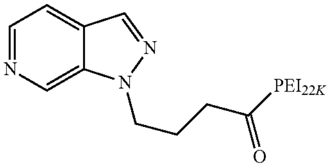
1.46
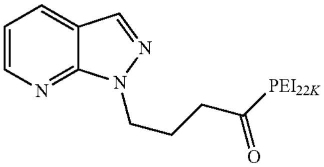
1.47
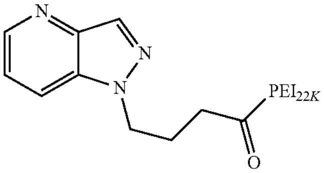
1.48
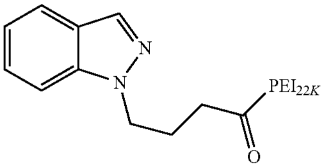

-continued
1.49
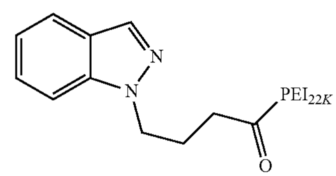
1.50
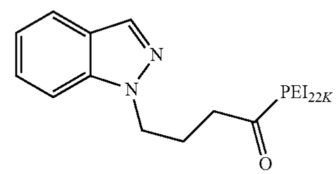
1.51
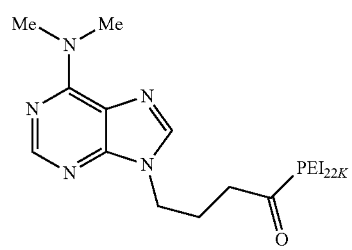
1.52
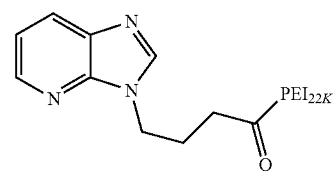
1.53
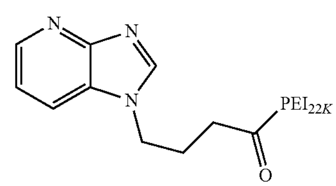
1.54
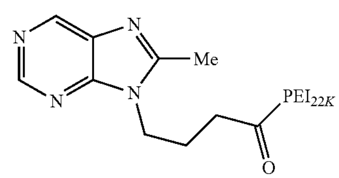
1.55
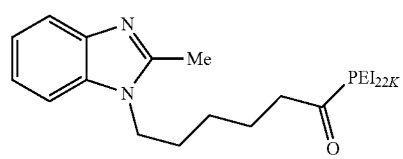
1.56
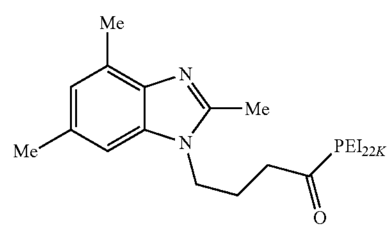
-continued
1.57
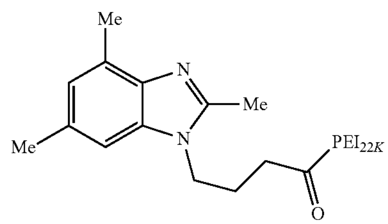
1.58
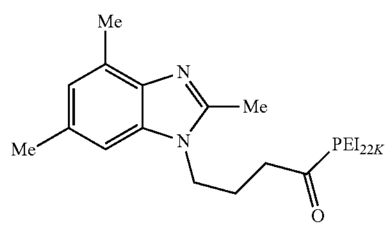
1.59
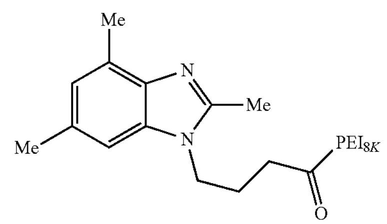
1.60
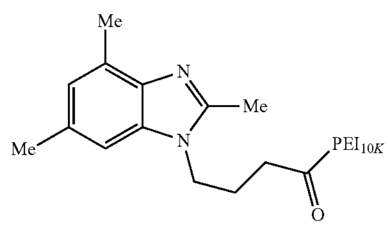
1.61
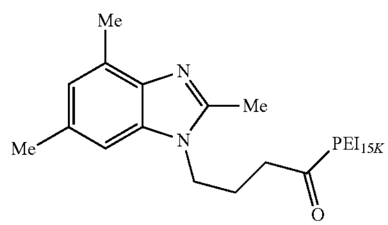
1.62
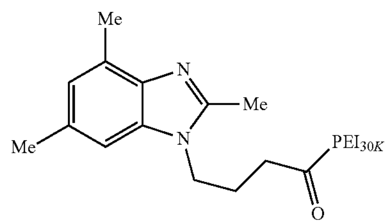
1.63
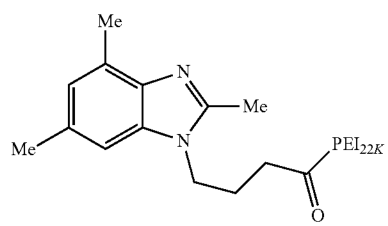

1.64
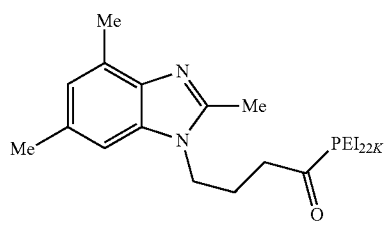
1.65
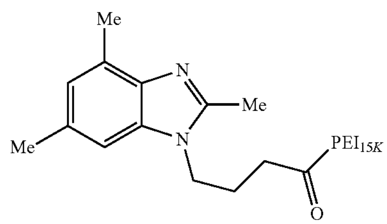
1.66
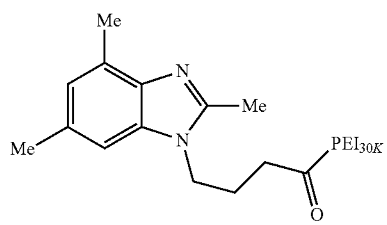
1.67
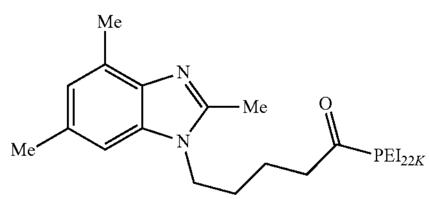
1.68
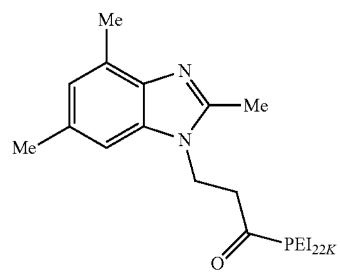
1.69
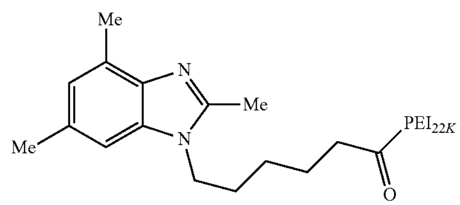
1.70
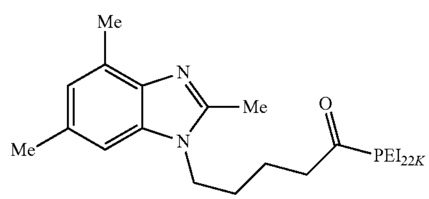
1.71
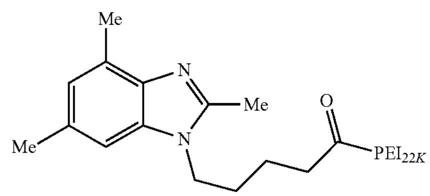
1.72
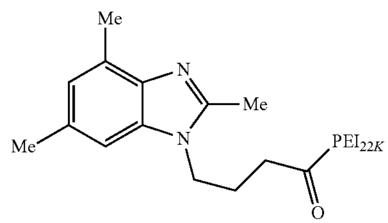
1.74
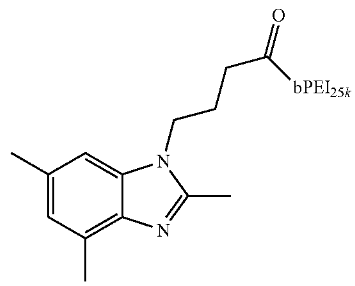
1.75
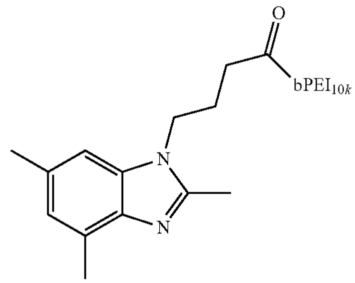
1.76
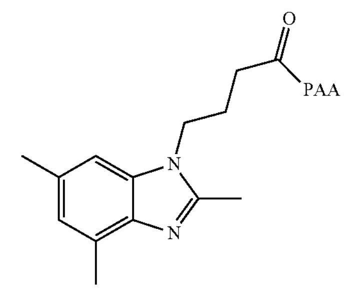
1.77
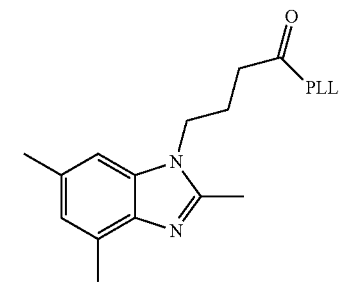

-continued
1.79
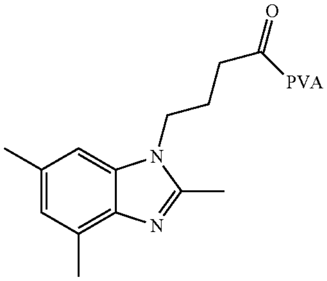
2.01
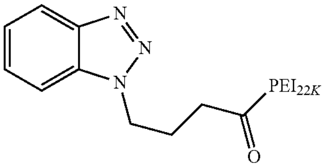
2.02
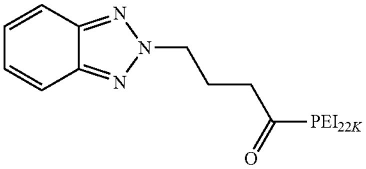
2.03
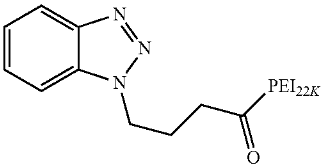
2.04
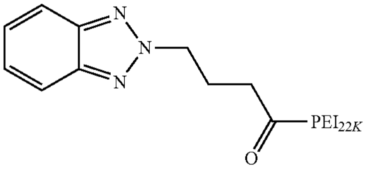
2.05
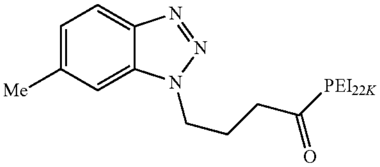
2.06
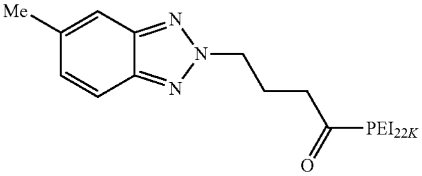
2.07
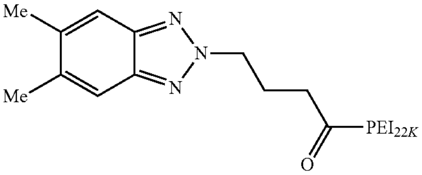
-continued
2.08
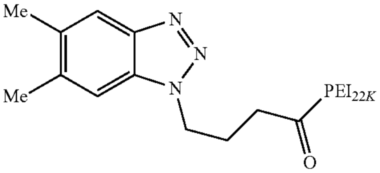
2.09
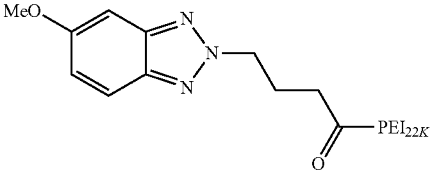
2.10
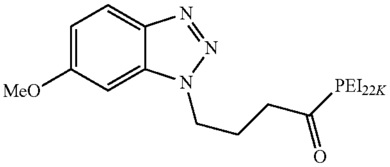
2.11
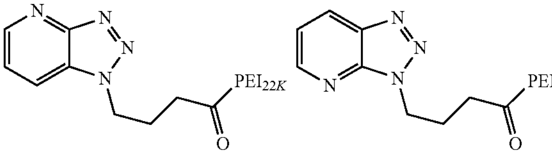
2.12
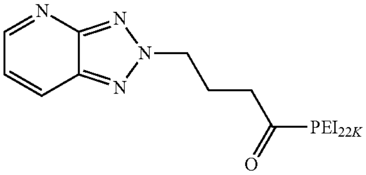
2.13
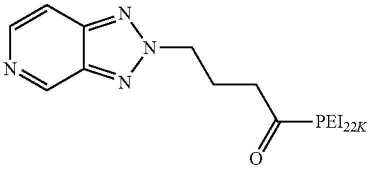
2.14
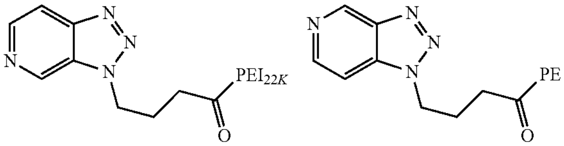
2.15
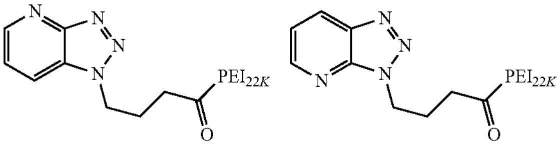
2.16
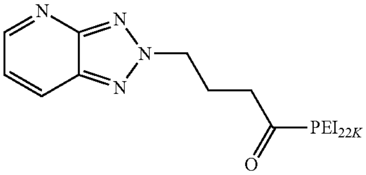

-continued
2.17
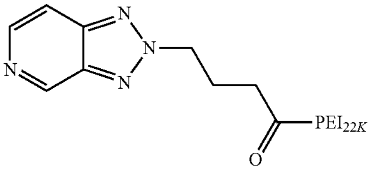
2.18
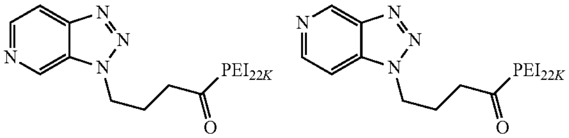
1.43
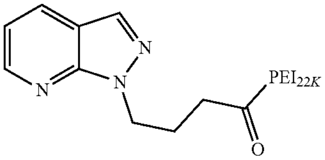
1.44
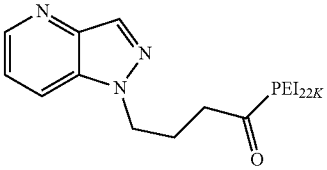
1.45
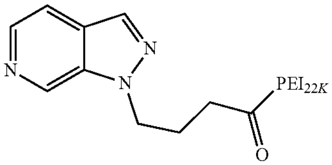
1.46
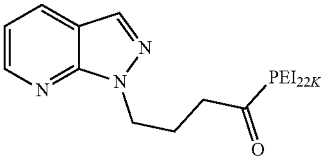
1.47
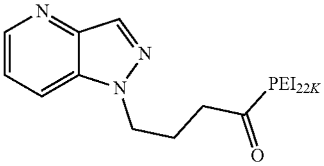
1.48
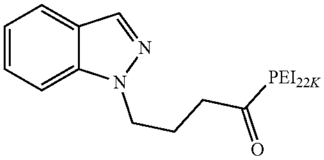
-continued
1.49
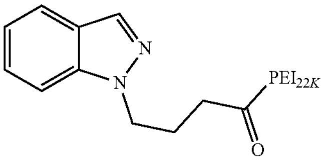
1.50
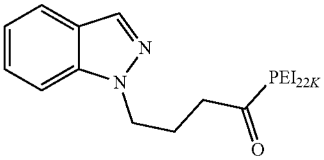
1.51
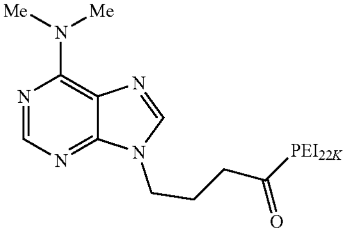
1.52
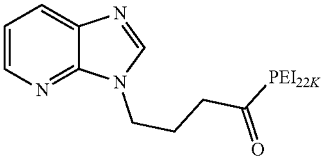
1.53
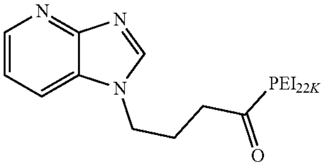
1.54
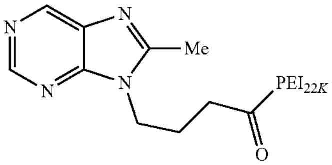
1.55
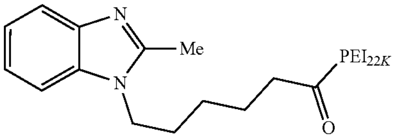
1.56
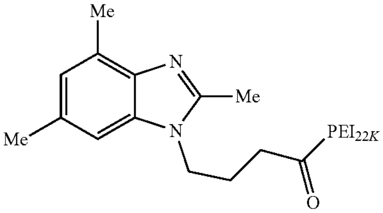

1.57
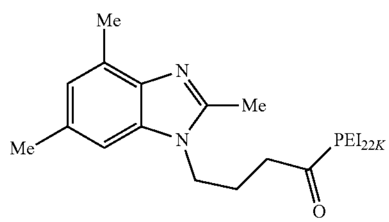
1.58
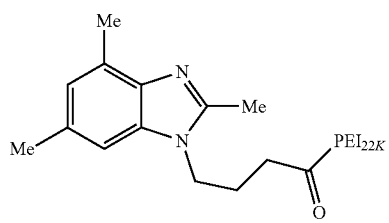
1.59
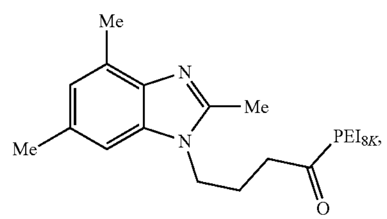
1.60
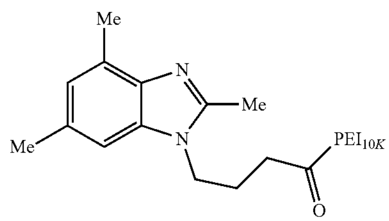
1.61
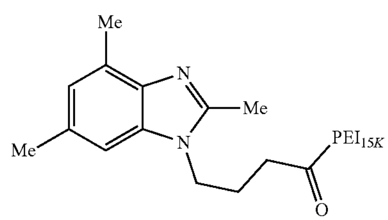
1.62
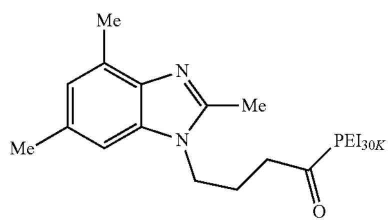
1.63
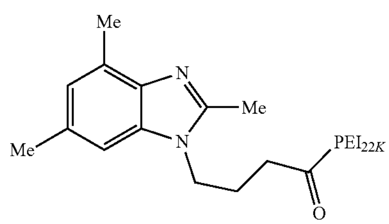
1.64
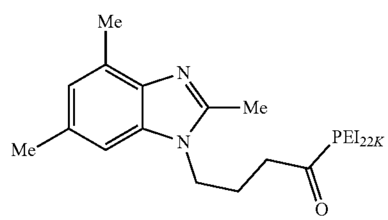
1.65
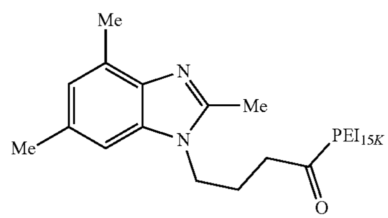
1.66
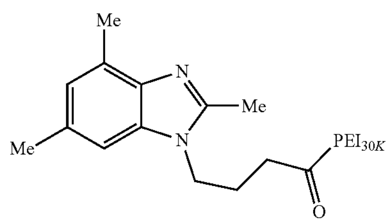
1.67
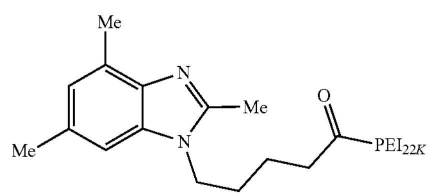
1.68
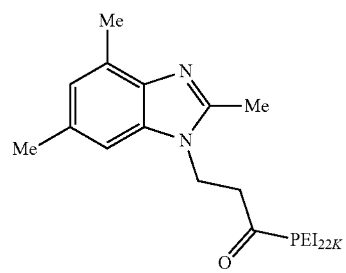
1.69
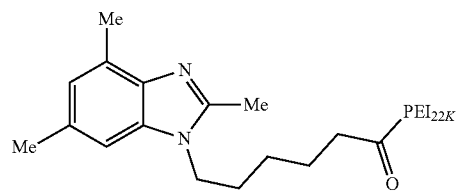
1.70
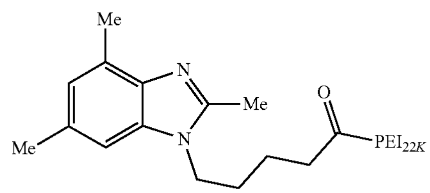

-continued
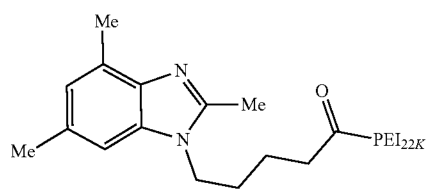
1.71
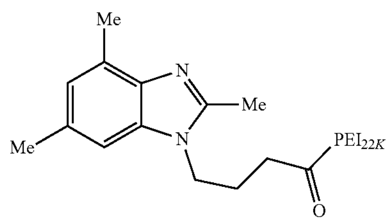
1.72
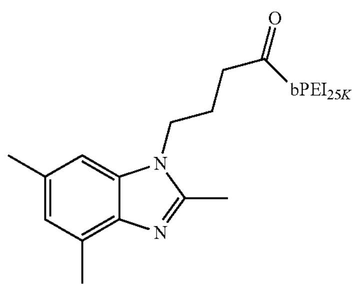
1.74
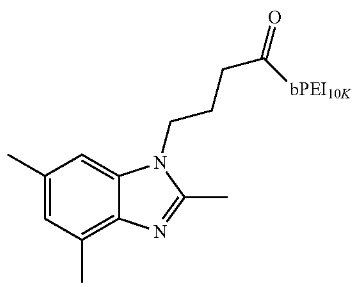
1.75
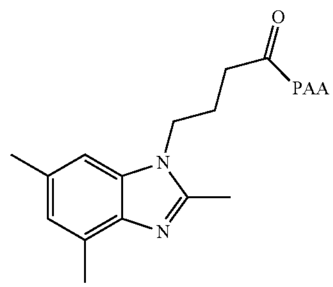
1.76
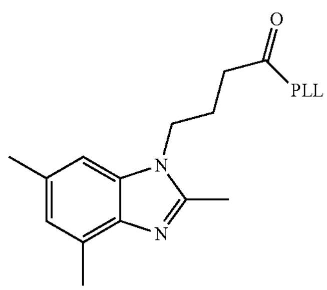
1.77
-continued
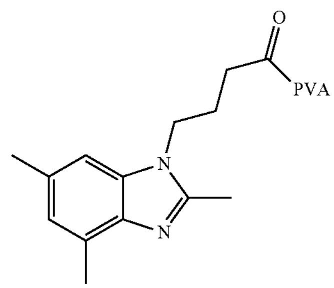
1.79
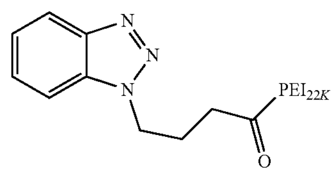
2.01
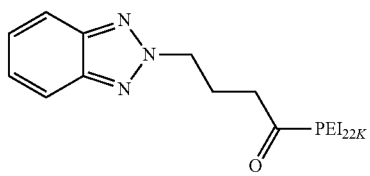
2.02
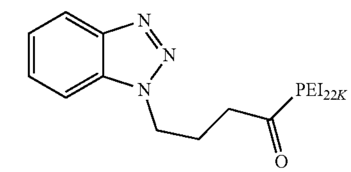
2.03
2.04
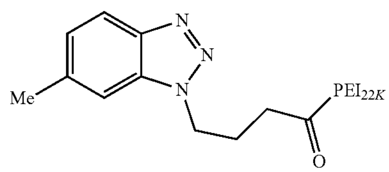
2.05
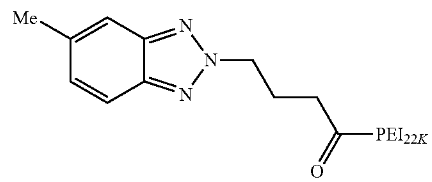
2.06
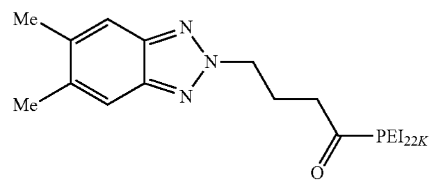
2.07

-continued 2.08

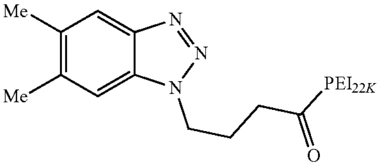

2.09

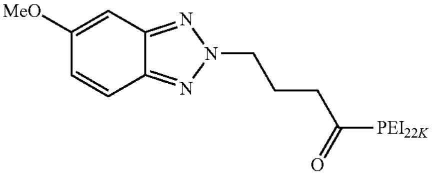

2.10

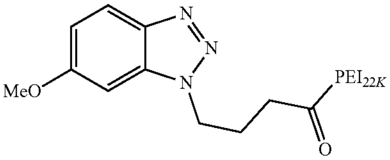

2.11

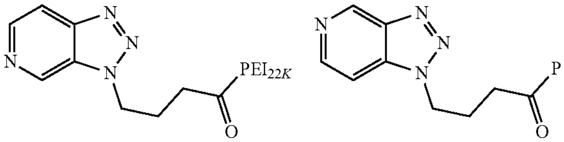

2.12

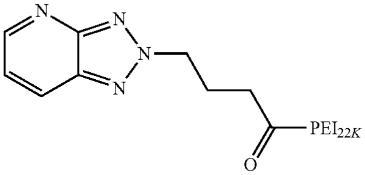

2.13

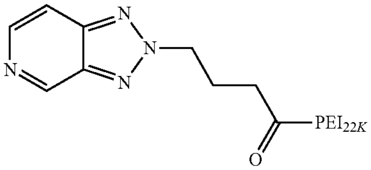

2.14

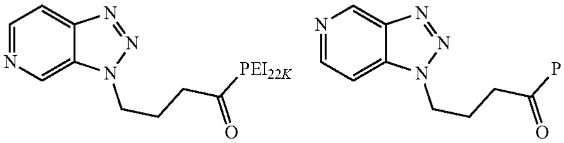

2.15

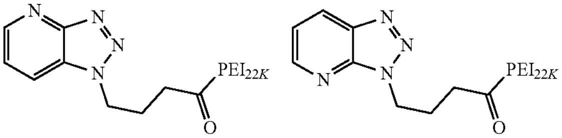

2.16

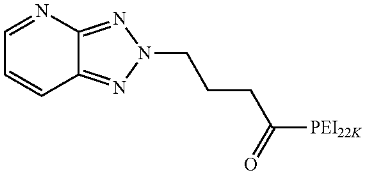

-continued 2.17

2.18

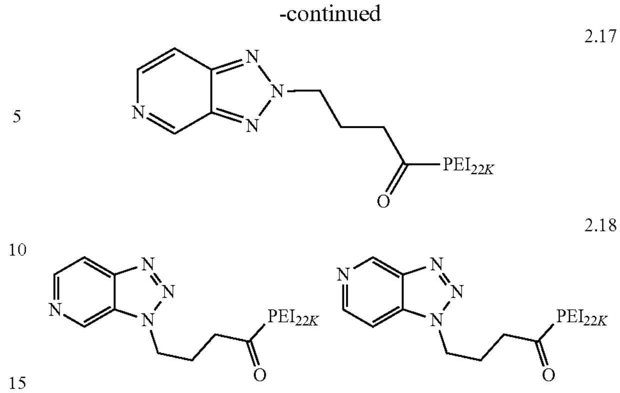

In a preferred embodiment of the invention, the at least one compound of general formula (II) is selected from the group consisting of the following compounds: 1.09, 1.10, 1.11, 1.14, 1.15, 1.17, 1.18, 1.19, 1.20, 1.25, 1.27, 1.28, 1.30, 1.35, 1.36, 1.37, 1.41, 1.42, 1.57, 1.60, 1.65, 2.03, 2.04, 2.05, 2.08, 2.09 and 2.10.

The at least one compound of general formula (II) may be prepared according to various methods well known in the art.

The present invention is also directed to the composition according to the invention for use in in vivo applications for cell transformation by uptake of exogenous nucleic acid using the composition of the invention, for cell therapy or for gene therapy. The cells may be eukaryotic cells, in particular mammalian cells, especially human cells, in particular primary cells, either dividing or non-dividing cells.

The present invention also concerns a method for in vitro or ex vivo transfection of live cells comprising introducing in the cells the composition according to the invention. Said live cells may be provided or maintained in medium containing serum, synthetic medium, animal-free component medium or chemically defined medium.

The present invention also relates to the in vitro or ex vivo use of the composition according to the invention to transfect at least one nucleic acid molecule into a cell, cell line or cells, preferably a cell, cell line or cells selected from the group consisting of a mammalian cell, an insect cell, a primary cell, an adherent cell, a suspension cell, a dividing cell such as a stem cell, a non-dividing cell such as a neuronal cell, and a cancer cell, said cell, cell line or cells being optionally organized into spheroids, organoids, 2D or 3D cell culture, or provided as fibre or matrix culture, and/or within a bioreactor.

As defined herein, the term "adherent cells" refers to cells that need solid support for growth, and are thus anchorage-dependent. Examples of adherent cells include, but are not limited to, MRC-5 cells, Hela cells, Vero cells, NIH-3T3 cells, L293 cells, CHO cells, BHK-21 cells, MCF-7 cells, A549 cells, COS cells, HEK 293 cells, Hep G2 cells, SNN-BE (2) cells, BAE-1 cells or SH-SY5Y cells.

As defined herein, the term "suspension cells" refers to cells that do not need solid support for growth, and are thus anchorage-independent. Examples of suspension cells include, but are not limited to, NSO cells, U937 cells, Namalawa cells, HL60 cells, WEHI231 cells, Yac 1 cells, Jurkat cells, THP-1 cells, K562 cells or U266B1 cells.

As defined herein, the term "spheroids" refers to spherical, heterogenous aggregates of cells in culture that retain three-dimensional architecture.

As defined herein, the term "organoids" refers to three-dimensional structures made of collection of organ-specific cell types self-organized in a manner similar to in vivo.

As defined herein, the term "fibre or matrix culture" refers to three-dimensional cell culture support composed of insoluble elastic fibers or extracellular proteins self-organized into matrix.

Said transfection may be stable or transient, standard or reverse.

As disclosed herein, the composition according to the invention may comprise multiple distinct nucleic acids, in particular selected from the group consisting of multiple plasmid DNA, plasmid DNA and oligonucleotide, plasmid DNA and mRNA for co-transfection.

Said at least one nucleic acid molecule to be transfected may be a gene encoding a protein, a protein fragment, a peptide or an antibody or functional antigen-binding regions thereof, in particular VH and/or VL chains thereof. Said protein may be selected from the group consisting of a reporter protein, a fluorescent protein, an enzyme, a structural protein, a receptor, a transmembrane protein, a therapeutic protein, a cytokine, a toxin, an oncogenic protein, an anti-oncogene, a pro-apoptotic protein, an anti-apoptotic protein, a polymerase, a transcription factor and a capsid protein.

The present invention also relates to the in vitro or ex vivo use of the composition according to the invention for genome engineering, for cell reprogramming, in particular for the reprogramming of differentiated cells into induced pluripotent stem cells (iPCs), for differentiating cells, or for gene-editing. Such use may be carried out in a culture of cells in vitro or ex vivo for the production of biologics, for the preparation of cells for therapy purpose, or for the study of cell functions or behaviour in particular with a step of expansion of cells after their transfection or may be carried out in vivo for a therapeutic purpose in a host in need thereof.

The present invention also relates to the in vitro or ex vivo use of the composition according to the invention (i) in the production of biologics, in particular biologics encoding a recombinant protein, peptide or antibody; or (ii) in the production of recombinant virus, such as adeno-associated virus (AAV), lentivirus (LV), adenovirus, oncolytic virus, or baculovirus, said composition comprising multiple nucleic acid molecules for co-transfection such as a plurality of plasmids; or (iii) in the production of viral or virus-like particles, said composition comprising multiple nucleic acid molecules for co-transfection such as a plurality of plasmids.

Thus the present invention also relates to a method for the production of (i) biologics, in particular biologics encoding a recombinant protein, peptide or antibody; or (ii) recombinant virus, such as adeno-associated virus (AAV), lentivirus (LV), adenovirus, oncolytic virus, or baculovirus, wherein the composition according to the invention comprises multiple nucleic acid molecules for co-transfection; or (iii) viral or virus-like particles, wherein the composition according to the invention comprises multiple nucleic acid molecules for co-transfection. As defined herein, the term "biologics" refers to proteins or nucleic acids or combinations thereof, living entities such as cells or viruses, cell compartments, organoids, and tissues.

In a particular embodiment of the invention, said method is for the production of AAV or LV, and said composition comprises (i) at least the compound 1.42, and (ii) an acceptable excipient, buffering agent, cell culture medium, or transfection medium.

In a particular embodiment of the invention, said method is for the production of LV, and said composition comprises (i) at least the compound 1.57, and (ii) an acceptable excipient, buffering agent, cell culture medium, or transfection medium.

In a particular embodiment of the invention, said in vitro or ex vivo use of the composition according to the invention or said method is for the production of recombinant virus, said composition comprising a plurality of expression vectors such as plasmid vectors to transfect in an adherent or suspension cell, such as HEK293 and derivative cells, HeLa, BHK-21, A549 or insect cells, wherein said vectors, in particular plasmids, are construct expressing viral structural sequences and transfer vector genome for virus or virus-like production and optionally expressing molecules of interest encoded by the transfer vector genome.

In a particular embodiment of the invention, said recombinant virus is for use in in vivo applications for cell therapy or for gene therapy.

In a particular embodiment of the invention, the invention relates to the in vitro or ex vivo use of the composition according to the invention to transfect at least one nucleic acid molecule into a stem cell, said composition comprising (i) the compound 1.42, and (ii) an acceptable excipient, buffering agent, cell culture medium, or transfection medium.

In a particular embodiment of the invention, the invention relates to the in vitro or ex vivo use of the composition according to the invention to transfect at least one nucleic acid molecule into a neuronal cell, said composition comprising (i) the compound 1.65 or the compound 1.60, and (ii) an acceptable excipient, buffering agent, cell culture medium, or transfection medium.

In a particular embodiment of the invention, the invention relates to the in vitro or ex vivo use of the composition according to the invention in the production of a recombinant virus, such as an adeno-associated virus (AAV) or a lentivirus (LV), said composition comprising (i) at least one compound selected from the group of compounds 1.42 and 1.57, and (ii) an acceptable excipient, buffering agent, cell culture medium, or transfection medium. Preferably, a composition comprising the compound 1.42 is used in the production of AAV; a composition comprising one compound selected from the group consisting of compounds 1.42 and 1.57 is used in the production of LV.

Unless otherwise stated, all the above-mentioned embodiments may be combined together. Thus features which are described in the context of separate embodiments may be combined in a single embodiment.

Other features and advantages of the invention will be apparent from the examples which follow and will also be illustrated in the figures.

BRIEF DESCRIPTION OF THE FIGURES

FIG. 1. Percentage of GFP expression after transfection of Caco-2, Hep G2, MDCK and MCF-10A with compounds of Example 3. The ratio 1:3 and 1:4 indicate the ratio of μg of DNA per μL of compound.

FIG. 2. Percentage of GFP expression after transfection of Caco-2, Hep G2, MDCK and MCF-10A with compounds of Example 4. The ratio 1:3 and 1:4 indicate the ratio of μg of DNA per μL of compound.

FIG. 5. Transfection of Primary rat cortex neurons (RCN) and primary rat hippocampal neurons (RHN).

FIG. 6. Production of AAV-2 from suspension HEK-293T cells. AAV-2 vectors expressing the GFP reporter gene were produced in HEK-293T cells grown in suspension in FreeStyle F17 media (a chemically defined, protein-free, serum-free expression medium for suspension HEK293 and CHO cells). Cells were seeded and cultured for 3 days before being transfected by 3 plasmids (pAAV-RC2 vector expressing Rep and Cap, pHelper vector expressing Adeno E2A, Adeno E4 and Adeno VA helper factors, and pAAV-GFP control vector expressing the GFP under the control of a CMV promoter) with PElpro® (a linear polyethylenimine DNA transfection reagent, Polyplus-transfection) or various compounds at ratio 1:2 or 1:3 μg DNA/μL reagent. AAV titers (transducing unit, TU/mL) were determined 72 hours post-transfection. The results are expressed as relative AAV-2 transducing Units/mL (TU/mL) in comparison to PElpro® transfection at ratio 1:2 and 1:3.

FIG. 7. Production of lentivirus particles from suspension HEK-293T cells. Lentivirus expressing the GFP reporter gene was produced in HEK-293Tcells grown in suspension in FreeStyle F17 media. Cells were seeded and cultured for 3 days before being transfected by 4 plasmids with PElpro® or various compounds at ratio 1:2 μg total DNA/μL reagent. Lentivirus titers (transducing unit, TU/mL) were determined 72 hours post-transfection.

FIG. 8. Gel electrophoresis showing genome editing in HEK293 cells after transfection of plasmid CRISPR Cas9 targeting the HRPT-1 gene (plasmid p38285) with compound 1.42. Two days after the transfection, the genomic DNA was extracted and the targeted HPRT-1 focus was amplified by PCR. After digestion by the T7 endonuclease I, the PCR products were run on a 2% agarose gel and stained with ethidium bromide. Cas9-induced cleavage HPTR-1 bands (650 and 430 bp) and the uncleaved HPTR-1 band (1083 bp) were visualized and quantifed on the gel, then the genome editing efficiency was determined (INDEL %). The INDEL % was 33.48+/−7.08% for the plasmid p38285, where no INDEL event was detected with the plasmid pCONTROL.

FIG. 9. Transfection efficiency of human mesenchymal stem cells (hMSC) with the plasmid pCMV-EGFP and compound 1.42. A) Observation of hMSC by phase contrast and fluorescence microscopy 24 hours after transfection with 400 ng of pCMV-EGFP and 2 μL of compound 1.42. B) GFP expression analysis by flow cytometry 24 hours after transfection of hMSC with 400 ng of pCMV-EGFP and 0.4, 0.6 and 0.8 μL of compound 1.42, with 500 ng of pCMV-EGFP and 0.5, 0.75 and 1 μL of compound 1.42, and 500 ng of pCMV-EGFP and 0.75 and 1.5 μL of Lipofectamine 3000 reagent.

FIG. 10. Chemical structure of a compound of general formula (II).

DESCRIPTION OF THE PREFERRED EMBODIMENTS

EXAMPLES

Experimental Section

Material and Methods

Cell Culture

Figure 3:
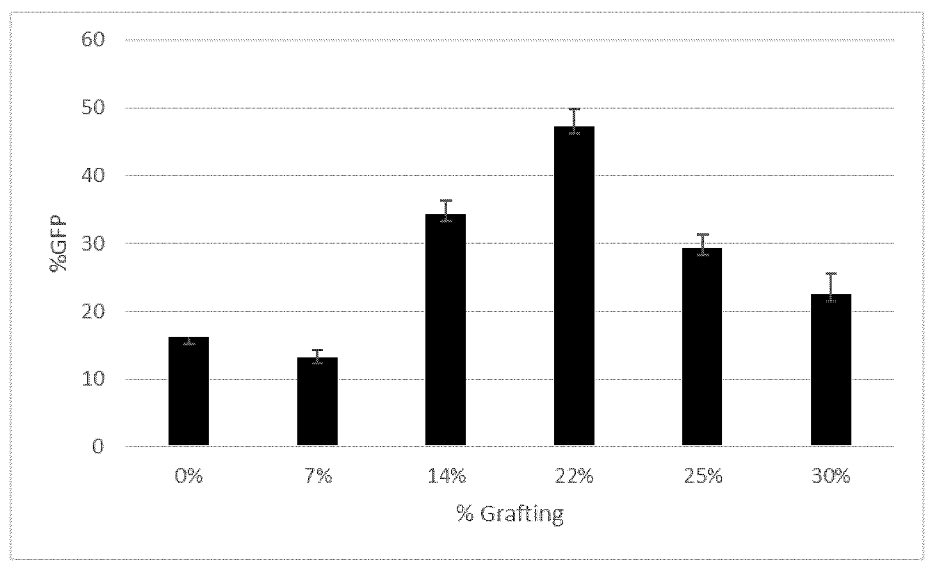
FIG. 3. Percentage of GFP expression after transfection of HepG2 cells with jetPEI® (a linear polyethylenimine-based DNA transfection reagent, ~22 kDa, Polyplus-transfection) (0% grafting) and compounds 1.57, 1.64, 1.42, 1.72, and 1.56 comprising 7%, 14%, 22%, 25% and 30% of grafting extent of 2-methyl-benzimadazole to the linear PEI 22 kDa, respectively.

Caco-2 (ATCC® HTB-37™) human colon epithelial cells were grown in DMEM 4.5 g/L glucose with 20% FBS supplemented with 1% non-essential amino acids, 1 mM sodium pyruvate, 2 mM glutamine and 100 U/mL of penicillin and 100 μg/mL of streptomycin at 37° C. in a 5% $CO_2$ in air atmosphere.

MCF 10A (ATCC® CRL-10317™) human mammary epithelial cells were grown in MEBM (Lonza) supplemented with SingleQuots™ Supplements and Growth Factors (Lonza) and 100 ng/ml cholera toxin at 37° C. in a 5% $CO_2$ in air atmosphere.

Hep G2 (ATCC® HB-8065™) human hepatocarcinoma cells were grown in MEM (Ozyme) with 10% FBS supplemented with 1% non-essential amino acids, 1 mM sodium pyruvate, 2 mM glutamine and 100 U/mL of penicillin and 100 μg/mL of streptomycin at 37° C. in a 5% $CO_2$ in air atmosphere.

MDCK (ATCC® CCL-34™) Madin-Darby canine kidney epithelial cells were grown in MEM (Ozyme) with 10% FBS supplemented with 2 mM glutamine and 100 U/mL of penicillin and 100 μg/mL of streptomycin at 37° C. in a 5% $CO_2$ in air atmosphere.

Primary human dermal fibroblasts were grown in DMEM (Ozyme) supplemented with 10% FBS, 1% non-essential amino acids, 1 mM sodium pyruvate, 2 mM glutamine and 100 U/ml of penicillin and 100 μg/mL of streptomycin at 37° C. in a 5% $CO_2$ in air atmosphere.

Transfection Assay (96-Well Format)

One day before transfection, Caco-2, MCF 10A, Hep G2 and MDCK Cells were seeded at 10 000, 25 000, 25 000, 10 000 cells per well (96-well plate format), respectively, in 125 μL of their respective complete medium and incubated at 37° C. in a 5% $CO_2$ in air atmosphere. On the day of transfection 200 ng of pCMV-EGFPLuc DNA (Clontech) was added in 20 μL of OPTIMEM (Thermo Fisher), mixed with a vortex and incubated for 5 minutes at room temperature (rt). Then, 0.6 or 0.8 μL of a compound of general formula (II) (at 7.5 mM nitrogen concentration) were added onto the diluted DNA, mixed with a vortex and incubated for 10 minutes at rt. The transfection DNA solution (20 μL) was added into the well and the plate was incubated for 24 hours at 37° C. in a 5% $CO_2$ in air atmosphere.

For the GFP expression analysis, one day post-transfection, the cell culture medium was removed and 50 μL of trypsin-EDTA (1×, Lonza) were added per well and the plate was incubated for 5 minutes at 37° C. 150 UL of complete medium were added to neutralize the trypsin, and the GFP expression was analysed (2000 events) by flow cytometry (Exc 488 nm, Em 520 nm) using a Guava easyCyte 6HT cytometer (Millipore).

Transfection Assay of Primary Cells

HUVEC Human Umbilical Vein Endothelial Cells (Promocell) were seeded at 20 000 cells per well (24-well plate format) in 500 μL of Endothelial Cell Growth Medium with supplementMix (Promocell) and incubated at 37° C. in a 5% $CO_2$ in air atmosphere. Three days later, the complete medium was removed and replaced by 500 μL of DMEM supplemented with 2% FBS. Then, 500 ng of pCMV-EGFPLuc DNA (Clontech) was added in 50 μL of NaCl buffer, mixed with a vortex and incubated for 5 minutes at rt. Then, 1.5 μL of a compound of general formula (II) (at 7.5 mM nitrogen concentration) were added onto the diluted DNA, mixed with a vortex and incubated for 10 minutes at rt. The transfection DNA solution (50 μL) was added into the well and the plate was incubated at 37° C. in a 5% $CO_2$ in air atmosphere. After 2 h of incubation, the medium was removed and replaced by 500 L of Endothelial Cell Growth Medium with supplementMix (Promocell) and cells were incubated at 37° C. in a 5% $CO_2$ in air atmosphere. One day post-transfection, the GFP expression was analysed by flow cytometry.

Primary human dermal fibroblasts were obtained from Pr. Stéphane Viville (Centre Hospitalier Universitaire, Strasbourg, France). The cells were grown in DMEM (Ozyme) supplemented with 10% FBS, 1% non-essential amino acids, 1 mM sodium pyruvate, 2 mM glutamine and 100 U/mL of penicillin and 100 μg/mL of streptomycin at 37° C. in a 5% $CO_2$ in air atmosphere. For the transfection, the cells were seeded at 40 000 cells per well (24-well plate format) precoated with 0.1% gelatin in 500 μL of DMEM with 10% FBS supplemented with 1% non-essential amino acids, 1 mM sodium pyruvate, 2 mM glutamine and 100 U/mL of penicillin and 100 μg/mL of streptomycin, and incubated for 24 h at 37° C. in a 5% $CO_2$ in air atmosphere. Then, 500 ng of pCMV-EGFPLuc DNA (Clontech) was added in 50 μL of NaCl buffer, mixed with a vortex and incubated for 5 minutes at rt. Then, 1.5 μL of a compound of general formula (II) (at 7.5 mM nitrogen concentration) were added onto the diluted DNA, mixed with a vortex and incubated for 10 minutes at rt. The transfection DNA solution (50 μL) was added into the well and the plate was incubated at 37° C. in a 5% $CO_2$ in air atmosphere. After 4 h of incubation, the medium was removed and replaced by 500 μL of complete DMEM, and cells were incubated at 37° C. in a 5% $CO_2$ in air atmosphere. One day post-transfection, the GFP expression was analysed by flow cytometry.

Primary rat Cortex Neurons (RCN, ThermoFisher) were seeded at 100 000 cells per well (48-well plate format) pre-coated with D-poly-lysine (Sigma) in 0.5 mL of complete neurobasal medium (ThermoFisher) supplemented with B27 supplement (ThermoFisher) and 0.5 mM glutamine, and cells were incubated at 37° C. in a 5% $CO_2$ in air atmosphere. Every two days, half of the complete medium volume was changed. After 4 days, 150 ng of pCMV-EGFPLuc DNA (Clontech) was added in 25 μL of OPTIMEM, mixed with a vortex and incubated for 5 minutes at rt. Then, 0.15 μL of a compound of general formula (II) (at 7.5 mM nitrogen concentration) were added onto the diluted DNA, mixed with a vortex and incubated for 10 minutes at rt. 250 μL of complete medium was removed and the formulated DNA solution (25 μL) was added into the well and the plate was incubated at 37° C. in a 5% $CO_2$ in air atmosphere. After 4 h of incubation at 37° C. in a 5% $CO_2$ in air atmosphere, 250 μL of the complete medium was added per well, and cells were incubated at 37° C. in a 5% $CO_2$ in air atmosphere. Cells were also transfected with 150 ng of pCMV-EGFPLuc complexed with LipoFectAmine® 3000 (ratio 1 μg: 1.5 μL), LipoFectAmine® 2000 (ratio 1 μg: 4 μL) in OPTIMEM and jetPEI® (ratio 1 μg: 2 μL) in 150 mM NaCl according to the recommended commercial protocols. One day post-transfection, the GFP expression was observed using a ZOET Fluorescent Cell Imager (a stand-alone digital fluorescence/brightfield cell imaging system) (Biorad).

Recombinant Virus Production

HEK-293T (ATCC® CRL-3216™): Human embryonic kidney cell is a highly transfectable derivative of human embryonic kidney 293 cells, and contains the SV40 T-antigen. HEK-293T cells are widely used for recombinant virus production, gene expression and protein production.

For adherent cells, HEK-293T cells were seeded at $5\times10^6$ cells in 145 $cm^2$ petri dishes in 15 mL of DMEM 4.5 g/L glucose supplemented with 10% FBS, 2 mM glutamine and 100 U/mL of penicillin and 100 μg/mL of streptomycin, and incubated at 37° C. in a 5% $CO_2$ in air atmosphere.

AAV-2 was produced in HEK-293 T cells using the AAV-2 Helper Free Packaging System (catalog number VPK-402, Cell BIOLABS, INC.) by co-transfection of 3 plasmids, pAAV-RC2 vector expressing Rep and Cap, pHelper vector expressing Adeno E2A, Adeno E4 and Adeno VA helper factors, and pAAV-GFP control vector expressing the GFP under the control of a CMV promoter. Transfection complexes (10 μg total DNA per petri dish) were prepared with a ratio of 2:2:1 with pAAV-RC2, pHelper and pAAV-GFP, respectively. Plasmids were diluted in a total volume of 1.5 mL of OPTIMEM. Then, 20 or 30 μL of compounds were added onto the diluted DNA, mixed with a vortex and incubated for 10 minutes at rt. Transfection complexes were added onto the cells and the plate was incubated for 72 h at 37° C. in a 5% $CO_2$ in air atmosphere.

For suspension cells, HEK-293T cells were seeded at $1\times10^6$ cells/mL in 27 ml of FreeStyle F17 supplemented with 4% Glutamine, 100 U/ml of penicillin, 100 μg/ml of streptomycin and 0.1% Pluronic in 125 mL flask Erlenmeyer (Corning). Cells were incubated for 24 h at 37° C. in an 8% $CO_2$ in air atmosphere under agitation (130 rpm). Plasmids (pAAV-GFP-pAAV-RC2-pHelper at ratio 2:2:1) were diluted in 3 mL of FreeStyle F17. Then, compounds were added onto the diluted DNA (ratio 2 or 3 μL per μg of DNA), mixed with a vortex and incubated for 10 minutes at rt. Transfection complexes were added onto the cells (2 μg DNA per $1\times10^6$ cells) and the plate was incubated for 72 h at 37° C. in a 8% $CO_2$ in air atmosphere under agitation (130 rpm).

Lentivirus particles were produced using the ViraSafe™ (a three-plasmid lentiviral packaging system) Lentiviral Packaging System, Pantropic (Catalog Number VPK-20, CELL BIOLABS INC.) containing pRSV-REV packaging vector, pCgpV Packaging Vector and pCMV-VSV-G Envelop Vector. pLenti6.3/V5-GW/EmGFP Expression Control Vector was from Thermo Fisher.

HEK-293T cells were seeded at $1\times10^6$ cells/mL in 27 mL of FreeStyle F17 supplemented with 4% Glutamine, 100

U/mL of penicillin, 100 μg/mL of streptomycin and 0.1% Pluronic in 125 mL flask Erlenmeyer (Corning). Cells were incubated for 24 h at 37° C. in an 8% $CO_2$ in air atmosphere under agitation (130 rpm). Plasmids (pRSV-REV-pCgpV-pCMV-VSV-G-pLenti6.3 at ratio 1:1:1:3) were diluted in 3 mL of FreeStyle F17. Then, compounds were added onto the diluted DNA (ratio 2 μL per μg of DNA), mixed with a vortex and incubated for 10 minutes at rt. Transfection complexes were added onto the cells (2 μg DNA per $1\times10^6$ cells) and the plate was incubated for 72 h at 37° C. in an 8% $CO_2$ in air atmosphere under agitation (130 rpm).

The transducing unit (TU/mL) was determined by using virus vectors expressing the GFP reporter gene after infection of permissive HT 1080 cells for lentivirus vectors and HEK-293T cells for AAV-2 vectors in 96-well and in presence of polybrene (8 μg/mL). The GFP expression was analysed by cytometry 72 h after transduction to determine the transducing units.

CRISPR Cas9 DNA Transfection

HEK293 (ECACC 85120602) human embryonic epithelial kidney cells were grown in Eagle MEM medium with 10% FBS supplemented with 2 mM Glutamine, 0.1 mM non-essential amino acids, 200 U/mL of penicillin and 200 μg/mL of streptomycin. One day before transfection, 12 500 cells were added per well (96-well plate format) in 125 μL of complete medium and the plate was incubated for 24 hours at 37° C. in a 5% $CO_2$ in air atmosphere.

The plasmid pSpCas9 BB-2A-GFP (9.3 kb) from GenScript (Leiden, Netherlands) used for the transfection experiment expressed a version of the *Streptococcus pyogenes* Cas9 protein (CRISPR Associated Protein 9) with an N and C terminal nuclear localization signal (NLS) under control of the CBh promoter. This plasmid contains a G (N) 20 gRNA (guide RNA) and the gRNA scaffold sequences under control of the U6 promoter. The G (N) 20 gRNA was designed to target the HPRT-1 (hypoxanthine phosphoribosyltransferase) human gene at the sequence position 38285 (targeted cleavage site by the CRISPR Cas9) generating the plasmid p38285. A second G (N) 20 gRNA was designed to generate the plasmid pCONTROL which is not able to trigger a CRISPR event in human cells.

On the day of transfection, 100 ng of plasmid p38285 or pCONTROL was added in 12 μL of OPTIMEM. Then, 0.1 μL of compound 1.42 at 7.5 mM amine concentration was added onto the diluted plasmid, mixed with a vortex and incubated for 10 minutes at rt. The complexed plasmid was added into the well and the plate was incubated 37° C. in a 5% $CO_2$ in air atmosphere.

Two days post-transfection, the medium was removed and cells were washed with PBS. Genomic DNA was isolated with the addition of 50 μL of QuickExtract™ (a proprietary buffer for rapid extraction of PCR-ready genomic DNA) DNA Extraction Solution 1.0 (Epicentre) per well followed by an incubation at 65° C. for 6 minutes, then at 98° C. for 2 minutes and storage at 4° C. The HPRT-1 targeted genomic DNA (250 ng) was amplified by PCR using the Primer HPRT1 mix (IDT) and the Q5® Hot Start High-Fidelity 2X Master Mix (a PCR master mix containing a high-fidelity hot-start DNA polymerase) (New England Biolabs®). The following PCR conditions were used in a iCycler™ Thermal Cycler (Biorad): 1) incubation at 95° C. for 5 minutes, 2) 35 cycles (98° C. for 20 seconds, 68° C. for 15 seconds, 72° C. for 30 seconds), 3) incubation at 72° C. for 2 minutes and then stored at 4° C. 15 μL of amplified PCR DNA (250 ng) were combined with 1.5 μL of 10X NEBuffer 2 (NEB) and 1.5 μL of nuclease free water (total volume of 18 μL) and denatured then re-annealed with thermocycling at 95° C. for 10 minutes, 95 to 85° C. at −2° C./second; 85 to 25° C. at −0.3° C./second. The re- annealed DNA was incubated with 1 μL of T7 Endonuclease I (10 U/μL, NEB) at 37° C. for 15 minutes. 19 μL of T7 Endonuclease reaction was combined with 2 μL of loading buffer and analyzed on a 2% TAE agarose gel electrophoresed for 45 minutes at 100 V in the presence of Quick Load 100 pb DNA ladder (a premixed molecular weight DNA marker) (New England Biolabs®). The gel was stained with ethidium bromide for 30 min. Cas9-induced cleavage bands (827 and 256 bp) and the uncleaved band (1083 bp) were visualized on a G: Box transilluminator (Syngene) and quantified using GeneTools software. The INDEL % was calculated using the following formula: INDEL %=100*[1-(1-((intensities of cleaved bands)/(intensities of cleaved bands and uncleaved band)))].

Transfection Assay of Stem Cells

Primary human mesenchymal stem cells (hMSC, Reference PT-2501, Lonza) were grown in MSC Basal Medium (Lonza) supplemented with GA-1000 (MSC Growth Medium, Lonza), 2 mM glutamine and 100 U/mL of penicillin and 100 μg/mL of streptomycin at 37° C. in a 5% $CO_2$ in air atmosphere.

HMSC were seeded at 12 000 cells per well (24-well plate format) in 500 μL of MSC complete growth medium (Lonza) and incubated at 37° C. in a 5% $CO_2$ in air atmosphere. Three days after the complete medium was removed and replaced by 500 μL of MSC Basal Medium. Then, pCMV-EGFP DNA (Clontech) was added in 50 μL of NaCl buffer, mixed with a vortex and incubated for 5 minutes at rt. Then, compound 1.42 (at 7.5 mM nitrogen concentration) was added onto the diluted DNA, mixed with a vortex and incubated for 10 minutes at rt. The formulated DNA solution (50 μL) was added into the well and the plate was incubated at 37° C. in a 5% $CO_2$ in air atmosphere. After 4 h of incubation, the medium was removed and replaced by 500 μL of MSC complete growth medium and cells were incubated at 37° C. in a 5% $CO_2$ in air atmosphere. One day post-transfection, the GFP expression was analysed by flow cytometry or observed using a ZOE™ Fluorescent Cell Imager (Biorad).

Example 1. General Procedure for the Preparation of Grafted Polymers

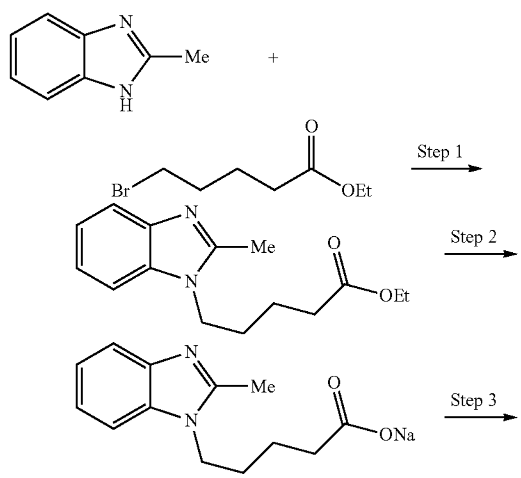

-continued

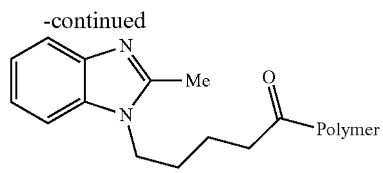

Step 1: N-Alkylation of Heterocycles

In an oven-dried round-bottom flask under argon was added the corresponding heterocycle (1 equiv.) and DMF (2 ml/mmol of starting material). The solution was cooled to 0° C. and Sodium Hydride (60% dispersion in mineral oil, 1.2 equiv.) was added by portion. The mixture was slowly warmed up to room temperature over 1 h. Then, the corresponding ester was added dropwise and the reaction was stirred at room temperature for 4-12 h. The mixture was quenched by addition of water (10 mL/1 mL of DMF) and the aqueous layer was extracted with EtOAc. (5×2 mL/1 mL of DMF). The combined organic extracts were washed with brine and dried over anhydrous $MgSO_4$. After filtration, the solvent was removed in vacuo and the resulting oil was purified by column chromatography (EtOAc 20 to 50% in heptane).

Step 2: Saponification of Acid Moieties

To a solution of ester in EtOH (2 mL/mmol of ester) was added dropwise a 5M solution of NaOH (0.2 mL/mmol of ester), and the mixture was stirred at room temperature overnight. Then, the solvent was removed in vacuo and the residue was purified by column chromatography on $SiO_2$ using MeOH 5% in DCM+AcOH 1% or using Acetonitrile 0 to 100% in $H_2O$.

Step 3: Grafting

In a round-bottom flask was added the cationic polymer (1 equiv.) in water (4 mL/mmol of starting material) followed by N-methyl morpholine or NMM (2 equiv.). The carboxylate (0.3-1 equiv.) was added followed by MeOH (16 mL/mmol of polymer). After stirring 10 min, 4-(4,6-dimethoxy-1,3,5-triazin-2-yl)-4-methylmorpholinium chloride was added or DMTMM (0.6-2 equiv.) and the mixture was stirred 12-24 h at room temperature. Then, MeOH was removed in vacuo, water (4 mL/mmol of starting material) followed by a solution of 3M HCl (1 mL/mmol of starting material) were added. The residue was purified using a dialysis cassette in a 50 mM HCl bath or by UF using Amicon Ultra 15 with HCl 50 mM.

Step 4: Procedure for Grafting PLL (22K, Sigma-Aldrich) with EDCI and NHS.

At room temperature and in microwave vial, poly-L-lysine (1 equiv.) was dissolved in 25-mM MES (pH 6.5) buffer to which was added 4-imidazoleacetic acid (sodium salt) (0.75 to 1.5 equiv.). This solution was used to dissolve EDCI (1.5 to 3 equiv). NHS (1 equiv.) was dissolved in MES buffer and was added immediately to the poly-L-lysine solution. The vial was sealed and stirred for 24 h at room temperature. The product was then purified by dialysis against water or on Amicon ultra 15 with water.

Example 2. Syntheses of (i) Compounds of Formula (II) of the Invention (Benzimidazole, Benzopyrazole and Benzotriazole Derivatives), i.e. Compounds 1.01 to 1.72, 1.74 to 1.77, 1.79 and 2.01 to 2.18, and (ii) Imidazole Derivatives Such as Compounds 1.73, 1.78 and 1.80

Synthesis of Product 1.01

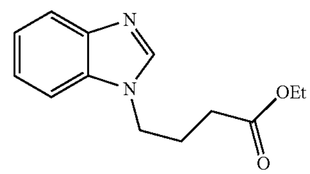 [SMILES: CCOC(=O)CCCn1cnc2ccccc21]

Intermediate 1.01a was prepared analogously to the general procedure, step 1 (Example 1). Yield=60%; m=2.30 g; 1H NMR (400 MHz, Chloroform-d) δ 7.94 (s, 1H), 7.81-7.72 (m, 1H), 7.43-7.36 (m, 1H), 7.26 (ddd, J=13.1, 7.5, 4.9 Hz, 2H), 4.24 (t, J=7.0 Hz, 2H), 4.09 (q, J=7.4 Hz, 2H), 2.28 (t, J=7.0 Hz, 2H), 2.16 (p, J=7.0 Hz, 2H), 1.20 (t, J=7.1 Hz, 3H).

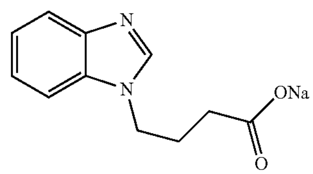

Intermediate 1.01b was prepared analogously to the general procedure, step 2 (Example 1). Yield=45%; m=1.00 g; 1H NMR (400 MHz, Methanol-$d_4$) δ 8.21 (d, J=2.4 Hz, 1H), 7.70 (d, J=8.0 Hz, 1H), 7.63 (d, J=8.0 Hz, 1H), 7.33 (dt, J=17.3, 7.5 Hz, 2H), 4.37 (t, J=7.4 Hz, 2H), 2.35 (t, J=7.4 Hz, 2H), 2.18 (p, J=7.4 Hz, 2H).

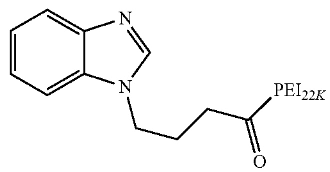

Product 1.01 was prepared analogously to the general procedure, step 3 (Example 1). Yield=94%; m=117 mg; $^1H$ NMR ($D_2O$) δ: $^1H$ NMR (400 MHz, Deuterium Oxide) δ 9.29-8.97 (m, 1H), 7.96-7.17 (m, 4H), 4.46 (d, J=42.4 Hz, 2H), 3.45 (s, 39H), 2.35 (dd, J=135.3, 58.1 Hz, 4H).

Synthesis of Product 1.02

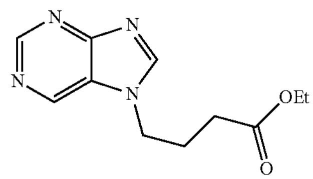 [SMILES: CCOC(=O)CCCn1cnc2ncncc21]

Intermediate 1.02a was prepared analogously to the general procedure, step 1 (Example 1). Yield=73%; m=857 mg; $^1$H NMR (400 MHz, Chloroform-d) δ 9.05 (s, 1H), 8.97 (s, 1H), 8.23 (s, 1H), 4.36 (t, J=7.1 Hz, 2H), 4.05 (q, J=7.2 Hz, 2H), 2.31 (m, 2H), 2.19 (m, 2H), 1.17 (t, J=7.2 Hz, 3H).

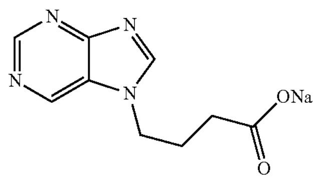

Intermediate 1.02b was prepared analogously to the general procedure, step 2 (Example 1). Yield=67%; m=48 mg; $^1$H NMR (400 MHz, Deuterium Oxide) δ 9.16 (s, 1H), 8.95 (s, 1H), 8.61 (s, 1H), 4.46-4.37 (m, 2H), 2.26-2.12 (m, 4H).

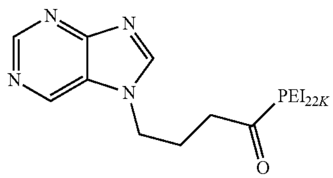

Product 1.02 was prepared analogously to the general procedure, step 3 (Example 1). Yield=85%; m=12 mg; $^1$H NMR (400 MHz, Deuterium Oxide) δ 9.57-7.98 (m, 3H), 4.60-4.16 (m, 2H), 4.15-3.05 (m, 24H), 2.92-1.71 (m, 4H).

Synthesis of Product 1.03

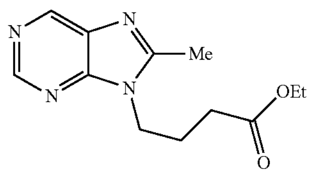 [SMILES: CCOC(=O)CCCn1c(C)nc2cncnc21]

Intermediate 1.03a was prepared analogously to the general procedure, step 2 (Example 1). Yield=100%; m=303 mg; $^1$H NMR (400 MHz, Deuterium Oxide) δ 8.86 (s, 1H), 8.77 (s, 1H), 4.25 (t, J=7.3 Hz, 2H), 2.67 (s, 3H), 2.21 (m, 2H), 2.10-2.01 (m, 2H).

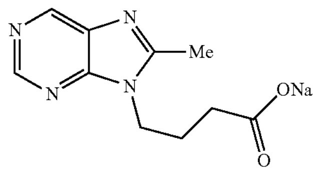

Intermediate 1.03b was prepared analogously to the general procedure, step 1 (Example 1). Yield=26%; m=327 mg; $^1$H NMR (400 MHz, Chloroform-d) δ 8.96 (s, 1H), 8.89 (s, 1H), 4.30 (dd, J=7.8, 6.8 Hz, 2H), 4.08 (q, J=7.2 Hz, 2H), 2.69 (s, 3H), 2.38 (t, J=6.9 Hz, 2H), 2.21-2.09 (m, 2H), 1.20 (t, J=7.1 Hz, 3H).

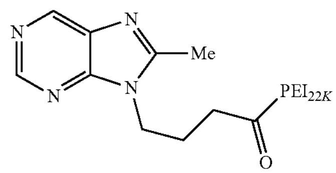

Product 1.03 was prepared analogously to the general procedure, step 3 (Example 1). Yield=88%; m=13 mg; $^1$H NMR (400 MHz, Deuterium Oxide) δ 9.20-8.32 (m, 2H), 4.51-2.93 (m, 21H), 2.88-1.68 (m, 7H).

Synthesis of Product 1.04

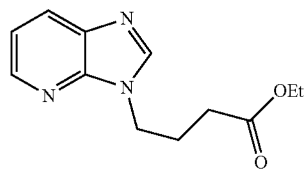 [SMILES: CCOC(=O)CCCn1cnc2cccnc21]

Intermediate 1.04a was prepared analogously to the general procedure, step 1 (Example 1). Yield=51%; m=597 mg; $^1$H NMR (400 MHz, Chloroform-d) δ 8.41 (dd, J=4.8, 1.5 Hz, 1H), 8.21 (s, 1H), 8.09 (dd, J=8.1, 1.5 Hz, 1H), 7.29-7.22 (m, 1H), 4.40 (t, J=6.8 Hz, 2H), 4.10 (q, J=7.1 Hz, 2H), 2.42-2.17 (m, 4H), 1.22 (t, J=7.1 Hz, 3H).

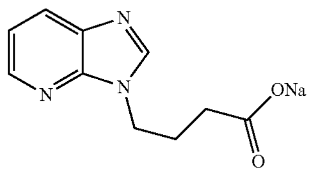

Intermediate 1.04b was prepared analogously to the general procedure, step 2 (Example 1). Yield=76%; m=441 mg; $^1$H NMR (400 MHz, Deuterium Oxide) δ δ 8.21 (s, 1H), 8.18 (dd, J=4.9, 1.4 Hz, 1H), 7.94 (dd, J=8.1, 1.4 Hz, 1H), 7.22 (dd, J=8.1, 4.9 Hz, 1H), 4.17 (t, J=7.0 Hz, 2H), 2.14 (m, 2H), 2.05 (m, 2H).

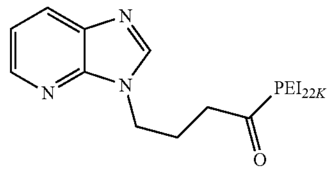

Product 1.04 was prepared analogously to the general procedure, step 3 (Example 1). Yield=78%; m=10 mg; $^1$H NMR (400 MHz, Deuterium Oxide) δ 9.46-7.11 (m, 4H), 4.64-4.15 (m, 1H), 4.14-1.88 (m, 41H).

Synthesis of Product 1.05

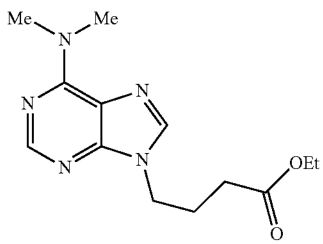 [SMILES: CCOC(=O)CCCn1cnc2c(N(C)C)ncnc21]

Intermediate 1.05a was prepared analogously to the general procedure, step 1 (Example 1). Yield=77%; m=783 mg; $^1$H NMR (400 MHz, Chloroform-d) δ 8.33 (d, J=3.7 Hz, 1H), 7.71 (d, J=3.0 Hz, 1H), 4.24 (m, 2H), 4.11 (m, 2H), 3.53 (s, 6H), 2.31 (m, 2H), 2.19 (m, 2H), 1.23 (m, 3H).

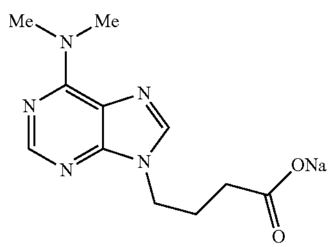

Intermediate 1.05b was prepared analogously to the general procedure, step 2 (Example 1). Yield=68%; m=311 mg; $^1$H NMR (400 MHz, Deuterium Oxide) δ 7.88 (s, 1H), 7.87 (s, 1H), 4.05 (t, J=7.2 Hz, 2H), 3.19 (s, 6H), 2.19-2.11 (m, 2H), 2.01 (dt, J=8.4, 6.6 Hz, 2H).

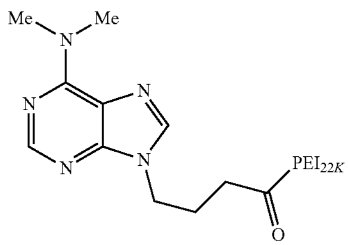

Product 1.05 was prepared analogously to the general procedure, step 3 (Example 1). Yield=74%; m=13 mg; $^1$H NMR (400 MHz, Deuterium Oxide) δ 8.62-7.38 (m, 2H), 4.42-1.55 (m, 17H).

Synthesis of Product 1.06

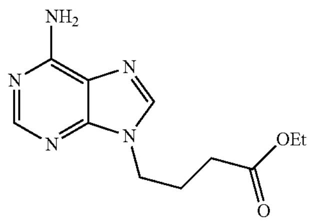 [SMILES: CCOC(=O)CCCn1cnc2c(N)ncnc21]

Intermediate 1.06a was prepared analogously to the general procedure, step 1 (Example 1). Yield=44%; m=810 mg; $^1$H NMR (400 MHz, Chloroform-d) o 8.33 (s, 1H), 7.80 (s, 1H), 6.47-6.06 (m, 2H), 4.26 (t, J=7.0 Hz, 2H), 4.10 (q, J=7.1 Hz, 2H), 2.32 (td, J=6.9, 1.0 Hz, 2H), 2.25-2.11 (m, 2H), 1.21 (t, J=7.1 Hz, 4H)

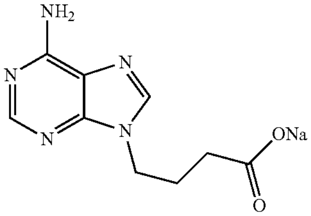

Intermediate (1.06b) was prepared analogously to the general procedure, step 2 (Example 1). Yield=99%; m=710 mg; $^1$H NMR (400 MHz, Deuterium Oxide) δ 7.94 (s, 1H), 7.91 (s, 1H), 4.03 (t, J=7.1 Hz, 2H), 2.07 (ddd, J=7.9, 7.0, 1.2 Hz, 2H), 2.00-1.89 (m, 2H).

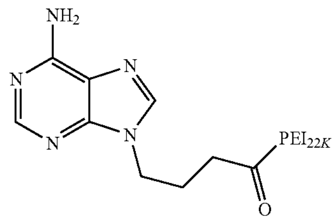

Product 1.06 was prepared analogously to the general procedure, step 3 (Example 1). Yield=99%; m=13 mg; $^1$H NMR (400 MHz, Deuterium Oxide) δ 8.78-7.72 (m, 2H), 4.33-1.07 (m, 38H).

Synthesis of Product 1.07

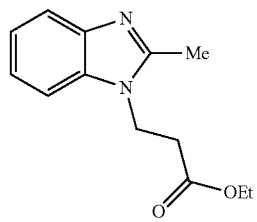 [SMILES: CCOC(=O)CCn1c(C)nc2ccccc21]

Intermediate 1.07a was prepared analogously to the general procedure, step 1 (Example 1). Yield=61%; m=2.7 g; $^1$H NMR (400 MHz, Chloroform-d) δ 7.70 (dq, J=7.0, 3.9, 3.3 Hz, 1H), 7.33 (dt, J=5.8, 2.5 Hz, 1H), 7.30-7.20 (m, 2H), 4.49-4.40 (m, 2H), 4.18-4.07 (m, 2H), 2.87-2.78 (m, 2H), 2.67 (d, J=2.2 Hz, 3H), 1.21 (td, J=7.2, 2.2 Hz, 3H).

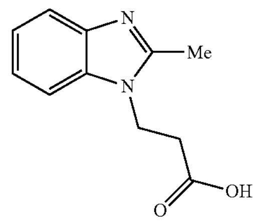 [SMILES: Cc1nc2ccccc2n1CCC(=O)O]

Intermediate 1.07b was prepared analogously to the general procedure, step 2 (Example 1). Yield=17%; m=400 mg; $^1$H NMR (400 MHz, Deuterium Oxide) δ 7.71 (d, J=7.4 Hz, 1H), 7.62 (d, J=7.3 Hz, 1H), 7.49 (dd, J=7.3, 3.8 Hz, 2H), 4.60 (q, J=5.8 Hz, 2H), 2.93 (q, J=5.8 Hz, 2H), 2.81 (d, J=2.8 Hz, 3H).

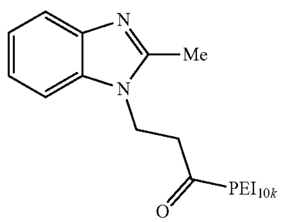

Product 1.07 was prepared analogously to the general procedure, step 3 (Example 1). Yield=96%; m=134 mg; $^1$H NMR (400 MHz, Deuterium Oxide) δ 8.03-7.09 (m, 4H), 4.34-2.28 (m, 32H).

Synthesis of Product 1.08

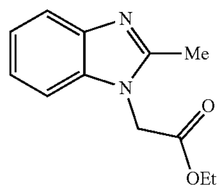 [SMILES: CCOC(=O)Cn1c(C)nc2ccccc21]

Intermediate 1.08a was prepared analogously to the general procedure, step 1 (Example 1). Yield=73%; m=3.0 g; $^1$H NMR (400 MHz, Chloroform-d) δ 7.76-7.70 (m, 1H), 7.26 (tdd, J=9.4, 6.6, 3.4 Hz, 3H), 4.82 (s, 2H), 4.25 (q, J=7.2 Hz, 2H), 2.61 (d, J=1.6 Hz, 3H), 1.33-1.24 (m, 3H).

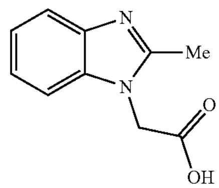 [SMILES: Cc1nc2ccccc2n1CC(=O)O]

Intermediate 1.08b was prepared analogously to the general procedure, step 2 (Example 1). Yield=27%; m=700 mg; $^1$H NMR ($D_2O$) δ: $^1$H NMR (400 MHz, Deuterium Oxide) δ 7.63 (ddt, J=18.8, 6.4, 2.9 Hz, 2H), 7.50 (dq, J=6.5, 3.5 Hz, 2H), 5.15 (d, J=2.7 Hz, 2H), 2.74 (d, J=2.7 Hz, 3H).

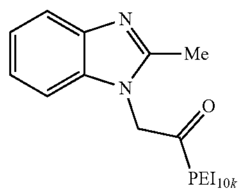

Product 1.08 was prepared analogously to the general procedure, step 3 (Example 1). Yield=100%; m=130 mg; $^1$H NMR (400 MHz, Deuterium Oxide) δ 7.88-7.28 (m, 4H), 5.71-5.17 (m, 2H), 4.12-3.12 (m, 45H), 2.89-2.41 (m, 3H).

Synthesis of Product 1.09

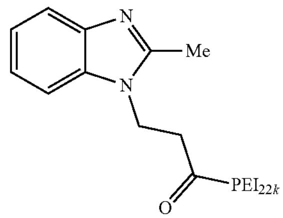

Product 1.09 was prepared analogously to the general procedure, step 3 (Example 1). Yield=100%; m=150 mg; $^1$H NMR (400 MHz, Deuterium Oxide) δ 7.87-7.21 (m, 4H), 4.15-2.49 (m, 29H).

Synthesis of Product 1.10

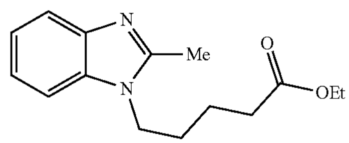 [SMILES: CCOC(=O)CCCCn1c(C)nc2ccccc21]

Intermediate 1.10a was prepared analogously to the general procedure, step 1 (Example 1). Yield=28%; m=610 mg; $^1$H NMR (400 MHz, Chloroform-d) δ 7.74 -7.66 (m, 1H), 7.34-7.27 (m, 1H), 7.31-7.21 (m, 2H), 4.20-4.08 (m, 4H), 3.43 (td, J=6.6, 1.5 Hz, OH), 2.64 (d, J=1.5 Hz, 3H), 2.35 (t, J=7.2 Hz, 2H), 1.98-1.67 (m, 5H), 1.32-1.19 (m, 3H).

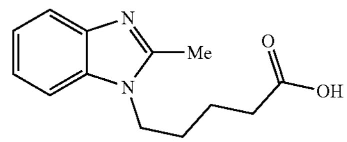 [SMILES: Cc1nc2ccccc2n1CCCCC(=O)O]

Intermediate 1.10b was prepared analogously to the general procedure, step 2 (Example 1). Yield=71%; m=386 mg; $^1$H NMR (400 MHz, Methanol-$d_4$) δ 7.82 (d, J=7.4 Hz, 1H), 7.76-7.69 (m, 1H), 7.59-7.49 (m, 2H), 4.45 (t, J=7.5 Hz, 2H), 2.85 (d, J=2.2 Hz, 3H), 2.40 (t, J=7.2 Hz, 2H), 1.96 (p, J=8.0, 7.3 Hz, 2H), 1.74 (q, J=7.7 Hz, 2H).

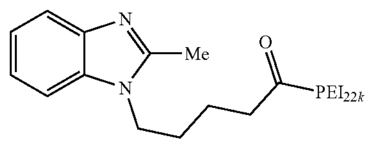

Product 1.10 was prepared analogously to the general procedure, step 3 (Example 1). Yield=98%; m=170 mg; $^1$H NMR (400 MHz, Deuterium Oxide) δ 7.90-7.00 (m, 4H), 4.42-3.02 (m, 14H), 2.84-2.56 (m, 2H), 2.55-2.11 (m, 2H), 1.98-1.25 (m, 6H).

Synthesis of Product 1.11

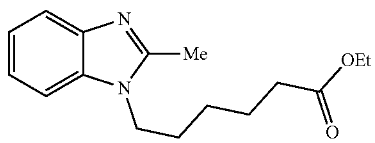 [SMILES: CCOC(=O)CCCCCn1c(C)nc2ccccc21]

Intermediate 1.11a was prepared analogously to the general procedure, step 1 (Example 1). Yield=30%; m=1.44 g; $^1$H NMR (400 MHz, Chloroform-d) δ 7.76-7.67 (m, 1H), 7.30 (dd, J=6.3, 3.0 Hz, 1H), 7.25 (dd, J=6.2, 3.1 Hz, 2H), 4.13 (p, J=7.3 Hz, 4H), 2.62 (s, 3H), 2.31 (t, J=7.4 Hz, 2H), 1.84 (p, J=7.5 Hz, 2H), 1.69 (p, J=7.5 Hz, 2H), 1.48-1.36 (m, 2H), 1.26 (t, J=7.1 Hz, 3H).

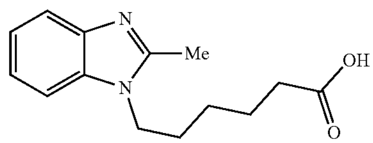 [SMILES: Cc1nc2ccccc2n1CCCCCC(=O)O]

Intermediate 1.11b was prepared analogously to the general procedure, step 2 (Example 1). Yield=75%; m=970 mg; $^1$H NMR (400 MHz, Methanol-$d_4$) δ 7.57 (d, J=7.6 Hz, 1H), 7.50 (d, J=7.7 Hz, 1H), 7.27 (p, J=7.4 Hz, 2H), 4.24 (t, J=7.4 Hz, 2H), 2.63 (d, J=2.2 Hz, 3H), 2.30 (t, J=7.4 Hz, 2H), 1.85 (p, J=7.8 Hz, 2H), 1.67 (p, J=7.5 Hz, 2H), 1.43 (p, J=7.8 Hz, 2H).

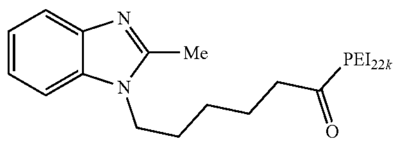

Product 1.11 was prepared analogously to the general procedure, step 3 (Example 1). Yield=100%; m=206 mg; $^1$H NMR (400 MHz, Deuterium Oxide) 7.80-7.24 (m, 4H), 4.43-3.03 (m, 13H), 2.83-2.50 (m, 3H), 2.45-1.97 (m, 2H), 1.91-1.05 (m, 6H).

Synthesis of Product 1.12

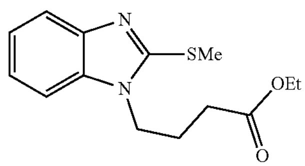 [SMILES: CCOC(=O)CCCn1c(SC)nc2ccccc21]

Intermediate 1.12a was prepared analogously to the general procedure, step 1 (Example 1). Yield=85%; m=3.63 g; $^1$H NMR (400 MHz, Chloroform-d) δ 7.78-7.69 (m, 1H), 7.36-7.28 (m, 1H), 7.26 (s, 1H), 7.24 (d, J=4.1 Hz, 1H), 4.24-4.13 (m, 4H), 2.86 (d, J=1.3 Hz, 3H), 2.40 (t, J=7.0 Hz, 2H), 2.19 (dp, J=14.1, 6.9 Hz, 2H), 1.34-1.25 (m, 3H).

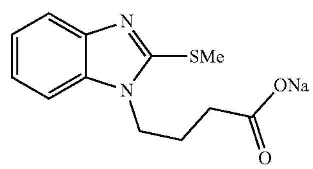

Intermediate 1.12b was prepared analogously to the general procedure, step 2 (Example 1). Yield=36%; m=1.19 g; $^1$H NMR (400 MHz, Methanol-$d_4$) δ 7.59 (d, J=7.2 Hz, 1H), 7.48 (d, J=7.2 Hz, 1H), 7.30-7.19 (m, 2H), 4.26 (t, J=7.3 Hz, 2H), 2.78 (d, J=2.2 Hz, 3H), 2.38 (t. J=7.1 Hz, 2H), 2.10 (p, J=7.3 Hz, 2H).

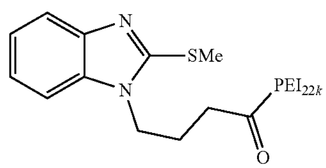

Product 1.12 was prepared analogously to the general procedure, step 3 (Example 1). Yield=100%; m=217 mg; $^1$H NMR (400 MHz, Deuterium Oxide) δ 7.80-6.90 (m, 4H), 4.52-3.09 (m, 12H), 3.05-1.63 (m, 7H).

Synthesis of Product 1.13

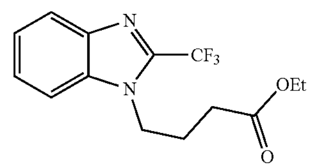 [SMILES: CCOC(=O)CCCn1c(C(F)(F)F)nc2ccccc21]

Intermediate 1.13a was prepared analogously to the general procedure, step 1 (Example 1). Yield=33%; m=750 mg; $^1$H NMR (400 MHz, Methanol-$d_4$) δ 7.82-7.66 (m, 2H), 7.53-7.36 (m, 2H), 4.46 (t, J=7.8 Hz, 1H), 4.09 (q, J=7.4 Hz, 1H), 2.46 (t, J=6.9 Hz, 2H), 2.15 (t, J=7.5 Hz, 2H), 1.23 (t, J=7.3 Hz, 3H).

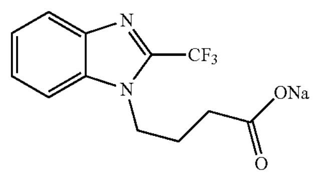

Intermediate 1.13b was prepared analogously to the general procedure, step 2 (Example 1). Yield=53%; m=360 mg; $^1$H NMR (400 MHz, Methanol-$d_4$) o 7.80 (t, J=6.7 Hz, 2H), 7.52 (t, J=7.9 Hz, 1H), 7.44 (t, J=7.8 Hz, 1H), 4.51 (t, J=7.9 Hz, 2H), 2.47 (t, J=7.1 Hz, 2H), 2.17 (p, J=7.4 Hz, 2H).

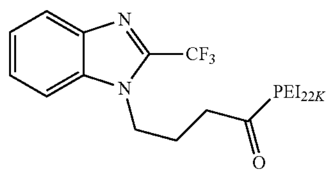

Product 1.13 was prepared analogously to the general procedure, step 3 (Example 1). Yield=100%; m=150 mg; $^1$H NMR (400 MHz, Deuterium Oxide) δ 8.39-5.98 (m, 4H), 4.49-0.19 (m, 17H).

Synthesis of Product 1.14

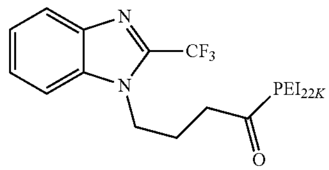

Product 1.14 was prepared analogously to the general procedure, step 3 (Example 1). Yield=93%; m=237 mg; $^1$H NMR (400 MHz, Deuterium Oxide) δ 7.94-6.59 (m, 4H), 4.62-1.17 (m, 28H).

Synthesis of Product 1.15

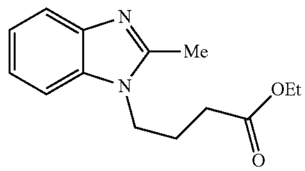 [SMILES: CCOC(=O)CCCn1c(C)nc2ccccc21]

Intermediate 1.15a was prepared analogously to the general procedure, step 2 (Example 1). Yield=91%; m=1.19 g; $^1$H NMR (400 MHz, Chloroform-d) δ 7.73-7.66 (m, 1H), 7.34 (dd, J=6.7, 2.7 Hz, 1H), 7.24 (dd, J=4.6, 2.0 Hz, 2H), 4.24-4.09 (m, 4H), 2.64 (s, 3H), 2.37 (t, J=6.8 Hz, 2H), 2.12 (p, J=7.1 Hz, 2H), 1.25 (td, J=7.1, 1.5 Hz, 3H).

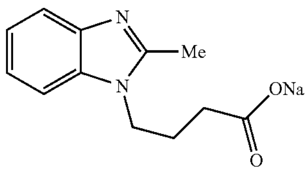

Intermediate 1.15b was prepared analogously to the general procedure, step 2 (Example 1). Yield=31%; m=1.46 g; $^1$H NMR ($CDCl_3$) δ: $^1$H NMR (400 MHz, Deuterium Oxide) δ 7.71-7.64 (m, 1H), 7.60 (d, J=6.9 Hz, 1H), 7.52-7.41 (m, 2H), 4.35-4.26 (m, 2H), 2.75 (d, J=2.6 Hz, 3H), 2.24 (td, J=7.1, 2.6 Hz, 2H), 2.06 (q, J=7.5 Hz, 2H).

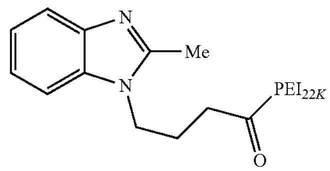

Product 1.15 was prepared analogously to the general procedure, step 3 (Example 1). Yield=100%; m=143 mg; $^1$H NMR (400 MHz, Deuterium Oxide) δ 7.84-7.10 (m, 4H), 4.51-3.09 (m, 22H), 3.07-1.61 (m, 6H).

Synthesis of Product 1.16

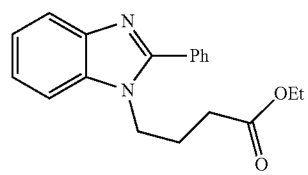 [SMILES: CCOC(=O)CCCn1c(-c2ccccc2)nc2ccccc21]

Intermediate 1.16a was prepared analogously to the general procedure, step 1 (Example 1). Yield=75%; m=2.4 g; $^1$H NMR (400 MHz, Chloroform-d) δ 7.85-7.79 (m, 1H), 7.75-7.68 (m, 2H), 7.51 (dq, J=6.1, 3.3, 2.3 Hz, 3H), 7.44-7.22 (m, 3H), 4.33 (t, J=7.4 Hz, 2H), 4.05 (q, J=7.1 Hz, 2H), 2.25 (t, J=6.8 Hz, 2H), 2.13 (p, J=7.0 Hz, 2H), 1.27-1.17 (m, 3H).

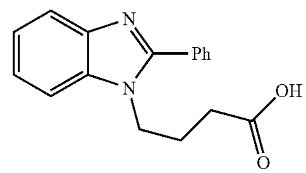

Intermediate 1.16b was prepared analogously to the general procedure, step 2 (Example 1). Yield=42%; m=920 mg; $^1$H NMR (400 MHz, Methanol-$d_4$) δ 8.11 (d, J=7.1 Hz, 1H), 7.94 (d, J=7.2 Hz, 2H), 7.86 (dd, J=16.2, 7.3 Hz, 2H), 7.79 (d, J=7.2 Hz, 2H), 7.71 (d, J=6.5 Hz, 2H), 4.62 (t, J=7.4 Hz, 2H), 2.44 (s, 2H), 2.22 (s, 2H).

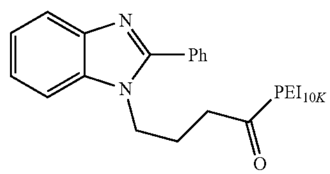

Product 1.16 was prepared analogously to the general procedure, step 3 (Example 1). Yield=96%; m=162 mg; $^1$H NMR (400 MHz, Deuterium Oxide) δ 8.36-6.92 (m, 9H), 4.57-2.85 (m, 21H), 2.76-1.33 (m, 4H).

Synthesis of Product 1.17

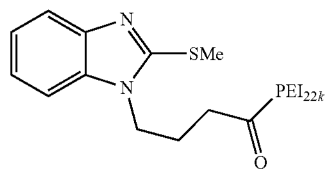

Product 1.17 was prepared analogously to the general procedure, step 3 (Example 1). Yield=99%; m=170 mg; $^1$H NMR (400 MHz, Deuterium Oxide) δ 7.82-7.03 (m, 4H), 4.40-2.94 (m, 19H), 2.94-1.41 (m, 7H).

Synthesis of Product 1.18

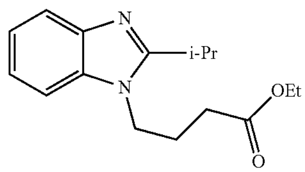 [SMILES: CCOC(=O)CCCn1c(C(C)C)nc2ccccc21]

Intermediate 1.18a was prepared analogously to the general procedure, step 1 (Example 1). Yield=44%; m=2.29 g; $^1$H NMR (400 MHz, Chloroform-d) δ 7.81-7.73 (m, 1H), 7.37 (dd, J=6.6, 2.8 Hz, 1H), 7.32-7.20 (m, 2H), 4.19 (dq, J=14.2, 7.3 Hz, 4H), 3.22 (hept, J=6.9 Hz, 1H), 2.40 (t, J=6.8 Hz, 2H), 2.14 (p, J=7.1 Hz, 2H), 1.48 (dd, J=6.8, 1.5 Hz, 6H), 1.29 (tt, J=7.1, 1.1 Hz, 3H).

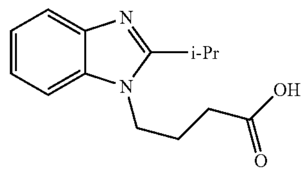 [SMILES: CC(C)c1nc2ccccc2n1CCCC(=O)O]

Intermediate 1.18b was prepared analogously to the general procedure, step 2 (Example 1). Yield=61%; m=1.25 g; $^1$H NMR (400 MHz, Methanol-$d_4$) δ 7.60 (dd, J=17.9, 7.6 Hz, 2H), 7.28 (t, J=7.0 Hz, 2H), 4.34 (t, J=7.8 Hz, 2H), 3.41 (h, J=7.0 Hz, 1H), 2.42 (t, J=6.9 Hz, 2H), 2.10 (p, J=7.1 Hz, 2H), 1.45 (dd, J=6.8, 2.1 Hz, 6H).

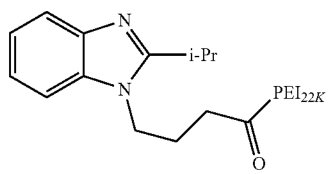

Product 1.18 was prepared analogously to the general procedure, step 3 (Example 1). Yield=94%; m=167 mg; $^1$H NMR (400 MHz, Deuterium Oxide) δ 7.79-7.22 (m, 4H), 4.42-3.06 (m, 17H), 2.82-2.50 (m, 3H), 2.46-2.01 (m, 2H), 1.93-1.00 (m, 6H).

Synthesis of Product 1.19

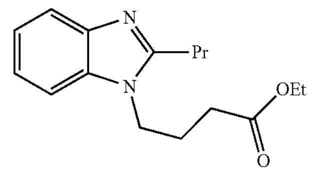

Intermediate 1.19a was prepared analogously to the general procedure, step 1 (Example 1). Yield=41%; m=700 mg; $^1$H NMR (400 MHz, Chloroform-d) δ 7.78 -7.70 (m, 1H), 7.39-7.32 (m, 1H), 7.31-7.20 (m, 2H), 4.24-4.12 (m, 4H), 2.87 (t, J=7.7 Hz, 2H), 2.39 (t, J=6.8 Hz, 2H), 2.13 (p, J=7.1 Hz, 2H), 1.96 (h, J=7.5 Hz, 2H), 1.28 (td, J=7.2, 1.6 Hz, 3H), 1.09 (td, J=7.3, 1.6 Hz, 3H).

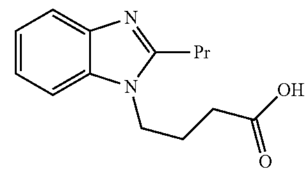

Intermediate 1.19b was prepared analogously to the general procedure, step 2 (Example 1). Yield=97%; m=610 mg; $^1$H NMR (400 MHz, Methanol-$d_4$) δ 7.64-7.55 (m, 2H), 7.29 (t, J=7.1 Hz, 2H), 4.32 (t, J=7.7 Hz, 2H), 3.33 (s, 2H), 2.97 (t, J=7.4 Hz, 2H), 2.42 (t, J=6.9 Hz, 2H), 2.10 (p, J=7.0 Hz, 2H), 1.92 (h, J=7.6 Hz, 2H), 1.09 (td, J=7.4, 2.2 Hz, 3H).

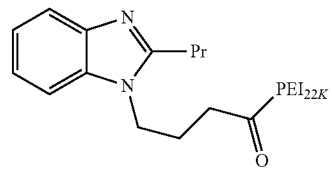

Product 1.19 was prepared analogously to the general procedure, step 3 (Example 1). Yield=95%; m=166 mg; $^1$H NMR (400 MHz, Deuterium Oxide) δ 7.85-6.97 (m, 4H), 4.53-2.81 (m, 19H), 2.77-2.25 (m, 2H), 2.21-1.48 (m, 4H), 1.06-0.73 (m, 3H).

Synthesis of Product 1.20

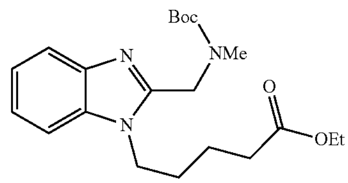 [SMILES: CCOC(=O)CCCCn1c(CN(C)C(=O)OC(C)(C)C)nc2ccccc21]

Intermediate 1.20a was prepared analogously to the general procedure, step 1 (Example 1). Yield=100%; m=1.54 g; $^1$H NMR (400 MHz, Chloroform-d) δ 7.72 (d, J=7.3 Hz, 1H), 7.44 (d, J=7.6 Hz, 1H), 7.32-7.19 (m, 2H), 4.77 (s, 2H), 4.29 (t, J=7.8 Hz, 2H), 4.09 (q, J=7.1 Hz, 2H), 2.85 (s, 3H), 2.39-2.31 (m, 2H), 2.07-1.96 (m, 2H), 1.44 (s, 9H), 1.21 (t, J=7.1 Hz, 3H).

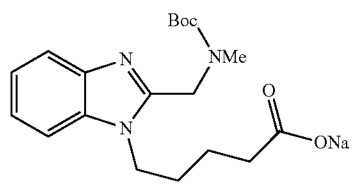

Intermediate 1.20b was prepared analogously to the general procedure, step 2 (Example 1). Yield=69%; m=1.05 g; $^1$H NMR (400 MHz, Methanol-$d_4$) δ 7.64 (dd, J=17.8, 7.8 Hz, 2H), 7.31 (dt, J=17.0, 7.4 Hz, 2H), 4.79 (s, 2H), 4.34 (t, J=7.9 Hz, 2H), 2.95 (s, 3H), 2.41 (t, J=7.2 Hz, 2H), 2.07 (t, J=8.2 Hz, 2H), 1.48 (s, 9H).

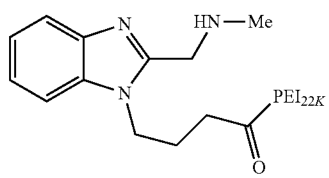

Product 1.20 was prepared analogously to the general procedure, step 3 (Example 1). Yield=98%; m=183 mg; $^1$H NMR (400 MHz, Deuterium Oxide) δ 7.92-6.90 (m, 4H), 4.53-3.08 (m, 18H), 3.00-2.77 (m, 3H), 2.72-1.73 (m, 4H).

Synthesis of Product 1.21

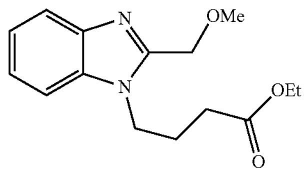 [SMILES: CCOC(=O)CCCn1c(COC)nc2ccccc21]

Intermediate 1.21a was prepared analogously to the general procedure, step 1 (Example 1). Yield=63%; m=2.63 g; $^1$H NMR (400 MHz, Chloroform-d) δ 7.77-7.70 (m, 1H), 7.44-7.37 (m, 1H), 7.32-7.20 (m, 2H), 4.74 (d, J=2.1 Hz, 2H), 4.33-4.24 (m, 2H), 4.10 (qd, J=7.2, 1.9 Hz, 2H), 3.37 (d, J=2.0 Hz, 3H), 2.35 (td, J=6.9, 2.0 Hz, 2H), 2.13 (p, J=7.1 Hz, 2H), 1.22 (td, J=7.1, 2.0 Hz, 3H).

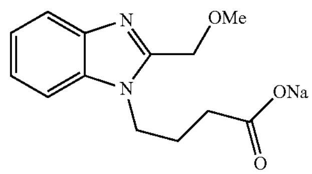

Intermediate 1.21b was prepared analogously to the general procedure, step 2 (Example 1). Yield=63%; m=1.63 g; $^1$H NMR (400 MHz, Methanol-$d_4$) δ 7.65 (ddd, J=18.3, 8.2, 2.8 Hz, 2H), 7.39-7.25 (m, 2H), 4.76 (t, J=2.3 Hz, 2H), 4.43-4.34 (m, 2H), 3.44 (s, 3H), 2.41 (td, J=7.2, 6.5, 3.7 Hz, 2H), 2.17 (q, J=7.8 Hz, 2H).

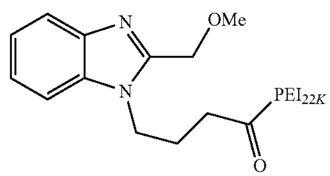

Product 1.21 was prepared analogously to the general procedure, step 3 (Example 1). Yield=91%; m=172 mg; $^1$H NMR (400 MHz, Deuterium Oxide) δ 7.92-7.09 (m, 4H), 5.08-4.82 (m, 2H), 4.51-4.06 (m, 2H), 4.00-2.98 (m, 16H), 2.77-2.27 (m, 2H), 2.22-1.65 (m, 2H).

Synthesis of Product 1.22

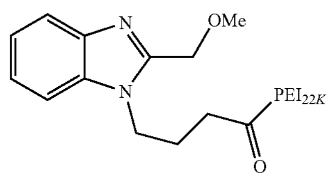

Product 1.22 was prepared analogously to the general procedure, step 3 (Example 1). Yield=42%; m=129 mg; $^1$H NMR (400 MHz, Deuterium Oxide) δ 7.95-7.13 (m, 4H), 5.17-4.86 (m, 2H), 4.54-4.14 (m, 2H), 4.10-3.01 (m, 22H), 2.98-2.32 (m, 2H), 2.30-1.70 (m, 2H).

Synthesis of Product 1.23

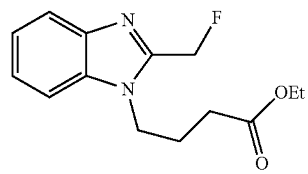 [SMILES: CCOC(=O)CCCn1c(CF)nc2ccccc21]

Intermediate 1.23a was prepared analogously to the general procedure, step 1 (Example 1). Yield=29%; m=523 mg; $^1$H NMR (400 MHz, Chloroform-d) δ 7.83 (d, J=7.8 Hz, 1H), 7.52 (d, J=7.9 Hz, 1H), 7.37 (dt, J=17.6, 7.3 Hz, 2H), 5.75 (d, J=47.8 Hz, 2H), 4.38 (t, J=7.6 Hz, 2H), 4.15 (q, J=7.3 Hz, 2H), 2.41 (t, J=6.8 Hz, 2H), 2.21 (p, J=7.0 Hz, 2H), 0.98-0.79 (m, 3H).

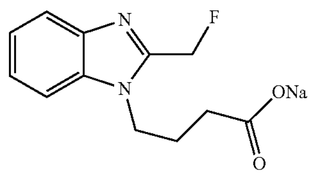

Intermediate 1.23b was prepared analogously to the general procedure, step 2 (Example 1). Yield=67%; m=343 mg; $^1$H NMR (400 MHz, Methanol-$d_4$) δ 7.75-7.63 (m, 2H), 7.44-7.27 (m, 2H), 5.70 (dd, J=47.9, 3.0 Hz, 2H), 4.47-4.36 (m, 2H), 2.41 (q, J=5.5, 4.5 Hz, 2H), 2.17 (q, J=7.8 Hz, 2H).

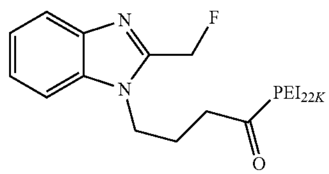

Product 1.23 was prepared analogously to the general procedure, step 3 (Example 1). Yield=99%; m=166 mg; $^1$H NMR 400 MHz, Deuterium Oxide) δ 7.96-7.21 (m, 4H), 6.02-5.95 (m, 2H), 4.59-4.14 (m, 2H), 3.48-3.24 (m, 17H), 2.91-1.66 (m, 4H).

Synthesis of Product 1.24

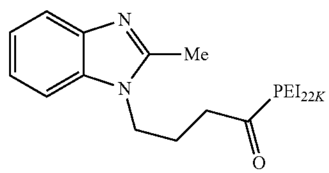

Product 1.24 was prepared analogously to the general procedure, step 3 (Example 1). Yield=91%; m=117 mg; $^1$H NMR 400 MHz, Deuterium Oxide) δ 7.95-7.17 (m, 4H), 4.54-2.39 (m, 24H), 2.07-1.56 (m, 2H).

Synthesis of Product 1.25

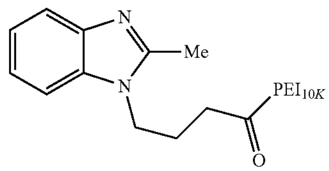

Product 1.25 was prepared analogously to the general procedure, step 3 (Example 1). Yield=81%; m=137 mg; $^1$H NMR 400 MHz, Deuterium Oxide) δ 7.82-7.05 (m, 4H), 4.62-2.27 (m, 22H), 2.12-1.74 (m, 2H).

Synthesis of Product 1.26

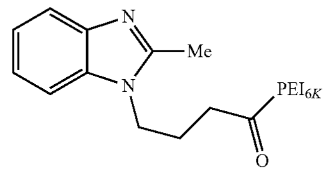

Product 1.26 was prepared analogously to the general procedure, step 3 (Example 1). Yield=81%; m=101 mg; $^1$H NMR 400 MHz, Deuterium Oxide) δ 7.94-7.18 (m, 4H), 4.71-2.18 (m, 25H), 2.05-1.82 (m, 2H).

Synthesis of Product 1.27

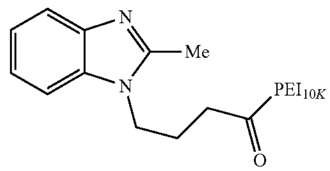

Product 1.27 was prepared analogously to the general procedure, step 3 (Example 1). Yield=91%; m=173 mg; $^1$H NMR 400 MHz, Deuterium Oxide) δ 7.87-7.02 (m, 4H), 4.51-2.23 (m, 17H), 2.10-1.67 (m, 2H).

Synthesis of Product 1.28

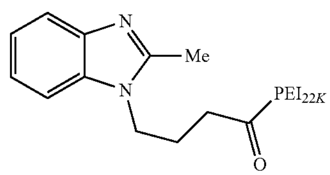

Product 1.28 was prepared analogously to the general procedure, step 3 (Example 1). Yield=100%; m=152 mg; $^1$H NMR (400 MHz, Deuterium Oxide) δ 7.95-7.20 (m, 4H), 4.56-3.11 (m, 24H), 2.99-2.34 (m, 6H), 2.28-1.68 (m, 2H).

Synthesis of Product 1.29

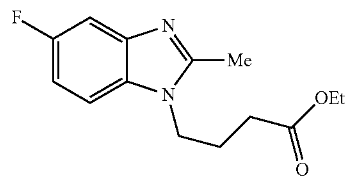 [SMILES: CCOC(=O)CCCn1c(C)nc2cc(F)ccc21]

Intermediate 1.29a was prepared analogously to the general procedure, step 1 (Example 1). Yield=86%; m=788 mg; $^1$H NMR (400 MHz, Chloroform-d) δ 7.57-7.46 (m, 0.5H), 7.27 (dd, J=9.4, 2.4 Hz, 0.5H), 7.16 (dd, J=9.3, 4.4 Hz, 0.5H), 6.99-6.81 (m, 1.5H), 4.06 (ddt, J=9.6, 7.1, 4.4 Hz, 4H), 2.52 (s, 2H), 2.28 (t, J=6.7 Hz, 2H), 2.02 (p, J=6.9 Hz, 2H), 1.18 (t, J=7.1 Hz, 3H).

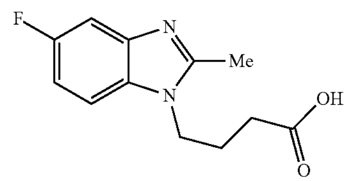

Intermediate 1.29b was prepared analogously to the general procedure, step 2 (Example 1). Yield=100%; m=786 mg, $^1$H NMR (400 MHz, Methanol-$d_4$) δ 7.60 (ddd, J=14.5, 8.8, 4.5 Hz, 1H), 7.38 (dd, J=49.0, 9.0 Hz, 1H), 7.12 (dt, J=16.4, 9.6 Hz, 1H), 4.32 (dt, J=12.6, 7.7 Hz, 2H), 2.69 (s, 3H), 2.43 (d, J=6.9 Hz, 2H), 2.11 (h, J=6.7 Hz, 2H).

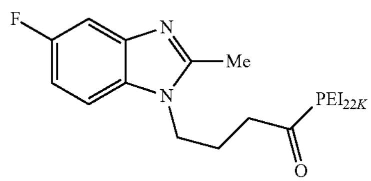

Product 1.29 was prepared analogously to the general procedure, step 3 (Example 1). Yield=100%; m=187 mg; $^1$H NMR (400 MHz, Deuterium Oxide) δ 8.12-6.68 (m, 3H), 4.44-3.03 (m, 16H), 2.90-2.27 (m, 5H), 2.18-1.71 (m, 2H).

Synthesis of Product 1.30

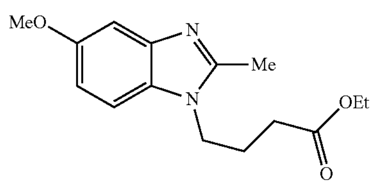 [SMILES: CCOC(=O)CCCn1c(C)nc2cc(OC)ccc21]

Intermediate 1.30a was prepared analogously to the general procedure, step 1 (Example 1). Yield=63%; m=1.7 g; $^1$H NMR (400 MHz, Chloroform-d) δ 7.63 (d, J=8.7 Hz, OH), 7.27 (d, J=8.8 Hz, 1H), 6.99-6.86 (m, 2H), 4.27-4.15 (m, 4H), 3.93 (dd, J=7.3, 1.3 Hz, 3H), 2.65 (dd, J=3.7, 1.3 Hz, 3H), 2.43 (q, J=6.8 Hz, 2H), 2.18 (p, J=7.1 Hz, 2H), 1.33 (td, J=7.2, 1.3 Hz, 3H).

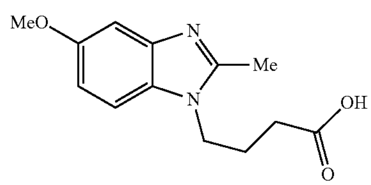 [SMILES: COc1ccc2c(c1)nc(C)n2CCCC(=O)O]

Intermediate 1.30b was prepared analogously to the general procedure, step 2 (Example 1). Yield=100%; m=676 mg; $^1$H NMR (400 MHz, Methanol-d$_4$) δ 7.54 (dd, J=32.8, 8.9 Hz, 1H), 7.18 (dd, J=33.3, 2.4 Hz, 1H), 7.01 (ddd, J=21.3, 8.9, 2.3 Hz, 1H), 4.33 (q, J=6.8, 6.3 Hz, 2H), 3.92-3.84 (m, 3H), 2.70 (d, J=8.0 Hz, 3H), 2.43 (q, J=6.7 Hz, 2H), 2.12 (p, J=7.0 Hz, 2H).

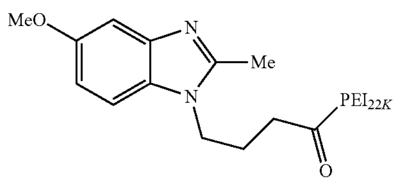

Product 1.30 was prepared analogously to the general procedure, step 3 (Example 1). Yield=100%; m=175 mg; $^1$H NMR (400 MHz, Deuterium Oxide) δ 7.80-6.57 (m, 3H), 4.44-2.96 (m, 22H), 2.80-1.38 (m, 7H).

Synthesis of Product 1.31

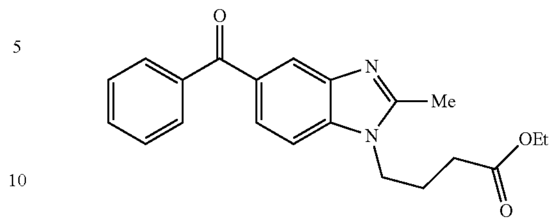

Intermediate 1.31a was prepared analogously to the general procedure, step 1 (Example 1). Yield=50%; m=820 mg; $^1$H NMR (400 MHz, Chloroform-d) δ 7.94-7.21 (m, 8H), 7.05 (d, J=1.3 Hz, 1H), 5.08 (d, J=1.3 Hz, 2H), 4.05 (td, J=8.1, 7.5, 2.9 Hz, 2H), 3.92 (dtd, J=16.2, 7.8, 6.5 Hz, 2H), 2.50 (dd, J=12.5, 1.4 Hz, 3H), 2.19 (q, J=6.3 Hz, 2H), 1.94 (p, J=7.0 Hz, 2H), 1.04 (ddd, J=14.3, 7.9, 6.5 Hz, 3H).

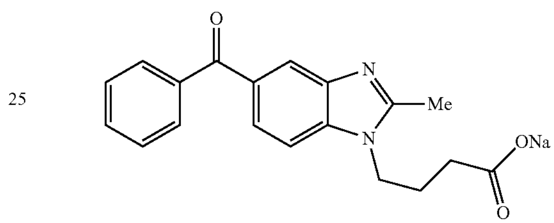

Intermediate 1.31b was prepared analogously to the general procedure, step 2 (Example 1). Yield=73%; m=580 mg; $^1$H NMR (400 MHz, Methanol-d$_4$) δ 8.01 (d, J=8.9 Hz, 1H), 7.83-7.48 (m, 7H), 4.34 (tt, J=7.3, 3.0 Hz, 2H), 2.71-2.65 (m, 2H), 2.41 (ddt, J=10.2, 7.4, 4.2 Hz, 2H), 2.12 (h, J=7.2 Hz, 2H).

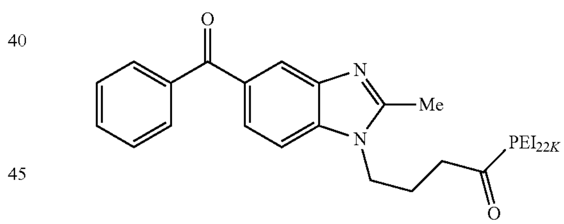

Product 1.31 was prepared analogously to the general procedure, step 3 (Example 1). Yield=84%; m=171 mg; $^1$H NMR (400 MHz, Deuterium Oxide) δ 7.92-6.49 (m, 8H), 4.50-3.10 (m, 17H), 3.03-1.78 (m, 7H).

Synthesis of Product 1.32

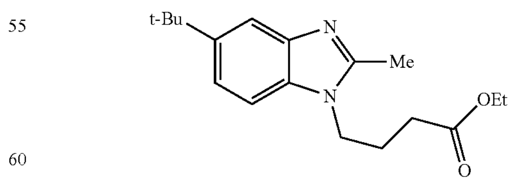

Intermediate 1.32a was prepared analogously to the general procedure, step 1 (Example 1). Yield=67%; m=1.29 mg; $^1$H NMR (400 MHz, Chloroform-d) δ 7.81-7.51 (m, 1H), 7.37-7.23 (m, 2H), 4.23-4.08 (m, 4H), 2.62 (d, J=4.3 Hz, 3H), 2.41-2.32 (m, 2H), 2.12 (pd, J=6.9, 2.4 Hz, 2H), 1.38 (d, J=6.9 Hz, 9H), 1.25 (td, J=7.2, 2.0 Hz, 3H).

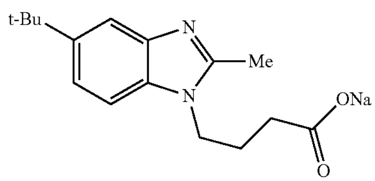

Intermediate 1.32b was prepared analogously to the general procedure, step 2 (Example 1). Yield=81%; m=1.02 mg; $^1$H NMR (400 MHz, DMSO-$d_6$) δ 7.48 (s, 1H), 7.41 (dd, J=8.5, 5.2 Hz, 1H), 7.23 (ddd, J=17.6, 8.5, 1.7 Hz, 1H), 4.16 (q, J=7.8 Hz, 2H), 2.50 (s, 3H), 2.26 (dt, J=13.7, 7.0 Hz, 2H), 1.90 (p, J=7.2 Hz, 2H), 1.33 (d, J=7.3 Hz, 9H).

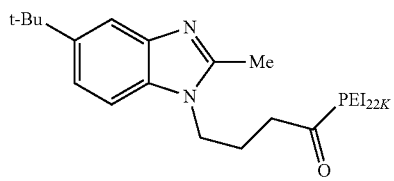

Product 1.32 was prepared analogously to the general procedure, step 3 (Example 1). Yield=97%; m=176 mg; $^1$H NMR (400 MHz, Deuterium Oxide) δ 7.80-7.04 (m, 3H), 4.49-4.04 (m, 2H), 3.94-2.93 (m, 15H), 2.81-2.27 (m, 5H), 2.17-1.70 (m, 2H), 1.46-0.82 (m, 9H).

Synthesis of Product 1.33

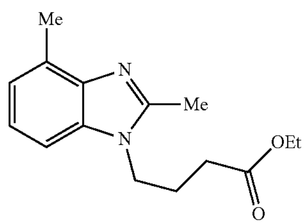 [SMILES: CCOC(=O)CCCn1c(C)nc2c(C)cccc21]

Intermediate 1.33a was prepared analogously to the general procedure, step 2 (Example 1). Yield=49%; m=1.72 g; $^1$H NMR (400 MHz, Chloroform-d) δ 7.30-7.18 (m, 2H), 7.14 (d, J=6.5 Hz, 1H), 4.31-4.22 (m, 3H), 4.25-4.17 (m, 1H), 2.75 (s, 6H), 2.57-2.41 (m, 2H), 2.21 (p, J=7.2 Hz, 2H), 1.35 (td, J=7.1, 1.8 Hz, 3H).

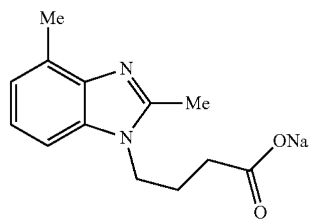

Intermediate 1.33b was prepared analogously to the general procedure, step 2 (Example 1). Yield=54%; m=920 mg; $^1$H NMR (400 MHz, Methanol-$d_4$) δ 7.38 (d, J=8.2 Hz, 1H), 7.19 (t, J=7.4 Hz, 1H), 7.07 (d, J=7.4 Hz, 1H), 4.28 (t, J=7.3 Hz, 2H), 3.33 (d, J=3.3 Hz, 2H), 2.66 (d, J=2.7 Hz, 3H), 2.58 (s, 3H), 2.37 (t, J=6.3 Hz, 2H), 2.08 (h, J=7.7 Hz, 2H).

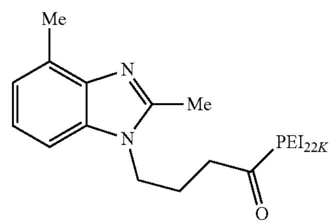

Product 1.33 was prepared analogously to the general procedure, step 3 (Example 1). Yield=100%; m=188 mg; $^1$H NMR (400 MHz, Deuterium Oxide) δ 7.62-6.76 (m, 3H), 4.46-3.03 (m, 15H), 2.87-1.36 (m, 10H).

Synthesis of Product 1.34

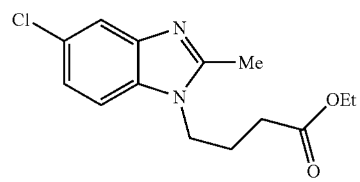 [SMILES: CCOC(=O)CCCn1c(C)nc2cc(Cl)ccc21]

Intermediate 1.34a was prepared analogously to the general procedure, step 1 (Example 1). Yield=91%; m=1.55 g; $^1$H NMR (400 MHz, Chloroform-d) δ 7.68-7.53 (m, 1H), 7.33-7.16 (m, 2H), 4.14 (pd, J=7.4, 1.6 Hz, 4H), 2.61 (d, J=1.5 Hz, 3H), 2.35 (td, J=6.9, 3.5 Hz, 2H), 2.09 (h, J=5.8, 4.7 Hz, 2H), 1.26 (tdd, J=6.9, 4.5, 1.5 Hz, 3H).

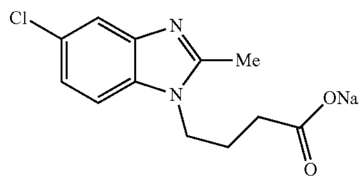

Intermediate 1.34b was prepared analogously to the general procedure, step 2 (Example 1). Yield=60%; m=840 mg; $^1$H NMR (400 MHz, Methanol-$d_4$) δ 7.85 (s, 1H), 7.75-7.60 (m, 1H), 7.45-7.38 (m, 1H), 4.39 (q, J=7.6, 6.5 Hz, 2H), 2.77 (t, J=2.9 Hz, 3H), 2.49 (t, J=6.6 Hz, 2H), 2.13 (p, J=7.3 Hz, 2H).

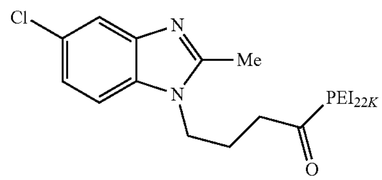

Product 1.34 was prepared analogously to the general procedure, step 3 (Example 1). Yield=100%; m=193 mg; $^1$H NMR (400 MHz, Deuterium Oxide) δ 7.83-6.65 (m, 3H), 4.52-3.09 (m, 15H), 3.04-2.32 (m, 5H), 2.30-1.72 (m, 2H).

Synthesis of Product 1.35

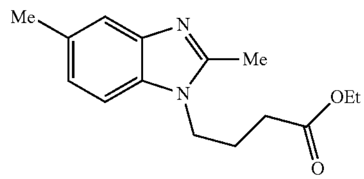 [SMILES: CCOC(=O)CCCn1c(C)nc2cc(C)ccc21]

Intermediate 1.35a was prepared analogously to the general procedure, step 1 (Example 1). Yield=63%; m=1.16 g; $^1$H NMR (400 MHz, Chloroform-d) δ 7.59-7.45 (m, 1H), 7.24-7.02 (m, 2H), 4.15 (td, J=8.5, 6.9, 5.0 Hz, 4H), 2.61 (d, J=3.7 Hz, 3H), 2.47 (d, J=8.6 Hz, 3H), 2.35 (td, J=6.8, 4.7 Hz, 2H), 2.17-2.05 (m, 2H), 1.25 (td, J=7.2, 3.0 Hz, 3H).

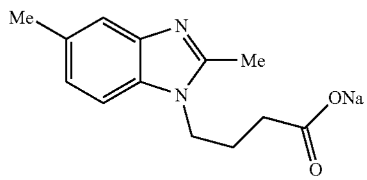

Intermediate 1.35b was prepared analogously to the general procedure, step 2 (Example 1). Yield=100%; m=1.07 g; $^1$H NMR (400 MHz, Methanol-d$_4$) δ 7.82-7.64 (m, 1H), 7.61-7.49 (m, 1H), 7.39 (t, J=10.2 Hz, 1H), 4.45 (tt, J=7.6, 3.2 Hz, 2H), 2.85 (d, J=3.2 Hz, 3H), 2.66-2.44 (m, 5H), 2.17 (p, J=7.7 Hz, 2H).

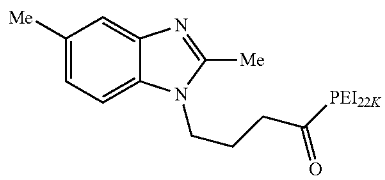

Product 1.35 was prepared analogously to the general procedure, step 3 (Example 1). Yield=100%; m=163 mg; $^1$H NMR (400 MHz, Deuterium Oxide) δ 7.61-6.56 (m, 3H), 4.43-3.06 (m, 20H), 2.88-1.52 (m, 10H).

Synthesis of Product 1.36

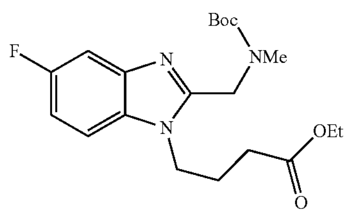 [SMILES: CCOC(=O)CCCn1c(CN(C)C(=O)OC(C)(C)C)nc2cc(F)ccc21]

Intermediate 1.36a was prepared analogously to the general procedure, step 1 (Example 1). Yield=100%; m=1.35 g; $^1$H NMR (400 MHz, Chloroform-d) δ 7.74-7.11 (m, 2H), 7.04 (dtd, J=18.1, 9.2, 2.4 Hz, 1H), 4.76 (s, 2H), 4.35-4.23 (m, 2H), 4.14 (qd, J=7.2, 2.9 Hz, 2H), 2.89 (d, J=3.5 Hz, 3H), 2.38 (t, J=7.1 Hz, 2H), 2.08-2.00 (m, 2H), 1.48 (s, 9H), 1.25 (s, 3H).

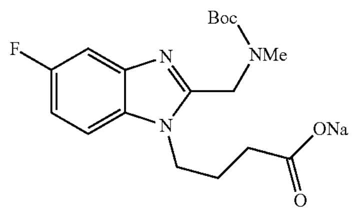

Intermediate 1.36b was prepared analogously to the general procedure, step 2 (Example 1). Yield=61%; m=810 mg; $^1$H NMR (400 MHz, Methanol-d$_4$) δ 7.61 (dd, J=8.2, 4.0 Hz, 1H), 7.37 (dd, J=30.5, 9.2 Hz, 1H), 7.08 (dt, J=22.3, 9.4 Hz, 1H), 4.77 (s, 2H), 4.32 (dt, J=14.4, 7.3 Hz, 2H), 2.95 (s, 3H), 2.40 (t, J=7.2 Hz, 2H), 2.05 (q, J=7.4 Hz, 2H), 1.47 (s, 9H).

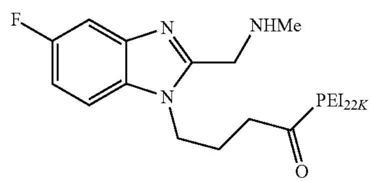

Product 1.36 was prepared analogously to the general procedure, step 3 (Example 1). Yield=98%; m=183 mg; $^1$H NMR (400 MHz, Deuterium Oxide) δ 7.77-6.66 (m, 3H), 4.73-4.51 (m, 2H), 4.47-3.01 (m, 17H), 2.99-2.78 (m, 3H), 2.73-1.70 (m, 4H).

Synthesis of Product 1.37

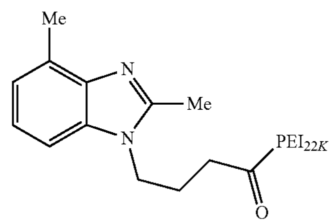

Product 1.37 was prepared analogously to the general procedure, step 3 (Example 1). Yield=93%; m=155 mg; $^1$H NMR (400 MHz, Deuterium Oxide) δ 7.54-6.54 (m, 3H), 4.39-2.94 (m, 15H), 2.93-1.52 (m, 10H).

Synthesis of Product 1.38

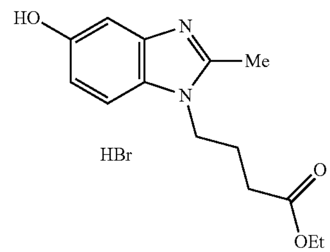 [SMILES: CCOC(=O)CCCn1c(C)nc2cc(O)ccc21 ; Br]

Intermediate 1.38a was prepared analogously to the general procedure, step 1 (Example 1). Yield=26%; m=300 mg; $^1$H NMR (400 MHz, Methanol-d$_4$) δ 7.30 (d, J=8.6 Hz, 1H), 6.96 (s, 1H), 6.80 (dd, J=8.8, 2.3 Hz, 1H), 4.21 (t, J=7.6 Hz, 2H), 4.07 (q, J=7.4 Hz, 1H), 3.62 (d, J=2.5 Hz, 1H), 2.56 (s, 3H), 2.41 (q, J=6.6 Hz, 2H), 2.09 (p, J=7.3 Hz, 2H), 1.21 (t, J=7.3 Hz, 2H).

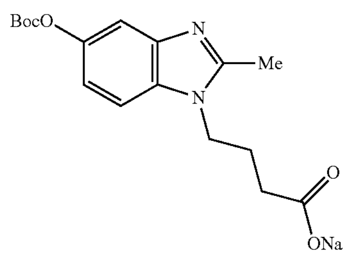

Intermediate 1.38b was prepared analogously to the general procedure, step 2 (Example 1). Yield=54%; m=68 mg; $^1$H NMR ($D_2O$) δ: $^1$H NMR (400 MHz, Methanol-$d_4$) δ 7.54 (dd, J=8.4, 3.1 Hz, 1H), 7.41-7.29 (m, 1H), 7.09-6.98 (m, 1H), 4.33-4.22 (m, 2H), 2.63 (s, 3H), 2.37 (t, J=6.9 Hz, 2H), 2.09 (p, J=7.1 Hz, 2H), 1.56 (s, 9H).

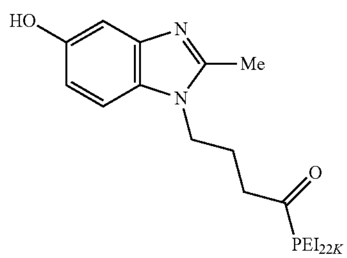

Product 1.38 was prepared analogously to the general procedure, step 3 (Example 1). Yield=100%; m=54 mg; $^1$H NMR (400 MHz, Deuterium Oxide) δ 7.80-6.40 (m, 4H), 4.35-1.30 (m, 22H).

Synthesis of Product 1.39

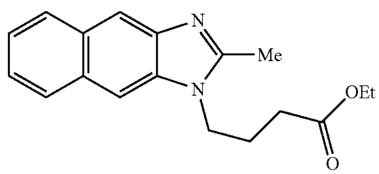 [SMILES: CCOC(=O)CCCn1c(C)nc2cc3ccccc3cc21]

Intermediate 1.39a was prepared analogously to the general procedure, step 2 (Example 1). Yield=70%; m=1.6 g; $^1$H NMR (400 MHz, Chloroform-d) δ 8.00 (s, 1H), 7.88-7.81 (m, 1H), 7.81-7.75 (m, 1H), 7.52 (s, 1H), 7.26 (ddt, J=8.4, 6.7, 4.2 Hz, 2H), 4.11-3.96 (m, 4H), 2.52 (s, 3H), 2.24 (t, J=6.8 Hz, 2H), 2.02 (p, J=7.1 Hz, 2H), 1.11 (td, J=7.1, 1.6 Hz, 3H).

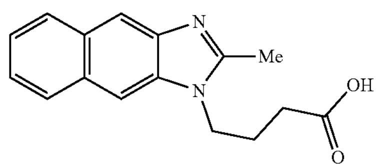 [SMILES: Cc1nc2cc3ccccc3cc2n1CCCC(=O)O]

Intermediate 1.39b was prepared analogously to the general procedure, step 2 (Example 1). Yield=58%; m=840 mg; $^1$H NMR (400 MHz, DMSO-$d_6$) δ 12.27 (s, 1H), 8.10 (s, 1H), 8.04 (s, 1H), 8.05-7.95 (m, 2H), 7.47-7.34 (m, 2H), 4.31 (t, J=7.5 Hz, 2H), 2.66 (s, 3H), 2.37 (t, J=7.2 Hz, 2H), 2.03 (p, J=7.3 Hz, 2H).

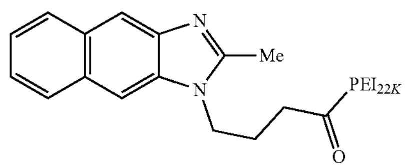

Product 1.39 was prepared analogously to the general procedure, step 3 (Example 1). Yield=95%; m=174 mg; $^1$H NMR (400 MHz, Deuterium Oxide) δ 8.21-6.03 (m, 6H), 4.47-0.63 (m, 22H).

Synthesis of Product 1.40

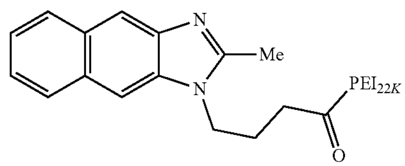

Product 1.40 was prepared analogously to the general procedure, step 3 (Example 1). Yield=97%; m=198 mg; $^1$H NMR (400 MHz, Deuterium Oxide) δ 8.19-6.14 (m, 6H), 4.51-0.73 (m, 24H).

Synthesis of Product 1.41

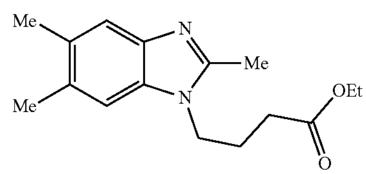 [SMILES: CCOC(=O)CCCn1c(C)nc2cc(C)c(C)cc21]

Intermediate 1.41a was prepared analogously to the general procedure, step 2 (Example 1). Yield=45%; m=1.3 g; $^1$H NMR (400 MHz, Chloroform-d) δ 7.63 (s, 1H), 7.26 (s, 1H), 4.33 (q, J=7.2 Hz, 4H), 2.77 (s, 3H), 2.58-2.49 (m, 8H), 2.29 (p, J=7.2 Hz, 2H), 1.44 (td, J=7.2, 1.5 Hz, 3H).

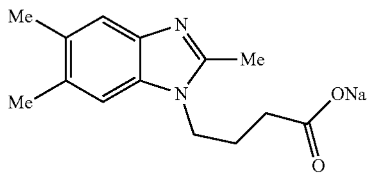

Intermediate 1.41b was prepared analogously to the general procedure, step 2 (Example 1). Yield=79%; m=1.0 g; $^1$H NMR (400 MHz, Methanol-$d_4$) δ 7.34 (s, 2H), 4.28-4.19 (m, 2H), 2.61 (s, 3H), 2.43-2.30 (m, 8H), 2.08 (p, J=7.9 Hz, 2H).

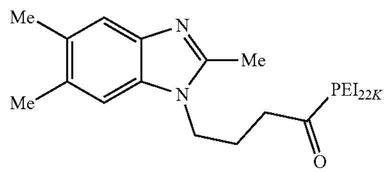

Product 1.41 was prepared analogously to the general procedure, step 3 (Example 1). Yield=99%; m=161 mg; $^{1}$H NMR (400 MHz, Deuterium Oxide) δ 7.55-6.76 (m, 2H), 4.53-2.95 (m, 20H), 2.89-2.39 (m, 5H), 2.36-1.49 (m, 8H).

Synthesis of Product 1.42

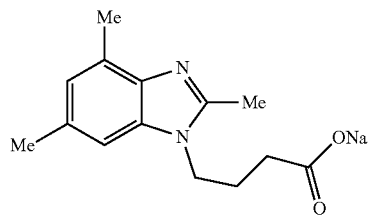

Intermediate 1.42a was prepared analogously to the general procedure, step 2 (Example 1). Yield=53%; m=418 mg; $^{1}$H NMR (400 MHz, Deuterium Oxide) δ 6.98 (s, 1H), 6.82 (s, 1H), 3.90 (t, J=7.3 Hz, 2H), 2.41 (s, 3H), 2.37 (s, 3H), 2.30 (s, 3H), 2.08-2.01 (m, 2H), 1.94-1.77 (m, 2H).

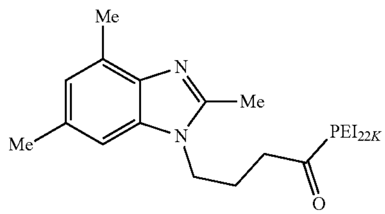

Product 1.42 was prepared analogously to the general procedure, step 3 (Example 1). Yield=84%; m=25 mg; $^{1}$H NMR (400 MHz, Deuterium Oxide) δ 7.48-6.58 (m, 2H), 4.48-3.14 (m, 25H), 2.95-1.67 (m, 12H).

Synthesis of Product 1.43

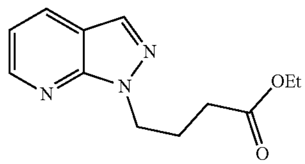 [SMILES: CCOC(=O)CCCn1ncc2cccnc21]

Intermediate 1.43a was prepared analogously to the general procedure, step 1 (Example 1). Yield=75%; m=1.05 g; $^{1}$H NMR (400 MHz, Chloroform-d) δ 8.51 (dd, J=4.5, 1.6 Hz, 1H), 8.05 (dd, J=8.0, 1.6 Hz, 1H), 8.00 (s, 1H), 7.10 (dd, J=8.0, 4.5 Hz, 1H), 4.64-4.56 (m, 2H), 4.07 (q, J=7.1 Hz, 2H), 2.36-2.22 (m, 4H), 1.19 (t, J=7.2 Hz, 3H).

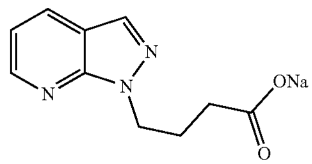

Intermediate 1.43b was prepared analogously to the general procedure, step 2 (Example 1). Yield=76%; m=778 mg; $^{1}$H NMR (400 MHz, Deuterium Oxide) δ 8.30-8.22 (m, 1H), 8.06-7.96 (m, 1H), 7.90-7.81 (m, 1H), 7.09-7.01 (m, 1H), 4.23 (t, J=6.4 Hz, 2H), 2.04-1.89 (m, 4H).

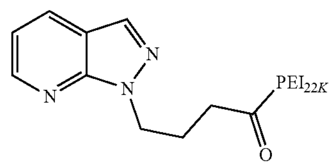

Product 1.43 was prepared analogously to the general procedure, step 3 (Example 1). Yield=81%; m=94 mg; $^{1}$H NMR (400 MHz, Deuterium Oxide) δ 8.35-6.54 (m, 4H), 4.52-2.63 (m, 9H), 2.59-1.42 (m, 4H).

Synthesis of Product 1.44

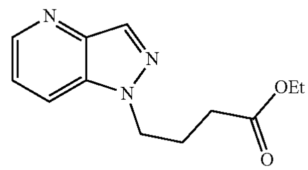 [SMILES: CCOC(=O)CCCn1ncc2ncccc21]

Intermediate 1.44a was prepared analogously to the general procedure, step 1 (Example 1). Yield=15%; m=211 mg; $^{1}$H NMR (400 MHz, Chloroform-d) δ 8.52 (dd, J=4.4, 1.3 Hz, 1H), 8.19 (d, J=1.0 Hz, 1H), 7.77 (dt, J=8.5, 1.2 Hz, 1H), 7.24 (dd, J=8.6, 4.4 Hz, 1H), 4.46-4.38 (m, 2H), 4.04 (q, J=7.2 Hz, 2H), 2.28-2.13 (m, 4H), 1.17 (t, J=7.1 Hz, 3H).

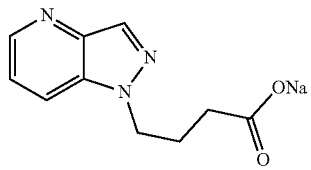

Intermediate 1.44b was prepared analogously to the general procedure, step 2 (Example 1). Yield=100%; m=887 mg; $^{1}$H NMR (400 MHz, Deuterium Oxide) δ δ 8.24 (dd, J=4.5, 1.3 Hz, 1H), 7.92 (d, J=1.0 Hz, 1H), 7.76 (dt, J=8.7, 1.2 Hz, 1H), 7.20 (dd, J=8.7, 4.4 Hz, 1H), 4.21-4.13 (m, 2H), 2.02-1.87 (m, 4H).

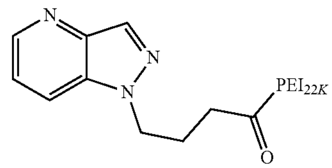

Product 1.44 was prepared analogously to the general procedure, step 3 (Example 1). Yield=97%; m=103 mg; $^{1}$H NMR (400 MHz, Deuterium Oxide) δ 8.92-7.42 (m, 4H), 4.61-4.25 (m, 2H), 4.04-3.09 (m, 10H), 2.67-1.88 (m, 5H).

Synthesis of Product 1.45

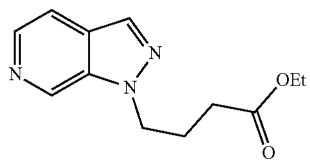 [SMILES: CCOC(=O)CCCn1ncc2ccncc21]

Intermediate 1.45a was prepared analogously to the general procedure, step 1 (Example 1). Yield=43%; m=602 mg; $^1$H NMR (400 MHz, Chloroform-d) δ 9.00 (s, 1H), 8.29 (d, J=5.6 Hz, 1H), 8.04 (d, J=0.8 Hz, 1H), 7.61 (dd, J=5.6, 1.3 Hz, 1H), 4.61-4.52 (m, 2H), 4.09 (q, J=7.1 Hz, 2H), 2.34-2.21 (m, 4H), 1.20 (t, J=7.1 Hz, 3H).

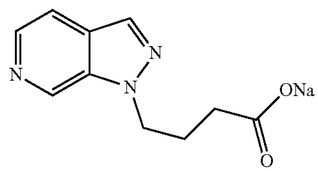

Intermediate 1.45b was prepared analogously to the general procedure, step 2 (Example 1). Yield=100%; m=592 mg; $^1$H NMR (400 MHz, Deuterium Oxide) δ 8.77 (s, 1H), 8.04-7.93 (m, 2H), 7.57 (dd, J=5.8, 1.3 Hz, 1H), 4.37-4.29 (m, 2H), 2.07-1.93 (m, 4H).

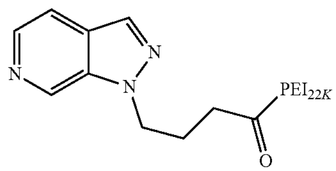

Product 1.45 was prepared analogously to the general procedure, step 3 (Example 1). Yield=100%; m=84 mg; $^1$H NMR (400 MHz, Deuterium Oxide) δ 9.67-8.10 (m, 4H), 4.23-3.06 (m, 16H), 2.86-1.90 (m, 4H).

Synthesis of Product 1.46

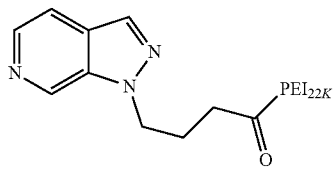

Product 1.46 was prepared analogously to the general procedure, step 3 (Example 1). Yield=89%; m=68 mg; $^1$H NMR (400 MHz, Deuterium Oxide) δ 8.63-6.72 (m, 4H), 4.57-2.78 (m, 20H), 2.75-1.47 (m, 4H).

Synthesis of Product 1.47

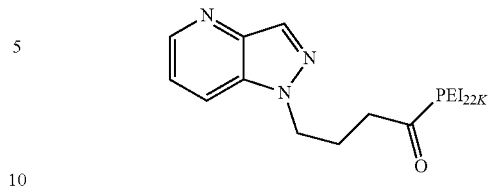

Product 1.47 was prepared analogously to the general procedure, step 3 (Example 1). Yield=97%; m=73 mg; $^1$H NMR (400 MHz, Deuterium Oxide) δ 9.12-7.56 (m, 4H), 4.58-4.36 (m, 2H), 4.09-3.01 (m, 19H), 2.90-1.77 (m, 4H).

Synthesis of Product 1.48

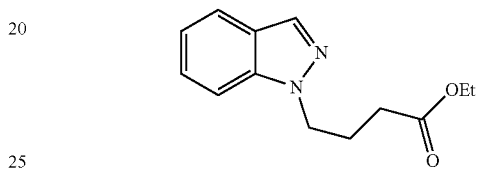

Intermediate 1.48a was prepared analogously to the general procedure, step 1 (Example 1). Yield=59%; m=820 mg; $^1$H NMR (400 MHz, Chloroform-d) δ 7.84 (s, 1H), 7.57 (dt, J=8.2, 1.1 Hz, 1H), 7.27 (dd, J=8.5, 1.1 Hz, 1H), 7.28-7.18 (m, 1H), 6.98 (ddd, J=8.0, 6.6, 1.1 Hz, 1H), 4.31 (t, J=6.5 Hz, 2H), 3.94 (q, J=7.1 Hz, 2H), 2.18-2.03 (m, 4H), 1.06 (t, J=7.1 Hz, 3H).

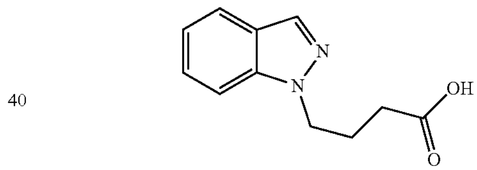

Intermediate 1.48b was prepared analogously to the general procedure, step 2 (Example 1). Yield=100%; m=175 mg; $^1$H NMR (400 MHz, Methanol-$d_4$) δ 8.01 (s, 1H), 7.74 (dt, J=8.2, 1.0 Hz, 1H), 7.59 (dq, J=8.5, 0.9 Hz, 1H), 7.40 (ddd, J=8.6, 6.9, 1.1 Hz, 1H), 7.15 (ddd, J=7.9, 6.8, 0.8 Hz, 1H), 4.52-4.44 (m, 2H), 2.28-2.12 (m, 4H).

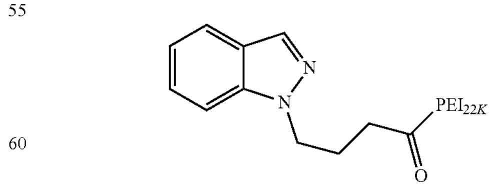

Product 1.48 was prepared analogously to the general procedure, step 3 (Example 1). Yield=83%; m=105 mg; $^1$H NMR (400 MHz, Deuterium Oxide) δ 8.18-6.91 (m, 5H), 4.14-1.72 (m, 42H).

Synthesis of Product 1.49

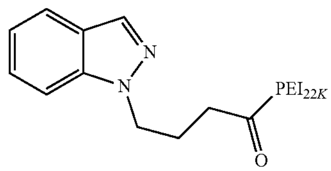

Product 1.49 was prepared analogously to the general procedure, step 3 (Example 1). Yield=52%; m=39 mg; $^1$H NMR (400 MHz, Deuterium Oxide) δ 8.21-6.38 (m, 5H), 4.47-1.37 (m, 25H).

Synthesis of Product 1.50

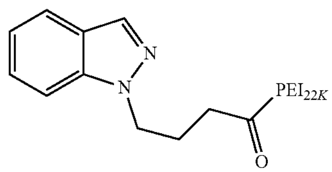

Product 1.50 was prepared analogously to the general procedure, step 3 (Example 1). Yield=16%; m=13 mg; $^1$H NMR (400 MHz, Deuterium Oxide) δ 8.19-6.27 (m, 5H), 4.42-1.05 (m, 23H).

Synthesis of Product 1.51

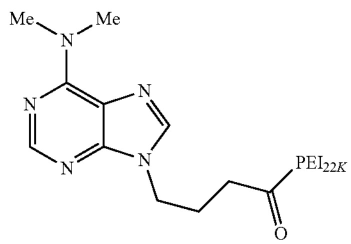

Product 1.51 was prepared analogously to the general procedure, step 3 (Example 1). Yield=91%; m=12 mg; $^1$H NMR (400 MHz, Deuterium Oxide) δ 8.65-7.82 (m, 2H), 4.39-2.88 (m, 36H), 2.68-1.91 (m, 3H).

Synthesis of Product 1.52

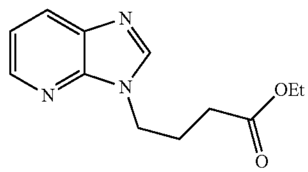 [SMILES: CCOC(=O)CCCn1cnc2cccnc21]

Intermediate 1.52a was prepared analogously to the general procedure, step 1 (Example 1). Yield=76%; m=440 mg; $^1$H NMR (400 MHz, Chloroform-d) δ 8.40 (dd, J=4.8, 1.6 Hz, 1H), 8.18 (s, 1H), 8.07 (dd, J=8.1, 1.6 Hz, 1H), 7.30-7.20 (m, 1H), 4.40 (td, J=6.9, 1.7 Hz, 2H), 4.10 (q, J=7.1 Hz, 2H), 2.43-2.20 (m, 4H), 1.22 (td, J=7.2, 0.6 Hz, 3H).

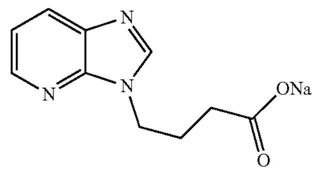

Intermediate 1.52b was prepared analogously to the general procedure, step 2 (Example 1). Yield=50%; m=597 mg; $^1$H NMR (400 MHz, Deuterium Oxide) δ 8.12 (s, 1H), 8.09 (dd, J=4.9, 1.4 Hz, 1H), 7.85 (dd, J=8.1, 1.4 Hz, 1H), 7.14 (dd, J=8.1, 4.9 Hz, 1H), 4.08 (t, J=7.0 Hz, 2H), 2.27-1.73 (m, 4H).

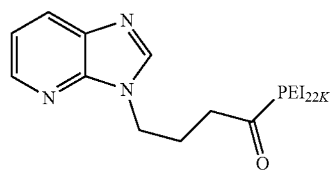

Product 1.52 was prepared analogously to the general procedure, step 3 (Example 1). Yield=71%; m=12 mg; $^1$H NMR (400 MHz, Deuterium Oxide) δ 9.59-6.98 (m, 4H), 4.13-2.68 (m, 17H), 2.68-0.79 (m, 3H).

Synthesis of Product 1.53

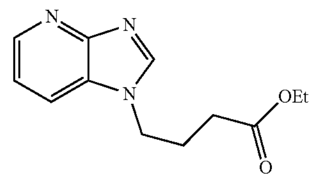 [SMILES: CCOC(=O)CCCn1cnc2ncccc21]

Intermediate 1.53a was prepared analogously to the general procedure, step 1 (Example 1). Yield=65%; m=153 mg; $^1$H NMR (400 MHz, Chloroform-d) δ 8.57 (dd, J=4.8, 1.5 Hz, 1H), 8.25 (s, 1H), 7.84 (dd, J=8.1, 1.5 Hz, 1H), 7.28-7.22 (m, 1H), 4.32 (t, J=7.2 Hz, 2H), 4.12 (q, J=7.1 Hz, 2H), 2.37-2.28 (m, 2H), 2.25-2.12 (m, 2H), 1.23 (t, J=7.1 Hz, 3H).

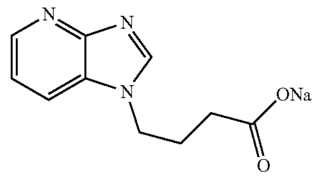

Intermediate 1.53b was prepared analogously to the general procedure, step 2 (Example 1). Yield=100%; m=105 mg; $^1$H NMR (400 MHz, Deuterium Oxide) δ δ 8.41 (dd, J=4.9, 1.5 Hz, 1H), 8.38 (s, 1H), 8.08 (dd, J=8.2, 1.5 Hz, 1H), 7.38 (dd, J=8.2, 4.9 Hz, 1H), 4.31 (t, J=6.9 Hz, 2H), 2.25-2.06 (m, 4H).

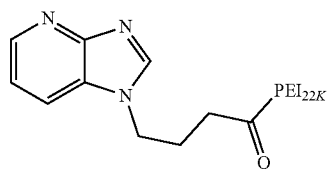

Product 1.53 was prepared analogously to the general procedure, step 3 (Example 1). Yield=82%; m=12 mg; $^1$H NMR (400 MHz, Deuterium Oxide) δ 9.47-6.92 (m, 4H), 4.19-2.88 (m, 20H), 2.92-1.60 (m, 4H).

Synthesis of Product 1.54

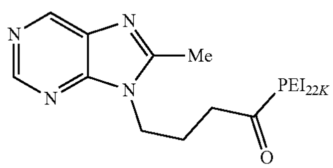

Product 1.54 was prepared analogously to the general procedure, step 3 (Example 1). Yield=83%; m=12 mg; $^1$H NMR (400 MHz, Deuterium Oxide) δ 9.20-8.32 (m, 2H), 4.51-2.93 (m, 16H), 2.88-1.68 (m, 7H).

Synthesis of Product 1.55

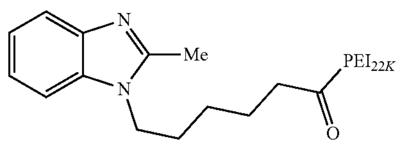

Product 1.55 was prepared analogously to the general procedure, step 3 (Example 1). Yield=97%; m=169 mg; $^1$H NMR (400 MHz, Deuterium Oxide) δ 7.74-7.19 (m, 4H), 4.41-3.00 (m, 13H), 2.83-2.52 (m, 3H), 2.48-1.99 (m, 2H), 1.95-1.00 (m, 6H).

Synthesis of Product 1.56

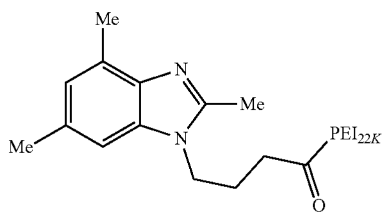

Product 1.56 was prepared analogously to the general procedure, step 3 (Example 1). Yield=100%; m=187 mg; $^1$H NMR ($D_2O$) δ: 7.41-6.35 (m, 2H), 4.44-2.96 (m, 23H), 2.85-1.34 (m, 20H).

Synthesis of Product 1.57

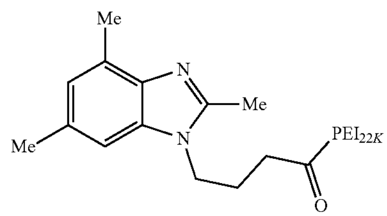

Product 1.57 was prepared analogously to the general procedure, step 3 (Example 1). Yield=100%; m=26 mg; $^1$H NMR (400 MHz, Deuterium Oxide) δ 7.64-6.35 (m, 2H), 4.50-3.01 (m, 62H), 3.05-1.41 (m, 13H).

Synthesis of Product 1.58

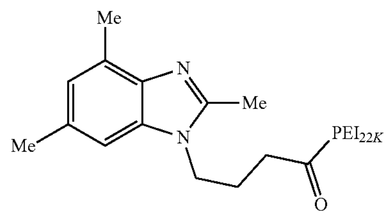

Product 1.58 was prepared analogously to the general procedure, step 3 (Example 1). Yield=72%; m=19 mg; $^1$H NMR (400 MHz, Deuterium Oxide) δ 7.55-6.59 (m, 2H), 4.41-3.11 (m, 39H), 3.05-1.37 (m, 13H).

Synthesis of Product 1.59

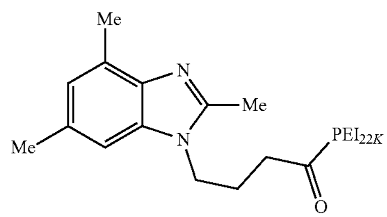

Product 1.59 was prepared analogously to the general procedure, step 3 (Example 1). Yield=70%; m=22 mg; $^1$H NMR (400 MHz, Deuterium Oxide) δ 7.80-6.15 (m, 2H), 4.50-3.21 (m, 22H), 3.17-0.97 (m, 13H).

Synthesis of Product 1.60

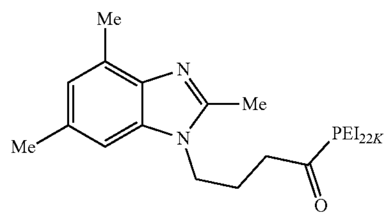

Product 1.60 was prepared analogously to the general procedure, step 3 (Example 1). Yield=73%; m=23 mg; $^1$H NMR (400 MHz, Deuterium Oxide) δ 7.98-6.15 (m, 2H), 4.62-3.06 (m, 22H), 2.99-1.39 (m, 13H).

Synthesis of Product 1.61

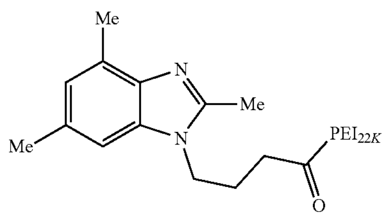

Product 1.61 was prepared analogously to the general procedure, step 3 (Example 1). Yield=84%; m=25 mg; $^1$H NMR (400 MHz, Deuterium Oxide) δ 7.64-6.35 (m, 2H), 4.57-3.13 (m, 25H), 3.13-1.50 (m, 13H).

Synthesis of Product 1.62

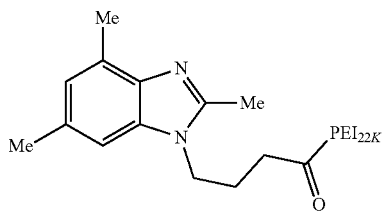

Product 1.62 was prepared analogously to the general procedure, step 3 (Example 1). Yield=68%; m=21 mg; $^1$H NMR (400 MHz, Deuterium Oxide) δ 7.74-6.35 (m, 2H), 4.50-3.01 (m, 24H), 2.97-1.41 (m, 13H).

Synthesis of Product 1.63

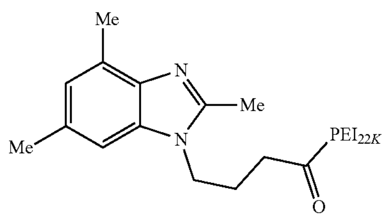

Product 1.63 was prepared analogously to the general procedure, step 3 (Example 1). Yield=35%; m=13 mg; $^1$H NMR (400 MHz, Deuterium Oxide) δ 7.62-6.39 (m, 2H), 4.57-3.01 (m, 16H), 2.90-1.21 (m, 13H).

Synthesis of Product 1.64

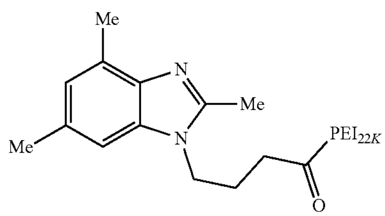

Product 1.64 was prepared analogously to the general procedure, step 3 (Example 1). Yield=85%; m=18 mg; $^1$H NMR (400 MHz, Deuterium Oxide) δ 7.90-6.11 (m, 2H), 4.52-3.09 (m, 30H), 3.11-1.39 (m, 13H).

Synthesis of Product 1.65

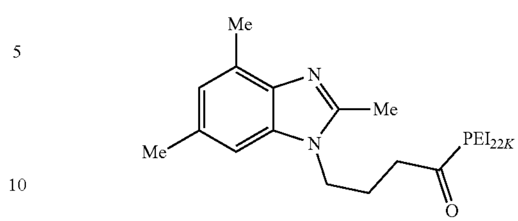

Product 1.65 was prepared analogously to the general procedure, step 3 (Example 1). Yield=84%; m=21 mg; $^1$H NMR (400 MHz, Deuterium Oxide) δ 7.80-6.15 (m, 2H), 4.60-3.17 (m, 19H), 3.09-1.25 (m, 13H).

Synthesis of Product 1.66

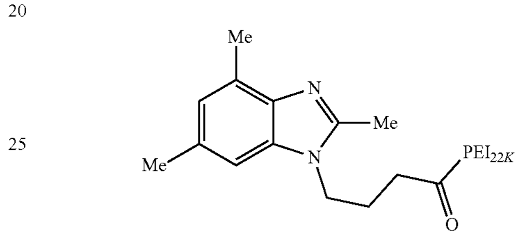

Product 1.66 was prepared analogously to the general procedure, step 3 (Example 1). Yield=72%; m=17 mg; $^1$H NMR (400 MHz, Deuterium Oxide) δ 7.49-6.19 (m, 2H), 4.57-3.05 (m, 13H), 3.03-1.37 (m, 4H).

Synthesis of Product 1.67

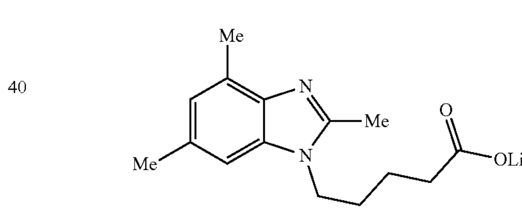

Intermediate 1.67a was prepared analogously to the general procedure, step 1 (Example 1). Yield=85%; m=395 mg; $^1$H NMR (400 MHz, Deuterium Oxide) δ 6.93 (d, J=1.5 Hz, 1H), 6.80 (s, 1H), 3.84 (t, J=7.3 Hz, 2H), 2.40 (s, 3H), 2.37 (s, 3H), 2.30 (s, 3H), 2.07 (t, J=7.4 Hz, 2H), 1.64-1.53 (m, 2H), 1.51-1.35 (m, 2H).

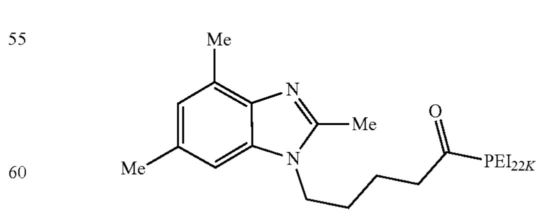

Product 1.67 was prepared analogously to the general procedure, step 3 (Example 1). Yield=69%; m=22 mg; $^1$H NMR (400 MHz, Deuterium Oxide) δ 7.64-6.35 (m, 2H), 4.52-3.01 (m, 25H), 2.94-1.02 (m, 13H).

Synthesis of Product 1.68

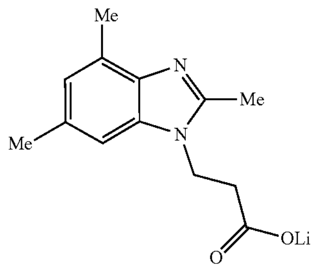

Intermediate 1.68a was prepared analogously to the general procedure, step 2 (Example 1). Yield=66%; m=247 mg; $^1$H NMR (400 MHz, Deuterium Oxide) δ 7.03 (s, 1H), 6.83 (s, 1H), 4.19 (t, 2H), 2.48 (t, J=7.7, 6.8 Hz, 2H), 2.43 (s, 3H), 2.35 (s, 3H), 2.29 (s, 3H).

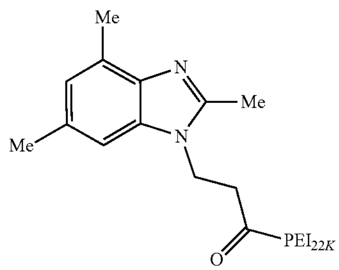

Product 1.68 was prepared analogously to the general procedure, step 3 (Example 1). Yield=74%; m=24 mg; $^1$H NMR (400 MHz, Deuterium Oxide) δ 7.80-6.25 (m, 2H), 4.52-1.32 (m, 33H).

Synthesis of Product 1.69

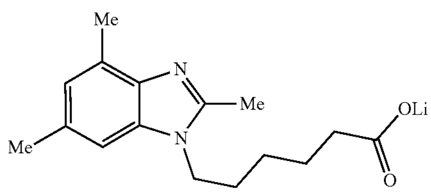

Intermediate 1.69a was prepared analogously to the general procedure, step 1 (Example 1). Yield=76%; m=332 mg; $^1$H NMR (400 MHz, Deuterium Oxide) δ 6.82 (s, 1H), 6.71 (s, 1H), 3.69 (t, J=7.3 Hz, 2H), 2.31 (d, J=2.5 Hz, 6H), 2.22 (s, 3H), 1.99 (q, J=7.7 Hz, 2H), 1.54-1.41 (m, 2H), 1.40-1.30 (m, 2H), 1.14-0.98 (m, 2H).

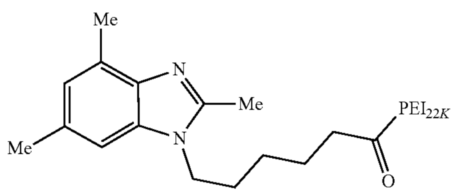

Product 1.69 was prepared analogously to the general procedure, step 3 (Example 1). Yield=74%; m=30 mg; $^1$H NMR (400 MHz, Deuterium Oxide) δ 7.48-6.39 (m, 2H), 4.46-3.01 (m, 18H), 2.88-0.77 (m, 13H).

Synthesis of Product 1.70

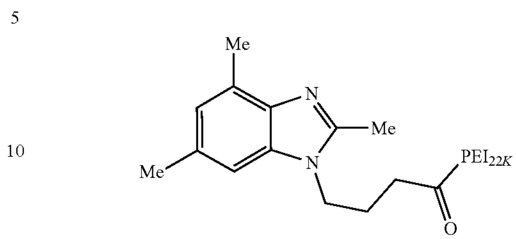

Product 1.70 was prepared analogously to the general procedure, step 3 (Example 1). Yield=63%; m=20 mg; $^1$H NMR (400 MHz, Deuterium Oxide) δ 7.72-6.29 (m, 2H), 4.48-3.21 (m, 24H), 3.09-1.19 (m, 13H).

Synthesis of Product 1.71

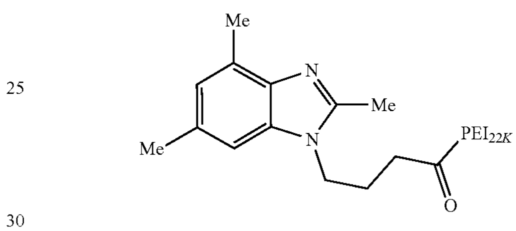

Product 1.71 was prepared analogously to the general procedure, step 3 (Example 1). Yield=80%; m=28 mg; $^1$H NMR (400 MHz, Deuterium Oxide) δ 7.62-6.31 (m, 2H), 4.43-3.09 (m, 18H), 3.01-0.82 (m, 15H).

Synthesis of Product 1.72

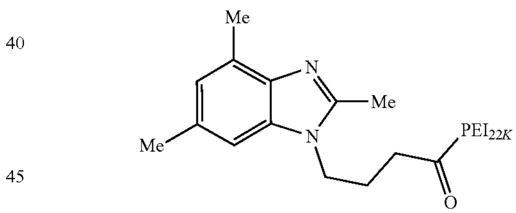

Product 1.72 was prepared analogously to the general procedure, step 3 (Example 1). Yield=86%; m=30 mg; $^1$H NMR (400 MHz, Deuterium Oxide) δ 7.55-6.25 (m, 2H), 4.55-3.06 (m, 17H), 2.94-1.23 (m, 13H).

Synthesis of Product 1.73

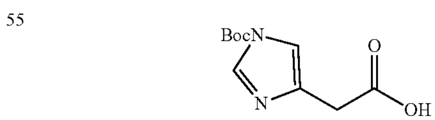

1.73a: 4-DMAP and $Et_3N$ were added to a solution of 4-imidazoleacetic acid in THF/$H_2O$. $Boc_2O$ in THE was then added at 0° C. and the mixture was stirred at rt overnight. EtOAc was added and HCl 3M was added to have the aqueous phase at pH 4. Aqueous phase was removed and organic phase was washed with brine. Dried over $Na_2SO_4$ and evaporated under vacuum to give the product as a white solid. Yield=54%; m=300 mg; $^1$H NMR (400 MHz, MeOD) δ 8.14 (d, J=1.4 Hz, 1H), 7.42 (d, J=1.4 Hz, 1H), 3.59 (s, 2H), 1.63 (s, 9H).

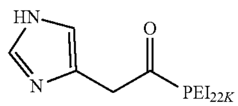

Product 1.73: In a microwave sealed tube was added PEI22k.HCl (1 eq) in water followed by NMM (2 eq). The acid was dissolved in MeOH and added to the PEI. After stirring 10 min, DMTMM was added and the mixture was stirred overnight at rt. Solvent were evaporated and co evaporation with ethanol was done. TFA was added at 0° C. and stirred for 3 h. TFA was evaporated and the product was purified on Amicon Ultra 15 (3 kD) with 6*10 mL HCl 50 mM.

Product 1.73. Yield=84%; m=58 mg; $^1$H NMR (400 MHz, Deuterium Oxide) δ 8.74-8.64 (m, 1H), 7.46-7.31 (m, 1H), 4.50-3.26 (m, 16H).

Synthesis of Product 1.74

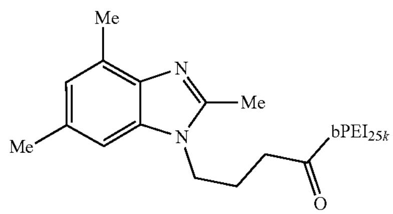

Product 1.74 was prepared analogously to the general procedure, step 3 using branched polyethyleneimine (bPEI, 25K, Sigma-Aldrich). Yield=94%; m=282 mg; $^1$H NMR (400 MHz, Deuterium Oxide) δ 7.42-6.52 (m, 2H), 4.45-1.51 (m, 33H).

Synthesis of Product 1.75

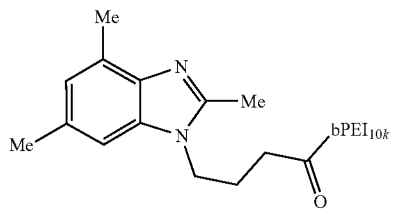

Product 1.75 was prepared analogously to the general procedure, step 3 using branched polyethyleneimine (bPEI, 10K, Alfa Aesar). Yield=99%; m=351 mg; $^1$H NMR (400 MHz, Deuterium Oxide) δ 7.37-6.50 (m, 2H), 4.57-1.44 (m, 29H).

Synthesis of Product 1.76

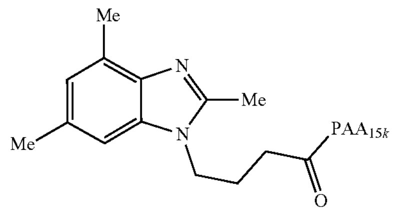

Product 1.76 was prepared analogously to the general procedure, step 3 using poly(allyamine) (PAA, 15K, Sigma-Aldrich). Yield=99%; m=146 mg; $^1$H NMR (400 MHz, Deuterium Oxide) δ 7.43-6.38 (m, 2H), 4.46-0.74 (m, 41H).

Synthesis of Product 1.77

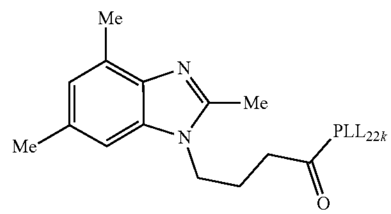

Product 1.77 was prepared analogously to the general procedure, step 3. Yield=34%; m=41 mg; $^1$H NMR (400 MHz, Deuterium Oxide) δ 7.44-6.93 (m, 2H), 4.53-4.06 (m, 5H), 3.15-1.08 (m, 40H).

Synthesis of Product 1.78

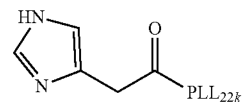

Product 1.78 was prepared analogously to the general procedure, step 4 using poly(vinylamine) (PLL, 22K, Sigma-Aldrich). Yield=99%; m=37 mg; $^1$H NMR (400 MHz, Deuterium Oxide) δ 7.74 (s, 1H), 7.03 (s, 1H), 4.43-4.09 (m, 2H), 3.75-2.85 (m, 11H), 2.66-2.41 (m, 4H), 2.03-0.88 (m, 14H).

Synthesis of Product 1.79

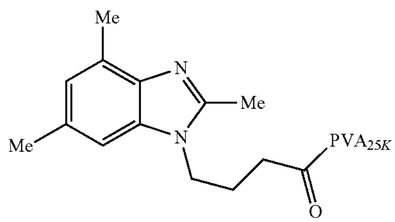

Product 1.79 was prepared analogously to the general procedure, step 3 using poly(vinylamine) (PVA, 25K, Polysciences). Yield=78%; m=139 mg; $^1$H NMR (400 MHz, Deuterium Oxide) δ 7.49-6.52 (m, 2H), 4.60-0.96 (m, 26H).

Synthesis of Product 1.80

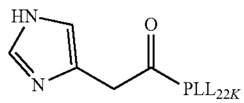

Product 1.80 was prepared analogously to the general procedure, step 4. Yield=98%; m=68 mg; $^1$H NMR (400 MHz, Deuterium Oxide) δ 8.63-8.50 (m, 1H), 7.36-7.27 (m, 1H), 4.34-4.17 (m, 1H), 3.79-3.66 (m, 2H), 3.63-2.84 (m, 7H), 2.59-2.15 (m, 3H), 1.90-1.15 (m, 9H).

Synthesis of Product 2.01

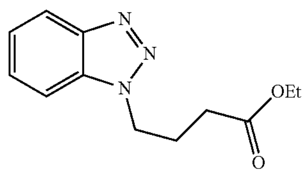 [SMILES: CCOC(=O)CCCn1nnc2ccccc21]

Intermediate 2.01a was prepared analogously to the general procedure, step 1 (Example 1). Yield=17%; m=1.00 g; $^1$H NMR (400 MHz, Chloroform-d) δ 7.95 (d, J=8.4 Hz, 1H), 7.45 (d, J=8.3 Hz, 1H), 7.38 (t, J=7.6 Hz, 1H), 7.30-7.22 (m, 1H), 4.68-4.57 (m, 2H), 4.01 (qd, J=7.1, 1.6 Hz, 2H), 2.30-2.16 (m, 4H), 1.13 (td, J=7.1, 1.6 Hz, 3H).

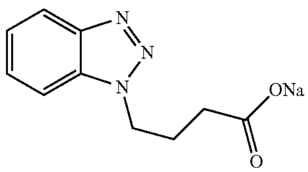

Intermediate 2.01b was prepared analogously to the general procedure, step 2 (Example 1). Yield=85%; m=830 mg; $^1$H NMR (400 MHz, Methanol-$d_4$) δ 8.03-7.96 (m, 1H), 7.82 (d, J=8.5 Hz, 1H), 7.58 (t, J=7.3 Hz, 1H), 7.45 (t, J=8.0 Hz, 1H), 4.80 (dt, J=7.0, 4.3 Hz, 2H), 2.37 (t, J=7.0 Hz, 2H), 2.30 (q, J=7.0 Hz, 2H).

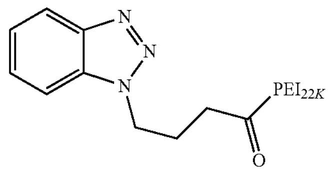

Product 2.01 was prepared analogously to the general procedure, step 3 (Example 1). Yield=100%; m=189 mg; $^1$H NMR (400 MHz, Deuterium Oxide) δ 7.41-6.55 (m, 4H), 4.58-3.02 (m, 14H), 2.90-1.31 (m, 3H).

Synthesis of Product 2.02

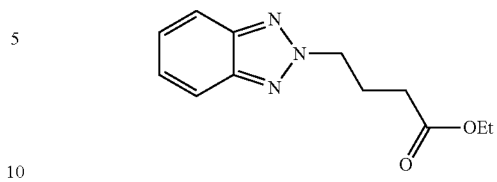

Intermediate 2.02a was prepared analogously to the general procedure, step 1 (Example 1). Yield=34%; m=2.00 g; $^1$H NMR (400 MHz, Chloroform-d) δ 7.73 (ddt, J=7.4, 4.1, 2.2 Hz, 2H), 7.25 (ddt, J=9.4, 4.0, 2.2 Hz, 2H), 4.68 (dd, J=7.3, 5.5 Hz, 2H), 3.99 (ddd, J=9.1, 7.2, 6.0 Hz, 2H), 2.40-2.12 (m, 4H), 1.11 (tt, J=7.3, 1.3 Hz, 3H).

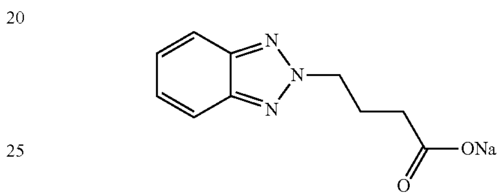

Intermediate 2.02b was prepared analogously to the general procedure, step 2 (Example 1). Yield=53%; m=1.00 g; $^1$H NMR (400 MHz, Methanol-$d_4$) δ 7.86 (dd, J=6.9, 3.4 Hz, 2H), 7.42 (dd, J=6.9, 3.4 Hz, 2H), 4.83 (d, J=13.0 Hz, 2H), 2.37 (d, J=4.3 Hz, 4H).

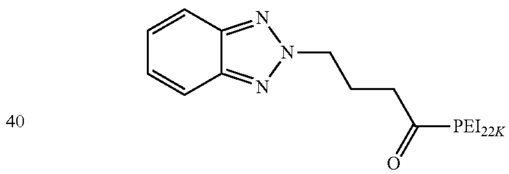

Product 2.02 was prepared analogously to the general procedure, step 3 (Example 1). Yield=100%; m=166 mg; $^1$H NMR (400 MHz, Deuterium Oxide) δ 7.83-6.50 (m, 4H), 4.61-3.90 (m, 2H), 3.88-2.51 (m, 11H), 2.49-1.35 (m, 4H).

Synthesis of Product 2.03

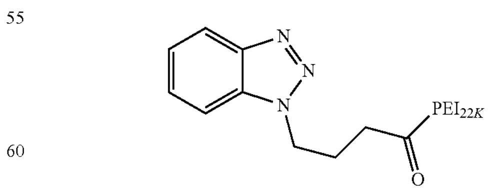

Product 2.03 was prepared analogously to the general procedure, step 3 (Example 1). Yield=93%; m=143 mg; $^1$H NMR (400 MHz, Deuterium Oxide) δ 7.95-6.76 (m, 4H), 4.57-4.09 (m, 2H), 3.96-2.52 (s, 17H), 2.45-1.61 (m, 4H).

Synthesis of Product 2.04

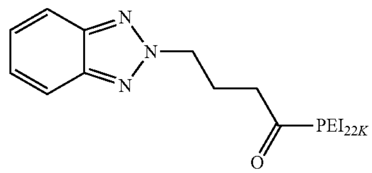

Product 2.04 was prepared analogously to the general procedure, step 3 (Example 1). Yield=92%; m=133 mg; $^1$H NMR (400 MHz, Deuterium Oxide) δ 7.98-6.60 (m, 4H), 4.67-4.17 (m, 2H), 4.15-2.69 (m, 18H), 2.52-1.45 (m, 4H).

Synthesis of Product 2.05

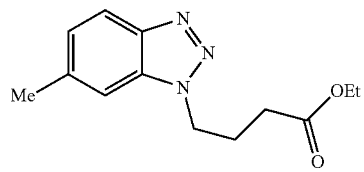 [SMILES: CCOC(=O)CCCn1nnc2ccc(C)cc21]

Intermediate 2.05a was prepared analogously to the general procedure, step 1 (Example 1). Yield=35%; m=1.94 g; $^1$H NMR (400 MHz, Chloroform-d) δ 7.87 (d, J=8.5 Hz, OH), 7.77 (s, OH), 7.40 (d, J=8.4 Hz, OH), 7.26 (s, 1H), 7.15 (d, J=8.5 Hz, 1H), 4.64 (q, J=6.7 Hz, 2H), 4.08 (qd, J=7.1, 2.4 Hz, 2H), 2.48 (dd, J=8.6, 1.9 Hz, 3H), 2.29 (pd, J=6.8, 2.2 Hz, 4H), 1.19 (td, J=7.2, 2.0 Hz, 3H).

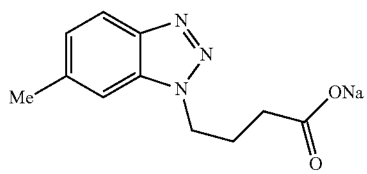

Intermediate 2.05b was prepared analogously to the general procedure, step 2 (Example 1). Yield=70%; m=1.53 g; $^1$H NMR (400 MHz, Methanol-$d_4$) δ 7.90-7.83 (m, 1H), 7.76 (s, OH), 7.70 (dd, J=8.8, 2.4 Hz, OH), 7.59 (s, 1H), 7.44 (d, J=8.7 Hz, OH), 7.31 (d, J=8.6 Hz, 1H), 4.77 (q, J=7.0 Hz, 2H), 3.33 (d, J=3.3 Hz, 2H), 2.56 (dd, J=13.3, 2.5 Hz, 3H), 2.36 (t, J=7.4 Hz, 2H), 2.30-2.22 (m, 2H).

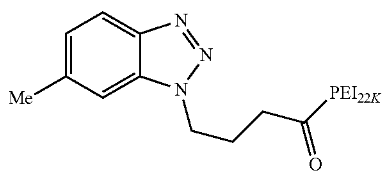

Product 2.05 was prepared analogously to the general procedure, step 3 (Example 1). Yield=86%; m=136 mg; $^1$H NMR (400 MHz, Deuterium Oxide) δ 8.02-6.48 (m, 3H), 4.61-4.10 (m, 2H), 4.05-2.81 (m, 17H), 2.47-1.49 (m, 7H).

Synthesis of Product 2.06

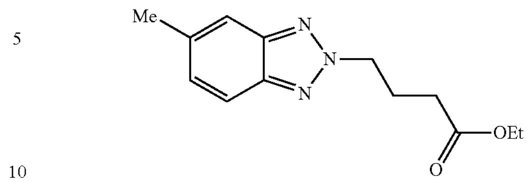

Intermediate 2.06a was prepared analogously to the general procedure, step 1 (Example 1). Yield=40%; m=2.23 g; $^1$H NMR (400 MHz, Chloroform-d) δ 7.77 (d, J=8.7 Hz, 1H), 7.63 (s, 1H), 7.25 (d, J=8.7 Hz, 1H), 4.81 (td, J=6.5, 1.9 Hz, 2H), 4.15 (qd, J=7.2, 2.0 Hz, 2H), 2.53 (s, 3H), 2.48-2.35 (m, 4H), 1.27 (td, J=7.1, 1.9 Hz, 3H).

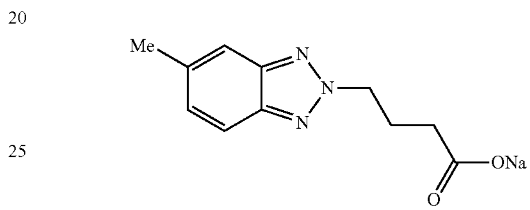

Intermediate 2.06b was prepared analogously to the general procedure, step 2 (Example 1). Yield=41%; m=793 mg; $^1$H NMR (400 MHz, Methanol-$d_4$) δ 7.74 (dd, J=8.9, 2.4 Hz, 1H), 7.61 (s, 1H), 7.28 (d, J=8.8 Hz, 1H), 4.78 (q, J=4.0 Hz, 2H), 3.33 (d, J=3.2 Hz, 1H), 2.50 (d, J=2.5 Hz, 3H), 2.36 (d, J=3.0 Hz, 4H).

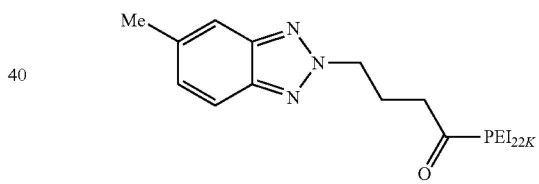

Product 2.06 was prepared analogously to the general procedure, step 3 (Example 1). Yield=85%; m=128 mg; $^1$H NMR (400 MHz, Deuterium Oxide) δ 7.92-6.35 (m, 3H), 4.66-4.20 (m, 2H), 4.11-2.83 (m, 17H), 2.67-1.45 (m, 7H).

Synthesis of Product 2.07

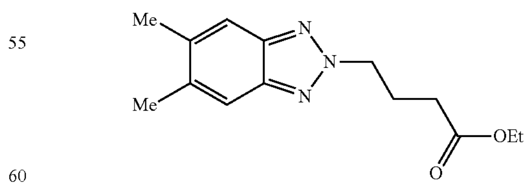

Intermediate 2.07a was prepared analogously to the general procedure, step 1 (Example 1). Yield=14%; m=538 mg; $^1$H NMR (400 MHz, Chloroform-d) δ 7.58 (s, 2H), 4.75 (t, J=6.4 Hz, 2H), 4.11 (q, J=7.0 Hz, 2H), 2.39 (s, 8H), 2.35 (d, J=6.4 Hz, 2H), 1.27-1.19 (m, 3H).

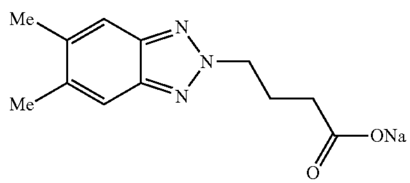

Intermediate 2.07b was prepared analogously to the general procedure, step 2 (Example 1). Yield=79%; m=416 mg; $^1$H NMR (400 MHz, Methanol-$d_4$) δ 7.59 (d, J=2.8 Hz, 2H), 4.75 (q, J=4.6 Hz, 2H), 3.33 (d, J=3.3 Hz, 1H), 2.41 (d, J=2.7 Hz, 6H), 2.33 (d, J=4.1 Hz, 4H).

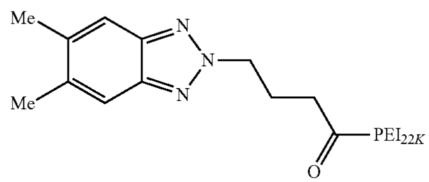

Product 2.07 was prepared analogously to the general procedure, step 3 (Example 1). Yield=49%; m=73 mg; $^1$H NMR (400 MHz, Deuterium Oxide) δ 7.34-6.60 (m, 2H), 4.68-4.19 (m, 2H), 4.07-2.84 (m, 18H), 2.69-1.33 (m, 10H).

Synthesis of Product 2.08

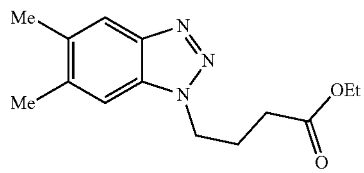 [SMILES: CCOC(=O)CCCn1nnc2cc(C)c(C)cc21]

Intermediate 2.08a was prepared analogously to the general procedure, step 1 (Example 1). Yield=12%; m=483 m; $^1$H NMR (400 MHz, Chloroform-d) δ 7.75 (s, 1H), 7.24 (d, J=13.6 Hz, 1H), 4.63 (t, J=6.4 Hz, 2H), 4.14-4.04 (m, 2H), 2.38 (d, J=10.2 Hz, 6H), 2.33-2.21 (m, 4H), 1.21 (td, J=7.2, 1.8 Hz, 3H).

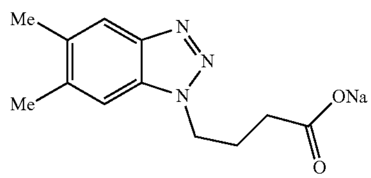

Intermediate 2.08b was prepared analogously to the general procedure, step 2 (Example 1). Yield=94%; m=444 mg; $^1$H NMR (400 MHz, Methanol-$d_4$) δ 7.72 (s, 1H), 7.56 (s, 1H), 4.73 (td, J=7.0, 2.2 Hz, 2H), 2.45 (dd, J=14.7, 2.7 Hz, 6H), 2.35 (t, J=7.2 Hz, 2H), 2.30-2.20 (m, 2H).

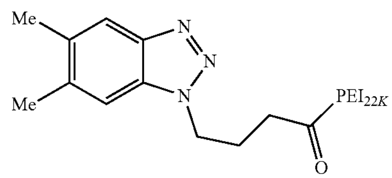

Product 2.08 was prepared analogously to the general procedure, step 3 (Example 1). Yield=81%; m=129 mg; $^1$H NMR (400 MHz, Deuterium Oxide) δ 7.79-6.33 (m, 2H), 4.55-3.99 (m, 2H), 3.93-2.78 (m, 18H), 2.67-1.22 (m, 10H).

Synthesis of Product 2.09

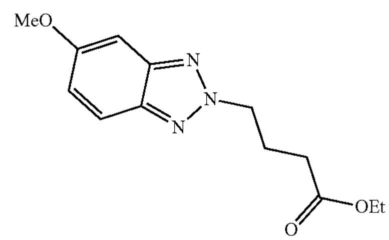

Intermediate 2.09a was prepared analogously to the general procedure, step 1 (Example 1). Yield=33%; m=2.22 g; $^1$H NMR (400 MHz, Chloroform-d) δ 7.94-7.87 (m, 1H), 7.30-7.19 (m, 2H), 4.93 (t, J=6.1 Hz, 2H), 4.31 (qd, J=7.2, 2.0 Hz, 2H), 4.07 (d, J=1.9 Hz, 3H), 2.59 (dt, J=16.1, 5.2 Hz, 4H), 1.43 (td, J=7.2, 1.9 Hz, 3H).

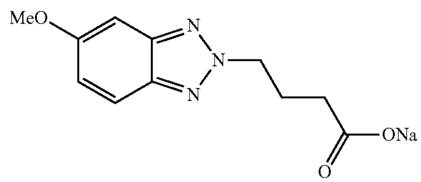

Intermediate 2.09b was prepared analogously to the general procedure, step 2 (Example 1). Yield=70%; m=1.49 g; $^1$H NMR (400 MHz, Methanol-$d_4$) δ 7.72 (dd, J=9.1, 2.5 Hz, 1H), 7.14 (s, 1H), 7.08 (d, J=9.3 Hz, 1H), 4.75 (q, J=3.8 Hz, 2H), 3.89 (d, J=2.6 Hz, 3H), 2.35 (d, J=2.9 Hz, 4H).

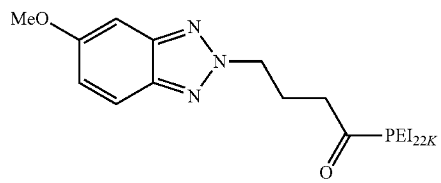

Product 2.09 was prepared analogously to the general procedure, step 3 (Example 1). Yield-90%; m=146 mg; $^1$H NMR (400 MHz, Deuterium Oxide) δ 7.87-6.34 (m, 3H), 4.57-4.12 (m, 2H), 4.03-2.76 (m, 20H), 2.58-1.29 (m, 4H).

Synthesis of Product 2.10

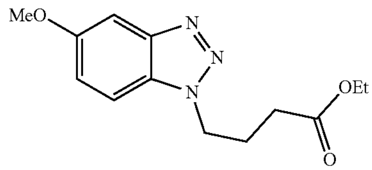 [SMILES: CCOC(=O)CCCn1nnc2cc(OC)ccc21]

Intermediate 2.10a was prepared analogously to the general procedure, step 1 (Example 1). Yield=23%; m=1.69 g; $^1$H NMR (400 MHz, Chloroform-d) δ 7.78 (dd, J=9.1, 1.9 Hz, 1H), 7.34 (dd, J=9.1, 1.9 Hz, OH), 7.26 (d, J=2.3 Hz, OH), 7.05 (dd, J=9.0, 2.2 Hz, OH), 6.89 (dd, J=9.1, 2.2 Hz, 1H), 6.73 (d, J=2.2 Hz, 1H), 4.55 (dtd, J=13.6, 6.7, 1.9 Hz, 2H), 4.01 (q, J=7.1 Hz, 2H), 3.78 (dd, J=6.6, 1.8 Hz, 3H), 3.04 (s, 0H), 2.22 (ddd, J=19.8, 7.7, 4.2 Hz, 4H), 1.13 (td, J=7.1, 1.8 Hz, 3H).

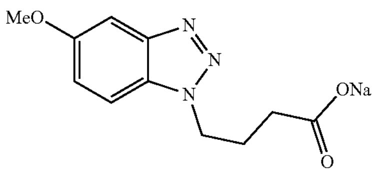

Intermediate 2.10b was prepared analogously to the general procedure, step 2 (Example 1). Yield=70%; m=1.16 g; $^1$H NMR (400 MHz, Methanol-d$_4$) δ 7.81 (dd, J=9.1, 2.7 Hz, 1H), 7.67 (dd, J=8.9, 2.7 Hz, OH), 7.33 (s, OH), 7.24-7.15 (m, 1H), 7.05 (dd, J=9.1, 2.7 Hz, 1H), 4.73 (qd, J=7.1, 2.3 Hz, 2H), 3.91 (dd, J=13.2, 2.8 Hz, 3H), 3.33 (d, J=3.2 Hz, OH), 2.35 (t, J=6.7 Hz, 2H), 2.26 (t, J=7.3 Hz, 2H).

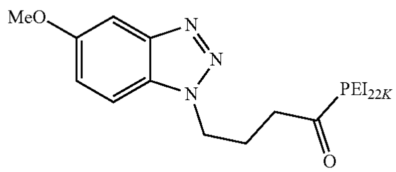

Product 2.10 was prepared analogously to the general procedure, step 3 (Example 1). Yield=96%; m=153 mg; $^1$H NMR (400 MHz, Deuterium Oxide) δ 7.99-6.22 (m, 3H), 4.49-4.03 (m, 2H), 3.96-2.80 (m, 21H), 2.63-1.55 (m, 4H).

Synthesis of Product 2.11

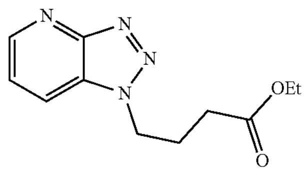 [SMILES: CCOC(=O)CCCn1nnc2ncccc21]

Intermediate 2.11a was prepared analogously to the general procedure, step 1 (Example 1). Yield=77%; m=1.09 g; $^1$H NMR (400 MHz, Chloroform-d) δ 8.83-8.57 (m, 1H), 8.40-8.19 (m, 1H), 7.42-7.30 (m, 1H), 4.89-4.78 (m, 2H), 4.17-4.04 (m, 2H), 2.52-2.28 (m, 5H), 1.22 (tdd, J=7.1, 4.1, 0.9 Hz, 3H).

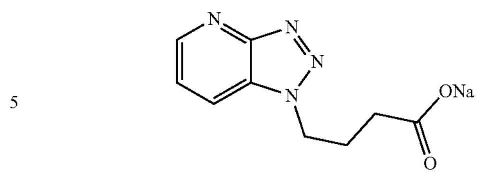

Intermediate 2.11b was prepared analogously to the general procedure, step 2 (Example 1). Yield=100%; m=1.16 g; $^1$H NMR (400 MHz, Deuterium Oxide) δ 8.59-8.49 (m, 2H), 8.31-8.08 (m, 2H), 7.42-7.32 (m, 2H), 4.70-4.63 (m, 2H), 4.63-4.54 (m, 2H), 2.29-2.16 (m, 2H), 2.20-2.05 (m, 7H).

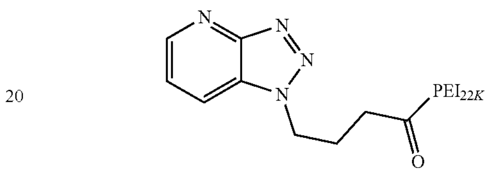

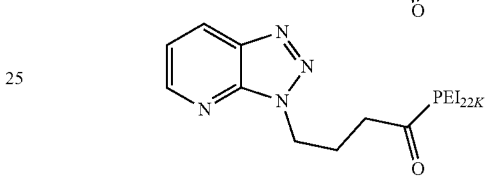

Product 2.11 was prepared analogously to the general procedure, step 3 (Example 1). Yield=56%; m=43 mg; $^1$H NMR (400 MHz, Deuterium Oxide) δ 8.95-6.92 (m, 3H), 4.11-2.95 (m, 18H), 2.90-1.23 (m, 5H).

Synthesis of Product 2.12

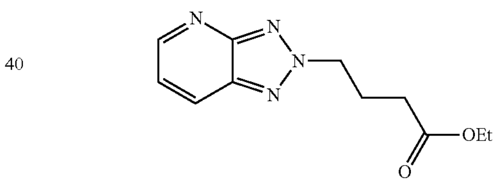

Intermediate 2.12a was prepared analogously to the general procedure, step 1 (Example 1). Yield=18%; m=254 mg; $^1$H NMR (400 MHz, Chloroform-d) δ 8.53 (dd, J=4.4, 1.5 Hz, 1H), 7.82 (dd, J=8.4, 1.5 Hz, 1H), 7.24 (dd, J=8.4, 4.4 Hz, 1H), 4.54 (t, J=6.8 Hz, 2H), 3.89 (q, J=7.1 Hz, 2H), 2.20-2.05 (m, 4H), 1.01 (t, J=7.1 Hz, 3H).

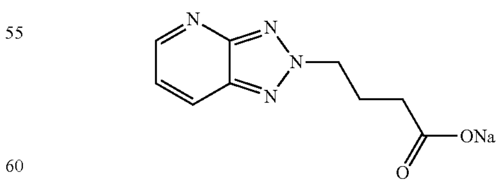

Intermediate 2.12b was prepared analogously to the general procedure, step 2 (Example 1). Yield=98%; m=242 mg; $^1$H NMR (400 MHz, Deuterium Oxide) δ 8.59 (dq, J=4.5, 1.5 Hz, 1H), 8.21 (dt, J=8.5, 1.6 Hz, 1H), 7.52 (ddt, J=8.5, 4.5, 1.4 Hz, 1H), 4.70-4.62 (m, 2H), 2.21-2.04 (m, 4H).

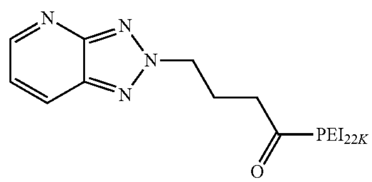

Product 2.12 was prepared analogously to the general procedure, step 3 (Example 1). Yield=75%; m=54 mg; $^1$H NMR (400 MHz, Deuterium Oxide) δ 9.06-6.76 (m, 3H), 4.16-2.96 (m, 20H), 2.93-1.52 (m, 4H).

Synthesis of Product 2.13

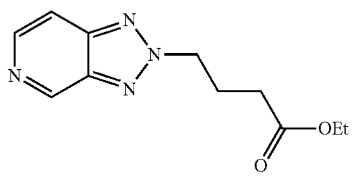 [SMILES: CCOC(=O)CCCn1nc2ccncc2n1]

Intermediate 2.13a was prepared analogously to the general procedure, step 1 (Example 1). Yield=43%; m=736 mg; $^1$H NMR (400 MHz, Chloroform-d) δ 9.41 (d, J=1.4 Hz, 1H), 8.44 (d, J=6.1 Hz, 1H), 7.74 (dd, J=6.1, 1.4 Hz, 1H), 4.87 (t, J=6.5 Hz, 2H), 4.11 (q, J=7.1 Hz, 2H), 2.50-2.39 (m, 2H), 2.41-2.31 (m, 2H), 1.22 (t, J=7.1 Hz, 3H).

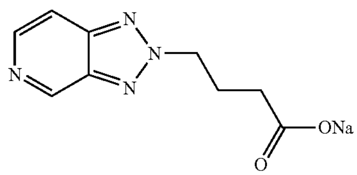

Intermediate 2.13b was prepared analogously to the general procedure, step 2 (Example 1). Yield=100%; m=707 mg; $^1$H NMR (400 MHz, Deuterium Oxide) δ 9.25 (d, J=1.4 Hz, 1H), 8.27 (dd, J=6.3, 1.2 Hz, 1H), 7.77 (dt, J=6.4, 1.6 Hz, 1H), 4.79 (t, J=6.9 Hz, 2H), 2.26 (dqd, J=7.8, 6.9, 0.9 Hz, 2H), 2.11 (ddd, J=8.0, 7.1, 1.0 Hz, 2H).

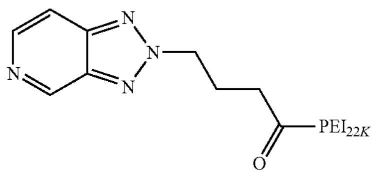

Product 2.13 was prepared analogously to the general procedure, step 3 (Example 1). Yield=95%; m=65 mg; $^1$H NMR (400 MHz, Deuterium Oxide) δ 10.06-7.98 (m, 3H), 4.07-2.89 (m, 27H), 2.83-2.11 (m, 4H).

Synthesis of Product 2.14

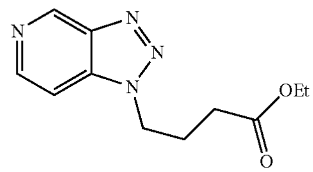 [SMILES: CCOC(=O)CCCn1nnc2cnccc21]

Intermediate 2.14a was prepared analogously to the general procedure, step 1 (Example 1). Yield=52%; m=600 mg; $^1$H NMR (400 MHz, Chloroform-d) δ 9.51-9.16 (m, 1H), 8.60-8.50 (m, 1H), 7.96-7.52 (m, 1H), 4.90-4.71 (m, 2H), 4.10 (dq, J=8.6, 7.1 Hz, 2H), 2.43-2.30 (m, 4H), 1.23 (t, J=7.2 Hz, 3H).

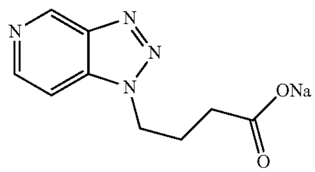

Intermediate 2.14b was prepared analogously to the general procedure, step 2 (Example 1). Yield=97%; m=550 mg; $^1$H NMR (400 MHz, Deuterium Oxide) δ 9.27-9.11 (m, 1H), 8.43-8.27 (m, 1H), 7.95-7.69 (m, 1H), 4.84-4.63 (m, 2H), 2.28-2.05 (m, 4H).

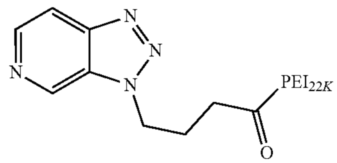

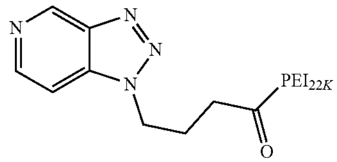

Product 2.14 was prepared analogously to the general procedure, step 3 (Example 1). Yield=95%; m=68 mg; $^1$H NMR (400 MHz, Deuterium Oxide) δ 10.08-8.17 (m, 3H), 4.21-2.84 (m, 25H), 2.83-1.64 (m, 4H).

Synthesis of Product 2.15

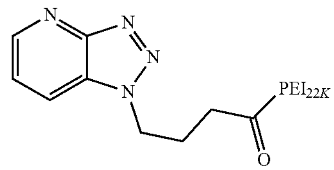

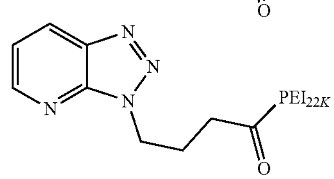

Product 2.15 was prepared analogously to the general procedure, step 3. Yield=88%; m=74 mg; $^1$H NMR (400 MHz, Deuterium Oxide) δ 8.98-7.01 (m, 3H), 4.07-3.06 (m, 14H), 2.75-1.45 (m, 4H).

Synthesis of Product 2.16

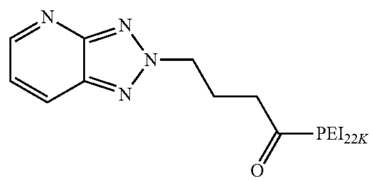

Product 2.16 was prepared analogously to the general procedure, step 3 (Example 1). Yield=46%; m=42 mg; $^1$H NMR (400 MHz, Deuterium Oxide) δ 8.97-6.90 (m, 3H), 4.07-2.81 (m, 12H), 2.60-1.43 (m, 4H).

Synthesis of Product 2.17

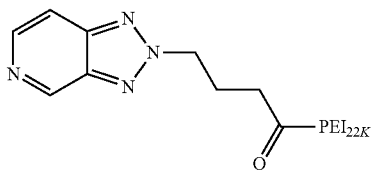

Product 2.17 was prepared analogously to the general procedure, step 3 (Example 1). Yield=97%; m=82 mg; $^1$H NMR (400 MHz, Deuterium Oxide) δ 10.03-8.05 (m, 3H), 4.20-3.04 (m, 14H), 2.81-1.60 (m, 4H).

Synthesis of Product 2.18

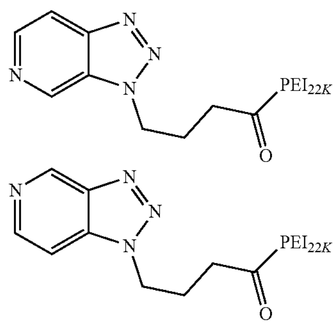

Product 2.18 was prepared analogously to the general procedure, step 3 (Example 1). Yield=97%; m=82 mg; 1H NMR (400 MHz, Deuterium Oxide) δ 10.02-8.30 (m, 3H), 3.54 (s, 15H), 2.93-1.88 (m, 4H).

Example 3. Compounds 1.01 to 1.50

Screening of Transfection Activity

Compounds 1.01 to 1.50 were evaluated for their ability to transfect DNA in four different cell lines. Many cell lines were first transfected with commercially available transfection reagents (see Table 2). The plasmid pCMV-EGFPLuc encoding the Green Fluorescent Protein (GFP) was used and the transfection efficiency in 96-well plate format was determined by analyzing the percentage of cells expressing the GFP (% GFP) by cytometry assay one day post-transfection. Table 2 presents the results of commercial reagents used in their optimal conditions for the four cell lines, Caco-2 (human colon epithelial cells), Hep G2 (human hepatocarcinoma cells), MDCK (Madin-Darby canine kidney epithelial cells) and MCF-10A (human mammary epithelial cells). The results indicated that these cells were relatively difficult to transfect as the highest transfection efficiencies were inferior to 40%, 28%, 40% and 22% in Caco-2, Hep G2, MDCK and MCF-10A, respectively. These cell lines were selected to screen the transfection activity of compounds 1.01 to 1.50.

TABLE 2

Transfection of Caco-2, Hep G2, MDCK and MCF-10A with commercially available reagents (jetPEI ®, jetPRIME ® form Polyplus-transfection, ViaFect ® from Promega, TransIT-XT2 ® from MirusBio, X-tremeGENE 9 ® from Roche Life Science, LipoFectamine ® 3000 from Thermo Fisher).

| Cell line | Commercial reagent | Amount of DNA/well | Ratio µg DNA _µL transfection reagent | % GFP |
|---|---|---|---|---|
| CaCo-2 | Viafect | 150 ng | 1_4 | 5.92 |
| | X-tremeGENE9 | 150 ng | 1_6 | 7.06 |
| | TransFectin | 150 ng | 1_4 | 22.15 |
| | jetPRIME | 150 ng | 1_2 | 31.19 |
| | jetPEI | 200 ng | 1_3 | 15.9 |
| | LipoFectamine 3000 | 150 ng | 1_3 | 39.92 |
| HepG2 | Viafect | 150 ng | 1_4 | 3.21 |
| | X-tremeGENE9 | 150 ng | 1_6 | 11.34 |
| | TransIT-X2 | 150 ng | 1_4 | 8.06 |
| | TransFectin | 150 ng | 1_4 | 9.77 |
| | jetPRIME | 150 ng | 1_3 | 10.77 |
| | jetPEI | 200 ng | 1_3 | 16.16 |
| | LipoFectamine 3000 | 200 ng | 1_3 | 27.77 |
| MDCK | Viafect | 150 ng | 1_4 | 11.64 |
| | TransIT-X2 | 150 ng | 1_4 | 14.63 |
| | jetPRIME | 150 ng | 1_3 | 13.5 |
| | jetPEI | 200 ng | 1_2 | 15.27 |
| | LipoFectamine 3000 | 150 ng | 1_3 | 39.5 |
| MCF-10A | Viafect | 150 ng | 1_4 | 6.80 |
| | X-tremeGENE9 | 150 ng | 1_6 | 3.82 |
| | TransIT-X2 | 150 ng | 1_4 | 8.58 |
| | jetPRIME | 150 ng | 1_3 | 21.40 |
| | jetPEI | 200 ng | 1_2 | 8.0 |
| | LipoFectamine 3000 | 150 ng | 1_3 | 17.75 |

The screening of compounds 1.01 to 1.50 (FIG. 1) was performed in 96-well plate by transfecting 200 ng of pCMV-EGFPLuc DNA (Clontech) complexed with 0.6 or 0.8 µL of one compound of the invention, i.e. one compound selected from the group consisting of compounds 1.01 to 1.50 (at 7.5 mM nitrogen concentration), defining a ratio of 1 µg DNA/3 µL of compound (ratio 1:3) or a ratio of 1 µg DNA/4 µL of compound (ratio 1:4), respectively. The percentage of cells expressing the GFP (% GFP) was determined by cytometry assay one day post-transfection. A transfection was performed with jetPEI® as a control which is a linear polyethylenimine of 22KDa and represents the parental cationic polymer backbone of compounds 1.01 to 1.50.

The activity results of the compounds comprising a benzimidazole ring, wherein $Y^1$=$Y^3$=N, $Y^2$=C, and R, T, U, V form a benzene ring, showed an efficient transfection with the products 1.07 to 1.08, 1.14 to 1.22, 1.25, 1.27 to 1.30, 1.32, 1.35 to 1.37, 1.41, 1.42 with a similar profile of efficiency in the four cell lines tested. Among these compounds comprising a benzimidazole ring, when $Z^2$ is different of H, many compounds showed an improved efficiency when compared to jetPEI®, such as 1.09, 1.10, 1.15, 1.27, 1.28,1.30, 1.32, 1.35, 1.36, 1.37, 1.41, 1.42 wherein $Z^2$=$CH_3$, or 1.14 wherein $Z^2$=$CF_3$, or 1.17 wherein $Z^2$=S—$CH_3$, 1.18 wherein $Z^2$-isopropyl, or 1.19 wherein $Z^2$-propyl, 1.20 wherein $Z^2$=$CH_2$—NH—$CH_3$, 1.21, 1.22 wherein $Z^2$=$CH_2$—O—$CH_3$. Other substitutions on the benzene ring on position $Z^4$, $Z^5$, or $Z^6$ provided very efficient compounds such as 1.30 wherein $Z^5$=O—$CH_3$, 1.32 wherein $Z^6$=isopropyl, 1.35, 1.36 wherein $Z^6$=$CH_3$, 1.37 wherein $Z^4$=$CH_3$, 1.41, 1.42 wherein $Z^5$=$Z^6$=$CH_3$. Taken together, the data indicated that a chemical diversity could be introduced on compounds comprising a benzimidazole ring, which might favour the transfection efficiency.

The activity results of compounds comprising a benzopyrazole ring (1.44, 1.45, 1.48, 1.49, 1.50), wherein $Y^1$=$Y^2$=N, $Y^3$=C, and R, T, U, V form a benzene ring, showed a moderate transfection efficiency when compared to jetPEI®. Therefore, the compound 1.49 showed high level of transfection, particularly in MDCK cells. Introduction of amino groups in $Z^6$ (1.43, 1.46) or $Z^4$ (1.47) was also tolerated in transfection.

Example 4. Compounds 2.01 to 2.18

Screening of Transfection Activity

Compounds 2.01 to 2.18 were screened in transfection (FIG. 2) similarly as previously described for compounds of Example 3, in 96-well plate by transfecting 200 ng of pCMV-EGFPLuc DNA (Clontech) complexed with 0.6 or 0.8 μL of one compound of the invention (one compound of 2.01 to 2.18) (at 7.5 mM nitrogen concentration), defining a ratio of 1 μg DNA/3 μL of compound or ratio of 1 μg DNA/4 μL of compound, respectively.

Benzotriazole ring derivatives (2.01 to 2.10) were found to be the most interesting compounds of Example 4 according to their transfection activity in transfection of Caco-2, Hep G2, MCF-10A, and MDCK. The grafting position to the polymer $Y^1$ or $Y^2$ ($Z^1$ or $Z^2$) seemed to have low impact on the transfection but the grafting extent on the polymer of benzotriazole ring influenced more the results. The addition of methyl or methoxy groups on position $Z^5$ and/or $Z^6$ might improve the transfection activity as exemplified by compounds 2.05, 2.08, 2.09 or 2.10.

Example 5. Heterocycle Grafting Extent and Cationic Polymer Length

The grafting extent with heterocycle ring to the cationic polymer is a key factor to modulate the transfection activity. FIG. 3 exemplified the grafting impact with 2-methyl benzimidazole to the linear PEI of 22 kDa where a grafting extent from 14% to 25% provided very efficient compounds in transfection, with an optimal closed to 20%, when compared to jetPEI®. This is also exemplified with the compounds 1.28, 1.25, and 1.27 grafted to the linear PEI 10 kDa showing also that a grafting extent around 20% was of interest in transfection (FIG. 1).

Additionally, the cationic polymer length might influence the transfection activity as exemplified by the compounds 1.24, 1.25, and 1.26 where the same grafting extent with 2-methyl benzimidazole ring was performed on polymer having a mean molecular of 22, 10 and 6 kDa, respectively (FIG. 1).

Example 6. Transfection of primary cells

Figure 4:
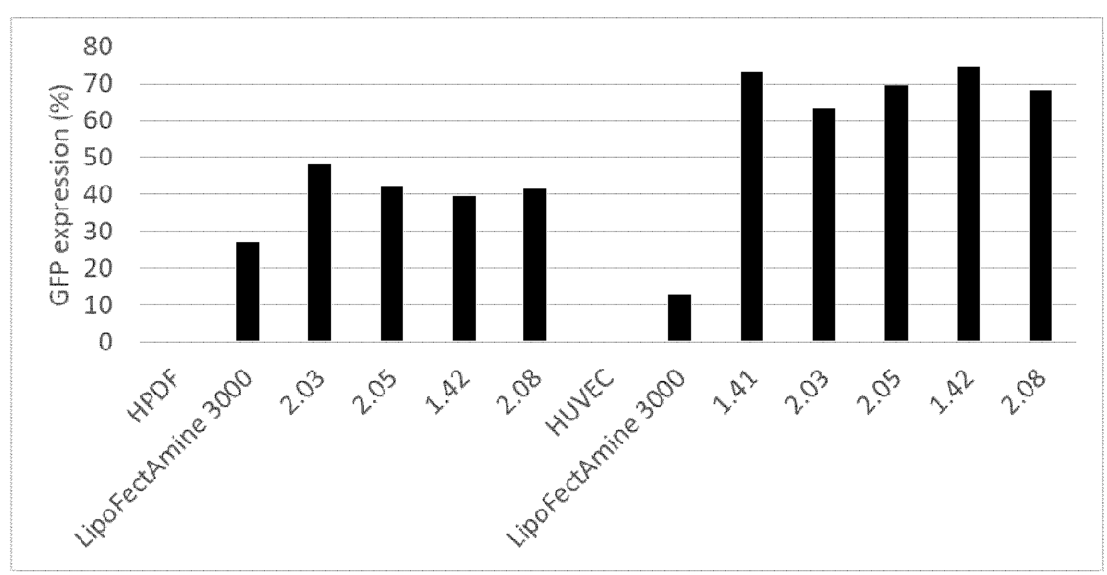
FIG. 4. Percentage of GFP expression after transfection of primary dermal fibroblasts (HPDF) and primary endothelial cells (HUVEC) with compounds 1.41, 2.03, 2.05, 1.42, 2.08 and LipoFectamine® 3000 as a commercial reference.

A selection among the best compounds of Examples 3 and 4 was tried to transfect primary cells, known to be difficult to transfect (FIG. 4), such as primary dermal fibroblasts (HPDF) and primary endothelial cells (HUVEC). Primary cells were cultured with their specific media conditions in 24-well format plate (see Material and Methods). The cells were transfected with 500 ng of pCMV-EGFPLuc complexed with 1.5 μL of compound 1.41, 2.03, 2.05, 1.42 or 2.08 in 50 μL of BUFFER (ratio 1 μg DNA: 3 μL of compounds) or with LipoFectAmine® 3000 (ratio 1 μg DNA: 1.5 μL reagent) according to the recommended protocol. After 2 or 4 h, the transfection medium was removed and replaced by complete medium. The GFP expression analysis was performed 24 h after transfection by cytometry analysis.

The GFP expression results showed that all the compounds selected were able to transfect HPDF and HUVEC cells more efficiently than the commercial reference LipoFectamine® 3000, reaching about 50% of transfection efficiency of HPDF with compound 2.03 and more than 70% transfection efficiency with compounds 1.41 and 1.42. These results indicated the great potential of the compounds of the invention with a possible diversity of the heterocycle grafted to the cationic polymer.

Transfection of primary neurons is known to be very difficult as these non-dividing cells have a very limited access for the transfected DNA to the nucleus. In addition, these cells are very fragile. The inventors have tested compounds closed to the structure 1.42 such as compounds 1.56 to 1.72, and found that compound 1.65 or 1.60 shoved very impressive transfection results of primary neurons. FIG. 5 exemplified the results obtained with compound 1.65 when compared to commercially available transfection reagents.

Primary rat cortex neurons (RCN) and primary rat hippocampal neurons (RHN) were cultivated for 4 days in complete medium, and were then transfected with 150 ng of pCMV-EGFPLuc plasmid complexed with either 0.15 μL of compound 1.65 in 25 μL of OPTIMEM or 0.6 μl of LipoFectAmine® 2000 (ratio 1 μg: 4 μL) and jetPEI® (ratio 1 μg: 2 μL) according to the recommended commercial protocols. The cells were observed 24 h post-transfection by using a fluorescent cell imager.

jetPEI® was found not to be effective to transfect both RCN and RHN where LipoFectAmine® 2000 provided significant level of transfection efficiency. Therefore, compound 1.65 was shown to nicely transfect both RCN and RHN with a higher efficiency without affecting the cell morphology (the cell dendrites were clearly observables). In contrast, the morphology of cells transfected with LipoFectAmine® 2000 was clearly affected with few remaining dendrites indicating toxicity effect.

Example 7. Bioproduction of Recombinant Virus

DNA transfection is one of the frequently used technologies in the bioproduction of recombinant proteins and viruses by a process of transient gene expression (TGE). Concerning the production of AAV and lentivirus the most commonly used method is the transfection to deliver the viral and therapeutic genes in the producer cell lines, HEK293 adherent of suspension cells. In most systems, the co-transfection of many plasmids is performed by a chemical method, such as the co-precipitation with the calcium phosphate or the transfection mediated with the cationic polymer polyethylenimine (PEI), such as PEIpro® (Polyplus-transfection).

AAV and lentivirus particles were produced from HEK-293T cells through transient co-transfection of several plasmids containing the gene of interest and necessary viral components to produce full recombinant virions. AAV-2 and lentivirus vectors expressing the GFP reporter gene were produced with various compounds and the virus productivity was determined by assessing the transducing unit (TU/mL) 3 days post-transfection. The levels of productivity were compared to those obtained with the PEIpro® transfection reagent extensively used in adherent and suspension virus production systems.

Many compounds of Examples 3 and 4 were tested for the production of AAV-2 and FIG. 6 presents some of the results obtained. At a ratio of 1:2 (1 μg total DNA per μL of compound) used for the transfection, some compounds performed similarly in virus productivity than PEIpro® but most of them increased significantly by 3- to 8-fold the viral titer.

Similarly, lentiviruses were produced in suspension HEK-293T cells after co-transfection of 4 plasmids (pRSV-REV packaging vector, pCgpV Packaging Vector, pCMV-VSV-G Envelop Vector and pLenti6.3/V5-GW/EmGFP Expression Control Vector). Lentivirus titers (TU/mL) were determined 72 hours post-transfection (FIG. 7).

Example 8. CRISPR Cas9 DNA Transfection

The CRISPR-Cas9 technology was used to introduce a deletion in the targeted human HPRT-1 gene. A plasmid encoding both the spCas9 protein and the guide RNA was introduced by the transfection into HEK293 cells with compound 1.42.

Two days post-transfection, the genomic DNA was extracted and submitted to PCR using HPRT-1 specific primers. The genome editing event was analysed by the T7 Endonuclease assay and visualized on agarose gel and quantified using Ethidium Bromide staining to determine the % INDEL (percentage of insertion/deletion CRISPR event). The transfected plasmid p38285 expressing the spCas9 and the specific HPRT-1 guide RNA showed the presence of the two expected bands on the gel at 650 bp and 430 bp (FIG. 8). The % INDEL (Insertion-deletion mutation event) was 33.48+/−7.08%. The specificity of the CRISPR Cas9 transfection was shown as specific signals of cleaved band was observed after transfection of the plasmid targeting the HPRT-1 gene and not with the plasmid control. The experiment demonstrated that compound 1.42 used for the transfection was efficient to induce a CRISRP Cas9 genome modification without generating off-targets events.

Example 9. Transfection Assay of Stem Cells

Primary hyman mesenchymal stem cells (hMSC) were transfected with the compound 1.42 and different amount of pCMV-EGFP DNA, 400 and 500 ng per well in 24-well plate format (FIG. 9). Various volumes of compound 1.42 were used per amount of DNA. One day post-transfection, the GFP expression was analysed by flow cytometry or the cells were observed using a ZOE™ Fluorescent Cell Imager. For the conditions with 400 ng of DNA, a progressive increase of the transfection efficiency was quantified when the volume of compound 1.42 was increased to reach an optimal transfection up to 60% of GFP positive cells. For the conditions at 500 ng DNA, the best condition was obtained with 0.75 μL of compound 1.42 with more than 60% of GFP positive cells. As a control, the transfection performed with the Lipofectamine 3000 reagent provided a transfection efficiency inferior to 10%. These results show that an optimization of the transfection conditions can be realized by varying both the DNA amount transfected and the volume of compound.

Example 10. Compounds 1.73 to 1.80

The inventors carried out some comparative data using imidazole derivatives such as compounds 1.73, 1.78 and 1.80 (see Table 3). Synthesis of said compounds is reported in Example 2.

TABLE 3

| Imidazole derivatives | | | |
|---|---|---|---|
| Compound | Structure | Polymer Molecular weight | Heterocycle grafting |
| 1.73 | 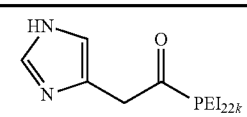 | 22k | 29% |
| 1.78 | 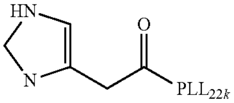 | 22k | 30% |
| 1.80 | 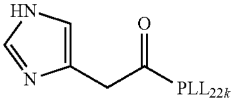 | 22k | 45% |

Screening of Transfection Activity

Figure 11:
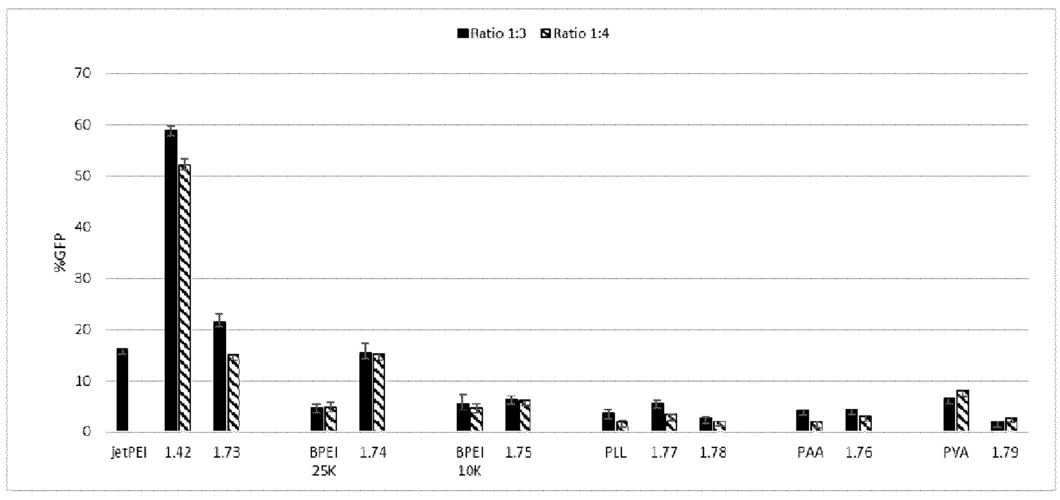
FIG. 11. Percentage of GFP expression after transfection of Hep G2 cells with compounds of Example 10. The ratio 1:3 and 1:4 indicate the ratio of μg of DNA per μL of compound.

Compounds 1.73 to 1.80 were evaluated for their ability to transfect DNA (pCMV-EGFPLuc) in Hep G2 cells and the transfection efficiency in 96-well plate format was determined by analyzing the percentage of cells expressing the GFP (% GFP) by cytometry assay one day post-transfection (FIG. 11). Compounds 1.73 to 1.80 were compared to the compound 1.42 comprising a benzimidazole ring grafted to the linear PEI 22K wherein $Z^2$, $Z^4$ and $Z^6$=$CH_3$. This benzene ring derivative was grafted onto many cationic polymers, including branched PEI (25K or 10K), Poly (allylamine) (PAA, 15K), Polylysine (PLL, 22K) or Poly (vinylamine (PVA,25K). The presence of the benzimidazole ring showed higher transfection efficiencies when compared to the unmodified parental polymers. This effect was particularly shown with the compounds 1.42 and 1.74 wherein the parental polymer is PEI. In addition, the compound 1.42 with a benzimidazole ring showed a higher transfection efficiency when compared to the compound 1.73 comprising an imidazole ring grafted to the linear PEI 22K.

Bioproduction of Recombinant Virus

Figure 12:
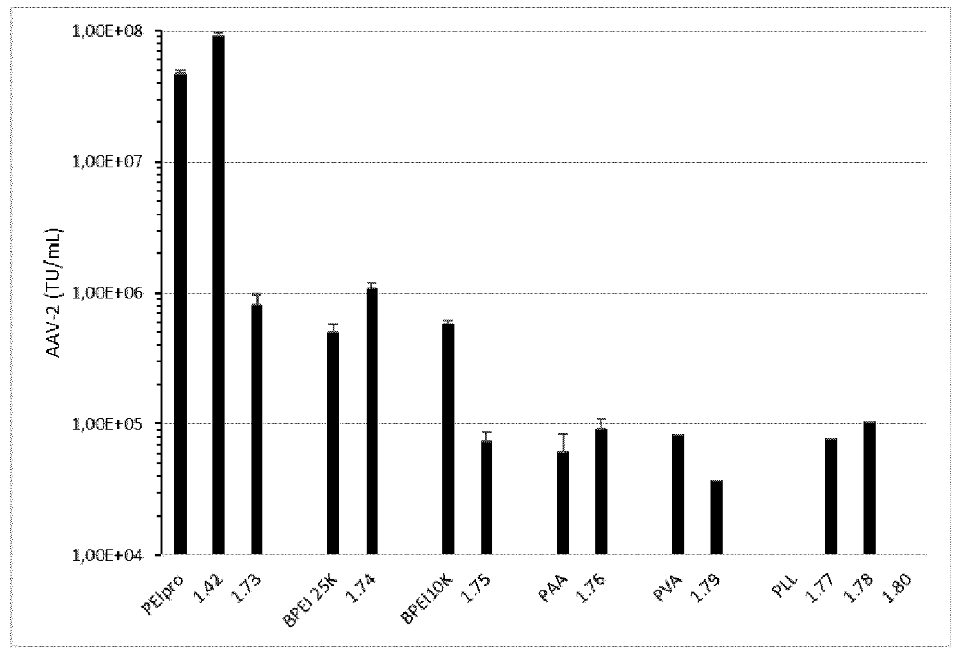
FIG. 12. Production of AAV-2 from suspension HEK-293T cells. AAV-2 vectors expressing the GFP reporter gene were produced in HEK-293T cells grown in suspension in FreeStyle F17 media. Cells were seeded and cultured for 3 days before being transfected by 3 plasmids (pAAV-RC2 vector expressing Rep and Cap from Cell BIOLABS, INC., pALD-X80, Helper vector expressing Adeno E2A, Adeno E4 and Adeno VA helper factors from ALDEVRON, and pAAV-GFP control vector expressing the GFP under the control of a CMV promoter from Cell BIOLABS, INC.) with PElpro® or various compounds. AAV titers (transducing unit, TU/mL) were determined 72 hours post-transfection. The results are expressed as relative AAV-2 transducing Units/mL (TU/mL) in comparison to PElpro® transfection at their best ratio of μg of DNA per μL of compound (ratio 1:2 for PElpro®, 1.42, 1.73, 1.74, 1.76, 1.80, 1.75 and ratio 1:5 for BPEI 25K, BPEI 10K, PAA, PVA, PLL, 1.78 and 1.77.

Compounds 1.73 to 1.80 were tested for the production of AAV-2 and FIG. 12 presents the results obtained at the best ratio μg DNA/μL compound. The presence of the benzimidazole ring showed higher AAV-2 productivites when compared to the unmodified parental polymers, particularly shown with the compounds 1.42 and 1.74 wherein the parental polymer is PEI (linear 22K or branched 25K, respectively). Compound 1.42 showed a significant higher virus production when compared to the compound 1.73 comprising an imidazole ring grafted to the linear PEI 22K.

CONCLUSION

Many compounds based on grafting of polyamine with heterocycles of formula (II) showed improved performances to induce gene expression in "hard to transfect" cells such as cancer cells, primary cells, non-dividing cells or to increase the productivity of biologics such as viruses, AAV or LV.

Many compounds of Examples 3 and 10 comprising a benzimidazole ring wherein $Y^1$=$Y^3$=N, $Y^2$=C, and R, T, U, V form a benzene ring showed higher transfection efficiency when compared to the unmodified parental linear PEI (jetPEI®) or compared to linear modified PEI comprising an imidazole ring or compared to cationic polymers exhibiting benzimidazole or imidazole grafts in the four cancer cell lines tested. Among the various structures tested, when $Z^2$ is different of H, and particularly with $Z^2$=$CH_3$, and $Z^4$, $Z^5$ or $Z^6$ are different of H, particularly with $Z^4$, $Z^5$ or $Z^6$=$CH_3$, the compounds provided the highest transfection efficiencies.

Many compounds of Example 3 comprising a benzopyrazole ring wherein $Y^1$=$Y^2$=N, $Y^3$=C, and R, T, U, V form a benzene ring showed promising activity in transfection.

These results were also confirmed after transfection of primary cells, particularly non-dividing cells, such as primary neurons, but also fragile cells and "hard to transfect cells" such as primary fibroblasts, endothelial cells or stem cells.

Many compounds of Example 4, particularly polyamine grafted with benzotriazole derivatives showed high transfection efficiencies, similarly to the best compounds of Example 3.

Selected compounds of Examples 3 and 4 also showed improved productivity of biologics such as AAV or LV, indicating a combined effect of high transfection efficiency and gene expression in cells resulting in high virus titers expressed as transducing units. Improved virus productivity was observed whatever the type of transfected cells, e.g. adherent or in suspension. The results obtained indicated that such compounds might be also of interest to produce other biologics such as recombinant proteins, peptides or antibodies.

Taken together, the compounds of formula (II) of the invention represent novel reagents for transfection and bioproduction purposes wherein a fine optimisation of the chemical structure may be adapted for each application, cell types or transfection conditions.

The person skilled in the art can adapt the transfection method with the compounds of formula (II) of the invention to a particular cell type, cell culture conditions or cell culture devices used. In particular, the amount of DNA, amount of transfection reagent, volume of transfection complexes, conditions of mixing of DNA and transfection reagent, medium of transfection complex preparation can vary. In addition, the transfection method with the compounds of formula (II) of the invention can be adapted for industrial uses, particularly at large scale applications in bioreactors for both adherent and suspension cells.

The person skilled in the art can adapt the transfection method with the compounds of formula (II) of the invention for in vivo applications with an acceptable excipient or buffering agent. The compounds of formula (II) can be mixed with DNA to generate DNA complexes suitable for direct injection into animals or humans. Particularly low salt buffering agents such as TRIS, phosphate, or citrate buffer or excipient such as glucose, dextrose, or maltose are known to provide acceptable formulation for direct injection into animals and humans. Many mixture methods between the DNA and the compounds of formula (II) are suitable as they are able to generate formulation containing small size particles (non-agregated DNA complexes) that can be injected through various routes of administration.

REFERENCES

Kaestner L, Schol A, Lipp P. Conceptual and technical aspects of transfection and gene delivery. Bioorganic & Medicinal Chemistry Letters, 25 (6), 1171-1176 (2015).

Merten O W, Hebben M, Bovolenta C. Production of lentiviral vectors. Mol Ther Methods Clin Dev. 3:16017 (2016).

Van der Loo J C, Wright J F. Progress and challenges in viral vector manufacturing. Hum Mol Genet. 25 (R1): R42-52 (2015).

Labat-Moleur F, Steffan A M, Brisson C, Perron H, Feugeas O, Furstenberger P, Oberling F, Brambilla E, Behr J P. An electron microscopy study into the mechanism of gene transfer with lipopolyamines. Gene Ther., 3 (11): 1010-7 (1996).

Mislick K A, Baldeschwieler J D. Evidence for the role of proteoglycans in cation-mediated gene transfer. Proc Natl Acad Sci USA, 93 (22): 12349-54 (1996).

Felgner P L, Gadek T R, Holm M, Roman R, Chan H W, Wenz M, Northrop J P, Ringold G M, Danielsen M. Lipofection: a highly efficient, lipid-mediated DNA-transfection procedure. Proc Natl Acad Sci USA, 84 (21): 7413-7 (1987).

Behr J P, Demeneix B, Loeffler J P, Perez-Mutul J. Efficient gene transfer into mammalian primary endocrine cells with lipopolyamine-coated DNA. Proc Natl Acad Sci USA, 86:6982-6986 (1989).

Gao X, Huang L. A novel cationic liposome reagent for efficient transfection of mammalian cells. Biochem Biophys Res Commun., 179 (1): 280-5 (1991).

Wu G Y, Wu C H. Receptor-mediated in vitro gene transformation by a soluble DNA carrier system. The Journal of Biological Chemistry, 262, 4429-4432 (1987).

Zenke M, Steinlein P, Wagner E, Cotton M, Beug H, Birnstiel M L. Receptor-mediated endocytosis of transferrin-polycation conjugates: an efficient way to introduce DNA into hematopoietic cells. Proc Natl Acad Sci USA, 87 (10) 3655-3659 (1990).

Erbacher P, Roche A C, Monsigny M, Midoux P. Putative role of chloroquine in gene transfer into a human hepatoma cell line by DNA/lactosylated polylysine complexes. Exp Cell Res., 225 (1): 186-94 (1996).

Plank C, Oberhauser B, Mechtler K, Koch C, Wagner E. The influence of endosome-disruptive peptides on gene transfer using synthetic virus-like gene transfer systems. J Biol Chem., 269 (17): 12918-24 (1994).

Boussif O, Lezoualc'h F, Zanta M A, Mergny M D, Scherman D, Demeneix B, Behr J P. A versatile vector for gene and oligonucleotide transfer into cells in culture and in vivo: polyethylenimine. Proc Natl Acad Sci USA., 92 (16): 7297-7301 (1995).

Sonawane N D, Szoka F C Jr, Verkman A S. Chloride accumulation and swelling in endosomes enhances DNA transfer by polyamine-DNA polyplexes. J Biol Chem., 278 (45): 44826-31 (2003).

Itaka K, Harada A, Yamasaki Y, et al. In situ single cell observation by fluorescence resonance energy transfer reveals fast intracytoplasmic delivery and easy release of plasmid DNA complexed with linear polyethylenimine. J Gene Med, 6:76-84 (2004).

Chandrashekhar C, Pons B, Muller C D, Tounsi N, Mulherkar R, Zuber G. Oligobenzylethylenimine enriches linear polyethylenimine with a pH-sensitive membranedisruptive property and leads to enhanced gene delivery activity. Acta Biomaterialia, 9 (2): 4985-4993 (2012).
Erbacher P, Zou S, Bettinger T, Steffan A M, Remy J S. Chitosan-based vector/DNA complexes for gene delivery: biophysical characteristics and transfection ability. Pharm Res., 15 (9): 1332-9 (1998).
Tomalia D A, Baker D, Dewald J, Hall M, Kallos G, Martin S, Roeck J, Ryder, Smith J. A New Class of Polymers: Starburst-Dendritic Macromolecules Polymer Journal 17, 117-132 (1985).
Haensler J, Szoka F C. Polyamidoamine cascade polymers mediate efficient transfection of cells in culture. Bioconjugate Chem., 45, 372-379 (1993).
Tang M X, Redemann C T, Szoka F C Jr. In vitro gene delivery by degraded polyamidoamine dendrimers. Bioconjug Chem., 7 (6): 703-14 (1996).
Liu X, Wu J, Yammine M, Zhou J, Posocco P, Viel S, Liu C, Ziarelli F, Fermeglia M, Pricl S, Victorero G, Nguyen C, Erbacher P, Behr J P, Peng L. Structurally flexible triethanolamine core PAMAM dendrimers are effective nanovectors for DNA transfection in vitro and in vivo to the mouse thymus. Bioconjug Chem., 22 (12): 2461-73 (2011).
Little S R, Lynn D, Ge Q, Anderson D G, Puram S V, Chen J, Eisen H, Langer R. From The Cover: Poly-amino ester-containing microparticles enhance the activity of non-viral genetic vaccines. Proc Natl Acad Sci USA, 101 (26), 9534-9539 (2004).
Akinc A, Anderson D G, Lynn D M, Langer R. Synthesis of poly(beta-amino ester) s optimized for highly effective gene delivery. Bioconjug Chem., 14:979-988 (2003).
Cryan S, Donohue R, Ravoo B J, Darcy R, O'Driscoll C M. Cationic cyclodextrin amphiphiles as gene delivery vectors. Journal of Drug Delivery Science and Technology, 14 (1), Pages 57-62 (2004).
Dréan M, Debuigne A, Jérôme C, Goncalves C, Midoux P, Rieger J, Guégan P. Poly(N-methylvinylamine)-Based Copolymers for Improved Gene Transfection. Macromol Biosci., 18 (4): e1700353 (2018).
Boussif O, Delair T, Brua C, Veron L, Pavirani A, Kolbe H V. Synthesis of polyallylamine derivatives and their use as gene transfer vectors in vitro. Bioconjug Chem. 10 (5): 877-83 (1999).
Dong Y, Skoultchi A I, Pollard J W. Efficient DNA transfection of quiescent mammalian cells using poly-L-ornithine. Nucleic Acids Res., 21 (3): 771-772 (1993).
Alhakamy N A, Berkland C J. Polyarginine molecular weight determines transfection efficiency of calcium condensed complexes. Mol Pharm., 10 (5): 1940-8 (2013).
Putnam D, Zelikinb A N, Izumrudovc V A, Langer R. Polyhistidine-PEG: DNA nanocomposites for gene delivery Biomaterials 24:4425-4433 (2003).
Gupta B, Levchenko T S, Torchilin V P. Intracellular delivery of large molecules and small particles by cell-penetrating proteins and peptides. Advanced Drug Delivery Reviews, 57 (4), 637-651 (2005).
Brunner S, Furtbauer E, Sauer T, Kursa M, Wagner E. Overcoming the Nuclear Barrier: Cell Cycle Independent Nonviral Gene Transfer with Linear Polyethylenimine or Electroporation. Mol. Ther., 5 (1), 80-86 (2002).
Lukacs G L, Haggie P, Seksek O, Lechardeur D, Freedman N, Verkman A S. Size-dependent DNA mobility in cytoplasm and nucleus. J Biol Chem. 275 (3): 1625-9 (2000).
Lechardeur D, Sohn K J, Haardt M, Joshi P B, Monck M, Graham R W, Beatty B, Squire J, O'Brodovich H, Lukacs G L. Metabolic instability of plasmid DNA in the cytosol: a potential barrier to gene transfer. Gene Ther. 6 (4): 482-97 (1999).
Bai H, Schiralli Lester G M, Petishnok L C, Dean D A. Cytoplasmic transport and nuclear import of plasmid DNA. Bioscience Reports 37, BSR20160616 (2017).
Gaba M, Mohan C. Development of drugs based on imidazole and benzimidazole bioactive heterocycles: recent advances and future directions. Medicinal Chemistry Research, 25 (2), 173-210 (2016).
Ivanov A A, Susova O Y, Salyanov V I, Kirsanov K I, Zhuze A L. A new series of biologically active DNA minor groove binders based on bisbenzimidazole and benzimidazole-pyrrole motives. Journal of Biomolecular Structure and Dynamics, 31:1, 52-53 (2013).
Gao C, Li B, Zhang B, Sun Q, Li L, Li X, Chen C, Tan C, Liu H, Jiang Y. Synthesis and biological evaluation of benzimidazole acridine derivatives as potential DNA-binding and apoptosis-inducing agents. Bioorganic & Medicinal Chemistry, 23, 1800-1807 (2015).
Bazhulina N P, Nikitin A M, Rodin S A, Surovaya A N, Kravatsky Y V, Pismensky V F, Archipova V S, Martin R, Gursky G V. Binding of Hoechst 33258 and its derivatives to DNA. J Biomol Struct Dyn. 26 (6): 701-18, (2009).
Tari Ö, Gümüş F, Açik L, Aydin B. Synthesis, characterization and DNA binding studies of platinum (II) complexes with benzimidazole derivative ligands. Bioorg Chem. 74:272-283 (2017).
Fellenius E, Berglindh T, Sachs G, Olbe L, Elander B, Sjöstrand SE, Wallmark B. Substituted benzimidazoles inhibit gastric acid secretion by blocking (H++K+) ATPase. Nature. 290 (5802): 159-61 (1981).
Brown T N, Mora-Diez N. Computational determination of aqueous pKa values of protonated benzimidazoles (Part 2). J Phys Chem B. 110 (41): 20546-54 (2006).

The invention claimed is:

1. A composition for transfecting a nucleic acid molecule into a cell, comprising (i) at least one compound of general formula (II), or an acceptable salt thereof, and (ii) an acceptable excipient, buffering agent, cell culture medium, or transfection medium:

(II)

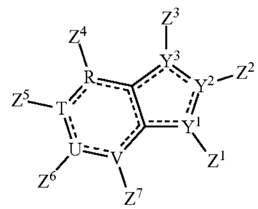

wherein:

(i) $Y^1$ and $Y^3$ represent N, $Y^2$ represents C; $Z^1$ represents $X_1$—$R_3$—$X_2$—$P^+$; $Z^2$ represents H, a linear or branched, saturated or unsaturated $C_1$-$C_{18}$ alkyl, $CF_3$, a linear or branched, saturated or unsaturated $C_2$-$C_{18}$ heteroalkyl, $C_6$-$C_{18}$ aryl, a linear or branched, saturated or unsaturated $C_1$-$C_{18}$ alkylamine, a linear or branched, saturated or unsaturated $C_1$-$C_{18}$ alkyl-$C_1$-$C_{12}$ alkoxy, $C_1$-$C_{18}$ alkyl-halogen; $Z^3$ is absent; $Z^4$ represents H, or a linear or branched, saturated or unsaturated $C_1$-$C_{18}$ alkyl; $Z^5$ represents H, a linear or branched, saturated or unsaturated $C_1$-$C_{18}$ alkyl, a $C_1$-$C_{12}$ alkoxy, halogen, OH, or carboxyphenyl; $Z^6$ represents H, or a linear or branched, saturated or unsaturated $C_1$-$C_{18}$ alkyl; and $Z^7$ represents H; or (ii) $Y^1$, $Y^2$ and $Y^3$ represent N; $Z^1$ represents $X_1$—$R_3$—$X_2$—$P^+$, or $Z^1$ is absent; $Z^2$ represents $X_1$—$R_3$—$X_2$—$P^+$, or $Z^2$ is absent; with the proviso that only one of $Z^1$ or $Z^2$ represents $X_1$—$R_3$—$X_2$—$P^+$; $Z^3$ is absent; $Z^4$ represents H; $Z^5$ represents H, a linear or branched, saturated or unsaturated $C_1$-$C_{18}$ alkyl, or a $C_1$-$C_{12}$ alkoxy; $Z^6$ represents H, a linear or branched, saturated or unsaturated $C_1$-$C_{18}$ alkyl, or a $C_1$-$C_{12}$ alkoxy; $Z^7$ represents H;

$X_1$ represents $CH_2$;

$X_2$ represents CO;

$R_3$ represents $(CH_2)_m$, with m representing an integer between 1 and 3;

$P^+$ represents a graft cationic polymer, which is a linear or branched polyethyleneimine (PEI);

R, T, U and V represent C.

2. The composition according to claim 1, further comprising at least one nucleic acid molecule to be transfected in a cell.

3. The composition according to claim 2, wherein the at least one nucleic acid molecule is a DNA.

4. The composition according to claim 1, wherein the graft cationic polymer is a linear PEI.

5. The composition according to claim 1, wherein the graft cationic polymer has a grafting ratio ranging from 1 to 50%.

6. The composition according to claim 1, wherein the graft cationic polymer has an average molecular weight (Mw) ranging from 1 kDa to 500 kDa.

7. The composition according to claim 1, wherein (i) $Y^1$ and $Y^3$ represent N, $Y^2$ represents C; $Z^1$ represents $X_1$—$R_3$—$X_2$—$P^+$, wherein $X_1$, $X_2$, $R_3$ and $P^+$ are as defined in claim 1; and $Z^2$ represents a linear or branched, saturated or unsaturated $C_1$-$C_6$ alkyl.

8. The composition according to claim 7, wherein $Z^2$ represents $CH_3$.

9. The composition according to claim 1, wherein $Z^4$, $Z^5$, $Z^6$ and $Z^7$ represent H.

10. The composition according to claim 1, wherein (i) $Y^1$ and $Y^3$ represent N, $Y^2$ represents C; and wherein one of $Z^4$, $Z^5$ or $Z^6$ represents a linear or branched, saturated or unsaturated $C_1$-$C_6$ alkyl.

11. The composition according to claim 1, wherein (i) $Y^1$ and $Y^3$ represent N, $Y^2$ represents C; and wherein $Z^4$ and $Z^6$ represent a linear or branched, saturated or unsaturated $C_1$-$C_6$ alkyl.

12. The composition according to claim 1, wherein $Z^5$ and $Z^6$ represent a linear or branched, saturated or unsaturated $C_1$-$C_6$ alkyl.

13. The composition according to claim 1, wherein (i) $Y^1$ and $Y^3$ represent N, $Y^2$ represents C; and wherein $Z^2$, $Z^4$ and $Z^6$ represent a linear or branched, saturated or unsaturated $C_1$-$C_6$ alkyl.

14. The composition according to claim 1, wherein:

$Y^1$ and $Y^3$ represent N, $Y^2$ represents C; and $Z^1$ represents $X_1$—$R_3$—$X_2$—$P^+$, wherein $X_1$, $X_2$, $R_3$ and $P^+$ are as defined in claim 1; and wherein R, T, U and V represent C, and/or $Z^2$ represents H, $CH_3$, $SCH_3$, $CF_3$, phenyl, isopropyl, propyl, $CH_2$—NH—$CH_3$, $CH_2$—O—$CH_3$, or $CH_2$—F, and/or $Z^4$ represents H, $CH_3$, and/or $Z^5$ represents H, F, $OCH_3$, carboxyphenyl, tert-butyl, $C_1$, OH, or $CH_3$, and/or $Z^6$ represents H, or $CH_3$, and/or $Z^7$ represents H.

15. The composition according to claim 1, wherein:

$Y^1$, $Y^2$ and $Y^3$ represent N; and $Z^1$ represents $X_1$—$R_3$—$X_2$—$P^+$, wherein $X_1$, $X_2$, $R_3$ and $P^+$ are as defined in claim 1; and wherein R, T, U and V represent C, and/or $Z^4$ represents H, and/or $Z^5$ represents H, $CH_3$, $OCH_3$, and/or $Z^6$ represents H, $CH_3$, $OCH_3$, and/or $Z^7$ represents H.

16. The composition according to claim 1, wherein the at least one compound of general formula (II) is selected from the group consisting of the following compounds:

1.01

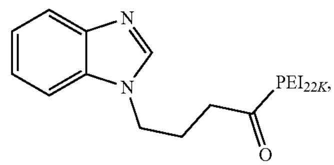

1.07

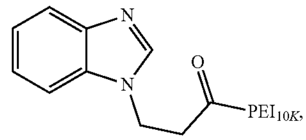

1.08

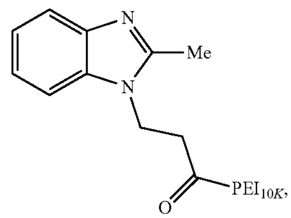

1.09

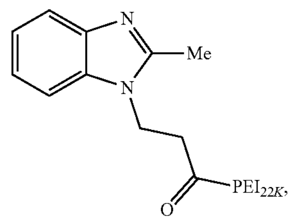

1.10

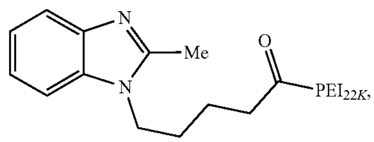

1.12

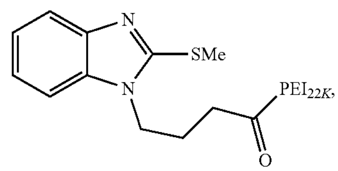

1.13

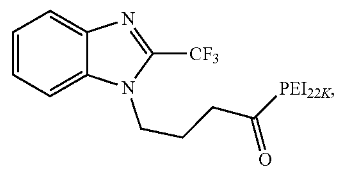

-continued
1.14
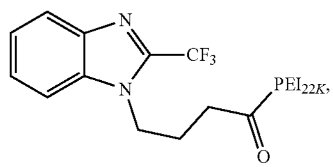
1.15
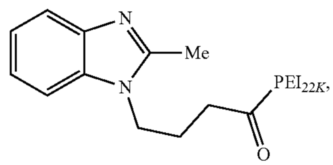
1.16
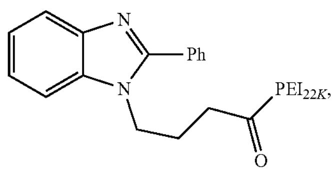
1.17
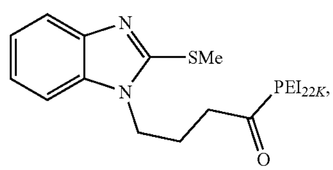
1.18
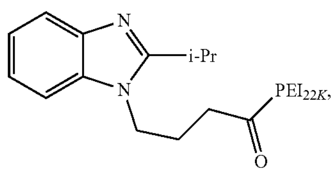
1.19
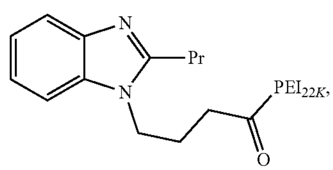
1.20
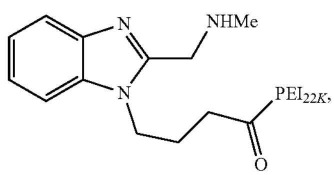
1.21
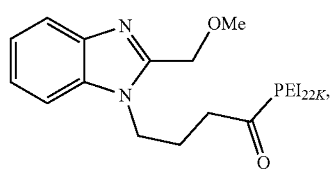
1.22
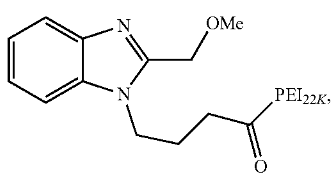
-continued
1.23
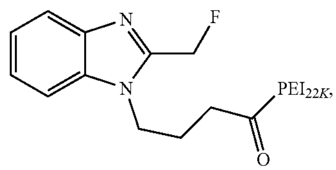
1.24
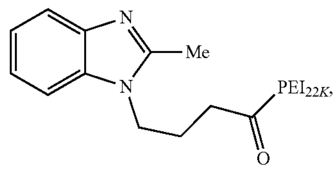
1.25
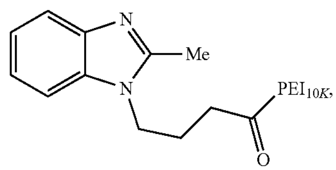
1.26
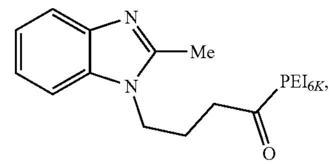
1.27
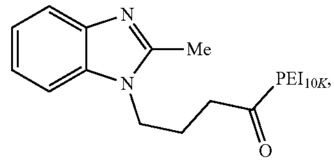
1.28
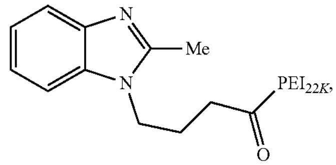
1.29
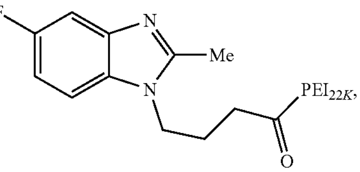
1.30
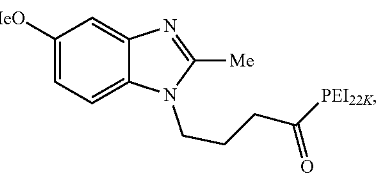
1.31
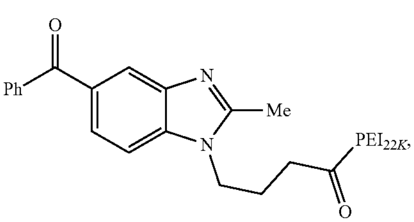

-continued
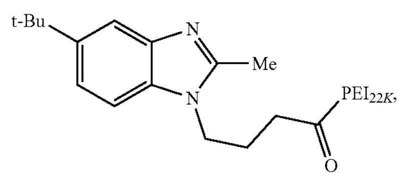
1.32
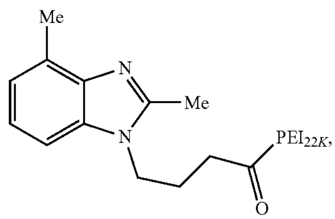
1.33
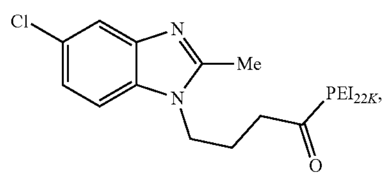
1.34
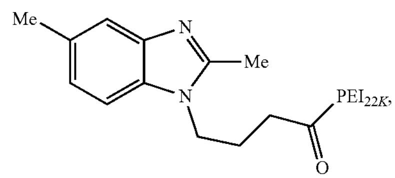
1.35
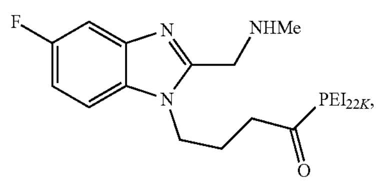
1.36
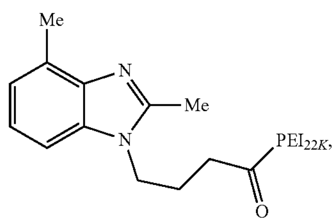
1.37
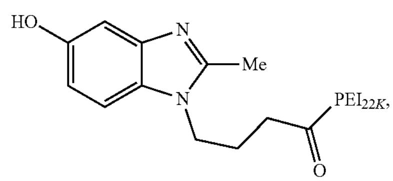
1.38
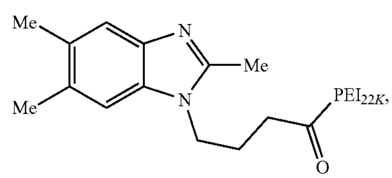
1.41
-continued
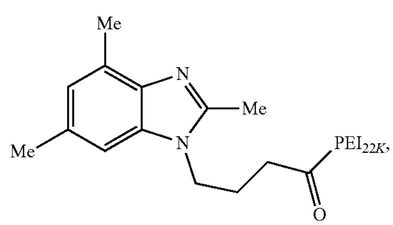
1.42
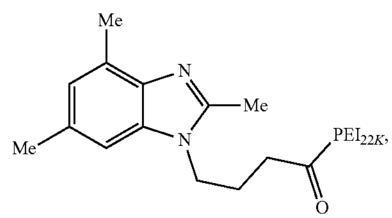
1.56
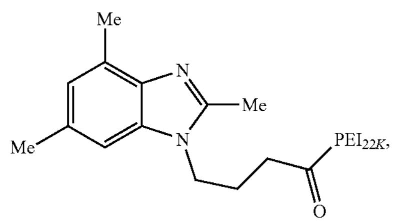
1.57
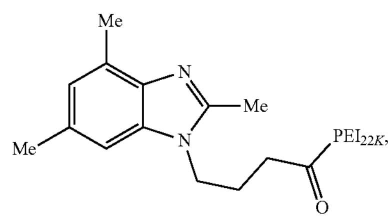
1.58
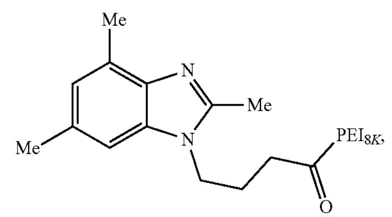
1.59
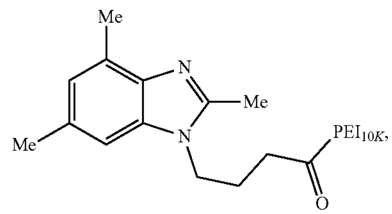
1.60
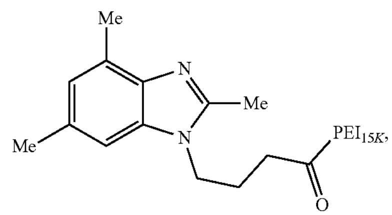
1.61

-continued
1.62
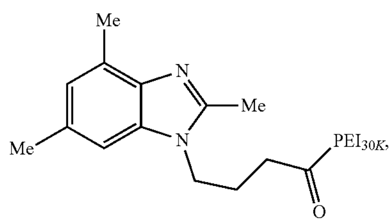
1.63
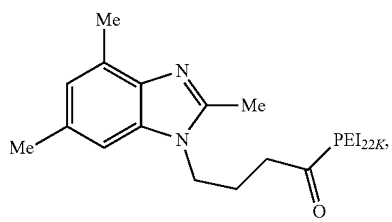
1.64
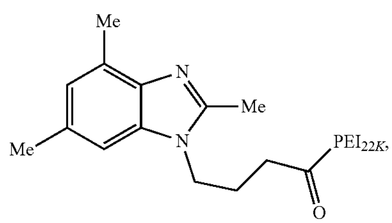
1.65
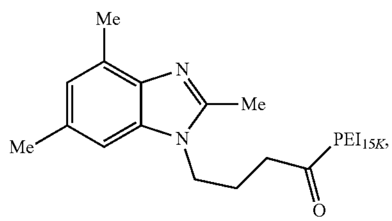
1.66
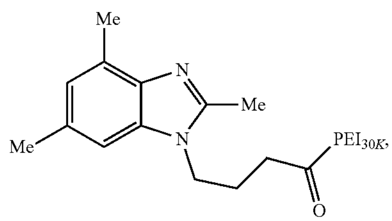
1.67
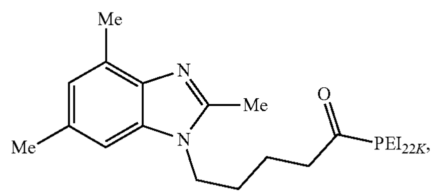
1.68
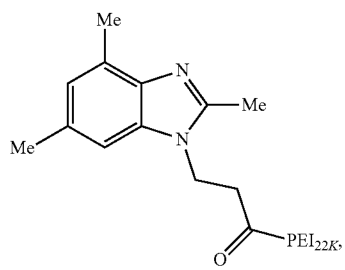
-continued
1.70
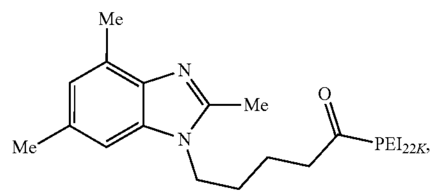
1.71
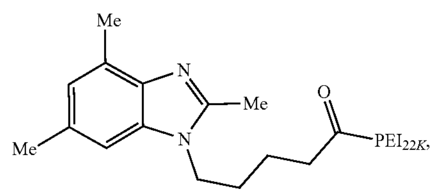
1.72
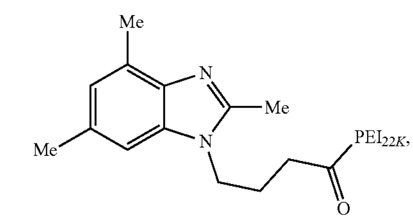
1.74
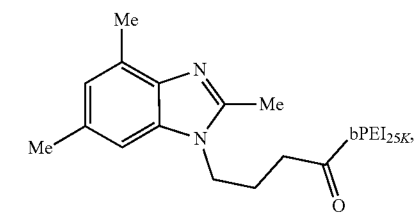
1.75
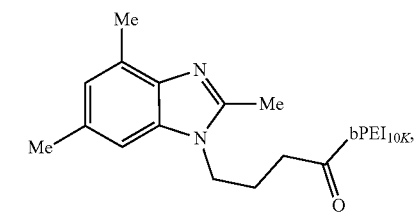
2.01
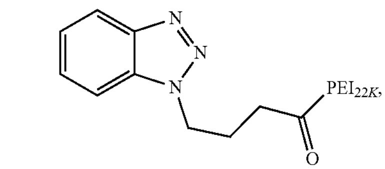
2.02
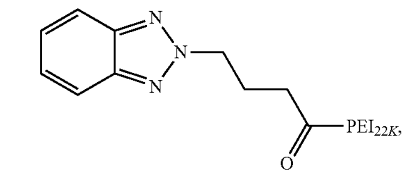
2.03
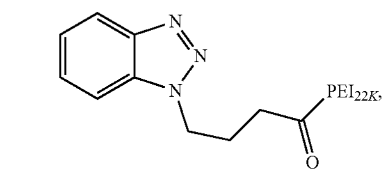

-continued
2.04
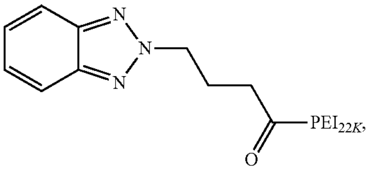
2.05
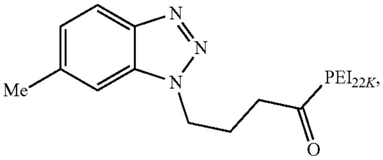
2.06
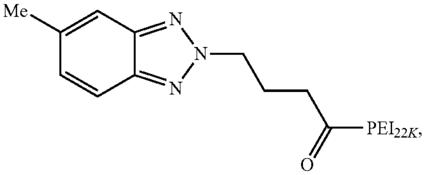
2.07
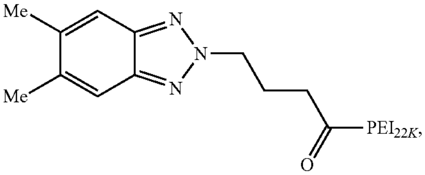
2.08
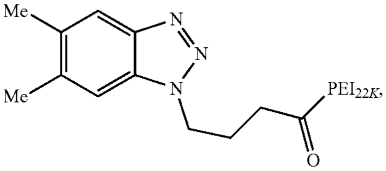
2.09
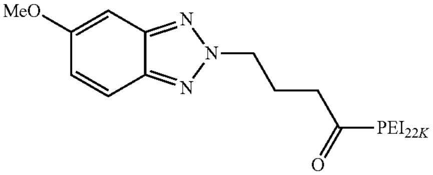
and
2.10
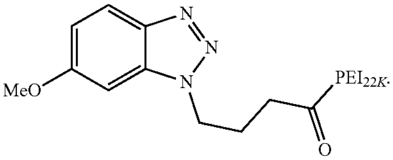
17. The composition according to claim 16, wherein the at least one compound of general formula (II) is selected from the group consisting of the following compounds:
1.09
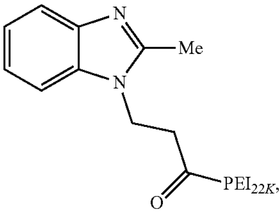
1.10
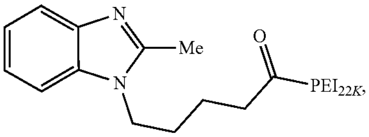
1.14
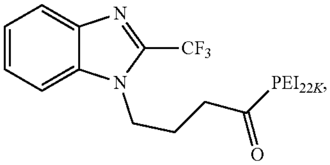
1.15
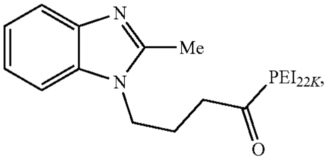
1.17
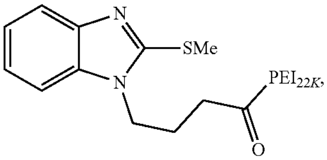
1.18
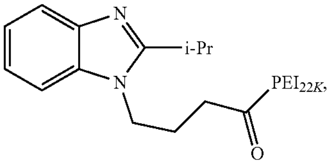
1.19
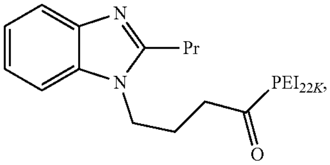
1.20
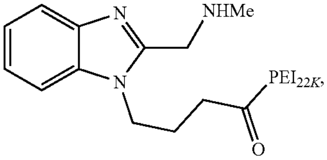
1.25
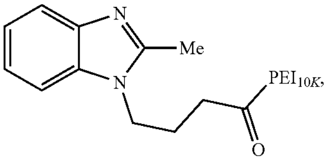

-continued
1.27
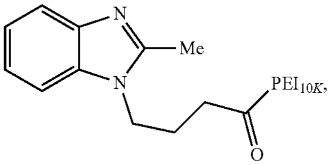
1.28
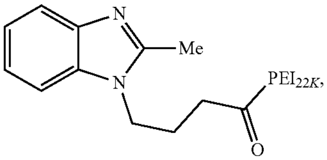
1.30
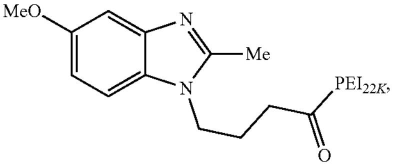
1.35
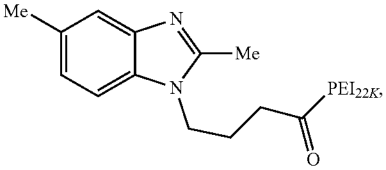
1.36
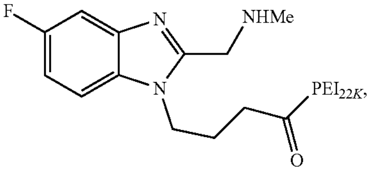
1.37
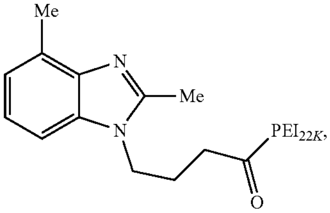
1.41
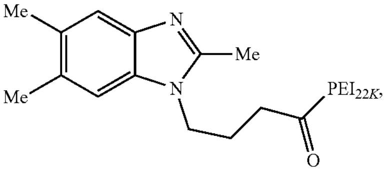
1.42
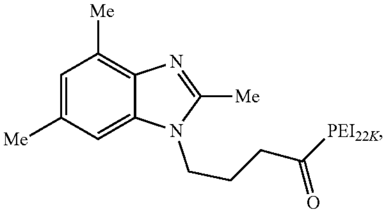
-continued
1.57
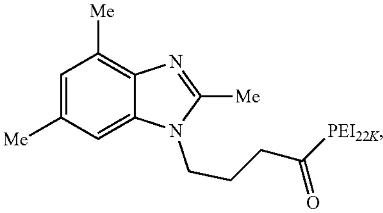
1.60
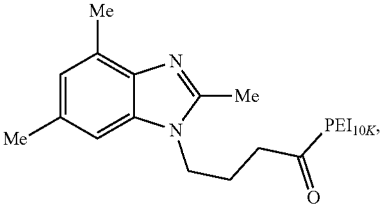
1.65
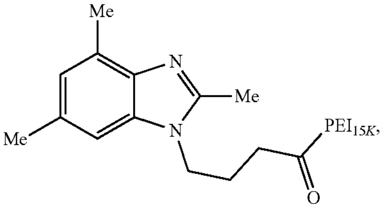
2.03
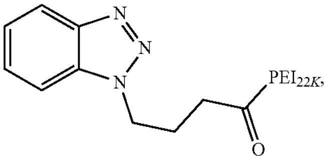
2.04
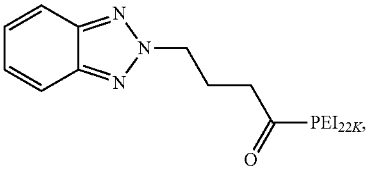
2.05
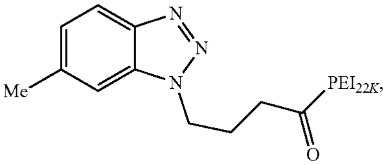
2.08
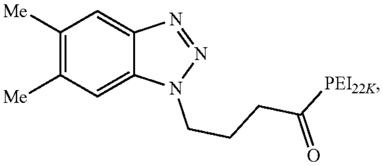
2.09
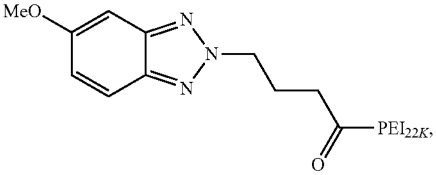
and -continued

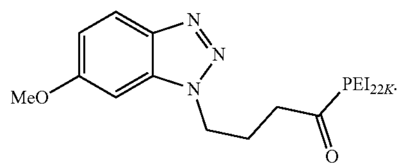

2.10

18. The composition according to claim 17, wherein the at least one compound of general formula (II) is compound 1.42, 1.57 or 1.65.

19. A method for in vitro or ex vivo transfection of live cells comprising introducing in the cells the composition according to claim 2.

20. A method for in vitro or ex vivo transfection of at least one nucleic acid molecule into a cell, cell line or cells, the method comprising introducing the composition of claim 2 into the cell, the cell line, or the cells.

21. The method of claim 20, wherein the method is performed to transfect at least one nucleic acid molecule, into a stem cell, said composition comprising (i) the compound 1.42, and (ii) an acceptable excipient, buffering agent, cell culture medium, or transfection medium.

22. The method of claim 20, wherein the method is performed to transfect at least one nucleic acid molecule, into a neuronal cell, said composition comprising (i) the compound 1.65 or the compound 1.60, and (ii) an acceptable excipient, buffering agent, cell culture medium, or transfection medium.

23. A method for genome engineering, for cell reprogramming, for differentiating cells, or for gene-editing, comprising applying to the genome, cells, or gene the composition according to claim 2.

24. A method for the production of:

(i) biologics encoding a recombinant protein, peptide or antibody, the method comprising applying to the cell the composition of claim 2; or (ii) recombinant virus, the method comprising applying to the cell the composition of claim 2, said composition comprising multiple nucleic acid molecules for co-transfection; or (iii) viral or virus-like particles, the method comprising applying to the cell the composition according to claim 2, said composition comprising multiple nucleic acid molecules for co-transfection.

25. The method according to claim 24, for the production of AAV or LV, said composition comprising (i) at least the compound 1.42, and (ii) an acceptable excipient, buffering agent, cell culture medium, or transfection medium.

26. The method according to claim 24, for the production of LV, said composition comprising (i) at least the compound 1.57, and (ii) an acceptable excipient, buffering agent, cell culture medium, or transfection medium.

27. The method according to claim 24, for the production of recombinant virus, said composition comprising a plurality of plasmid vectors to transfect in an adherent or suspension cell, wherein said plasmid vectors are constructs expressing viral structural sequences and transfer vector genome for virus or virus-like production and optionally expressing molecules of interest encoded by the transfer vector genome.

28. A method for performing cell therapy or gene therapy, comprising administering in vivo to a host the recombinant virus produced by the method of claim 27.

29. The composition according to claim 1, wherein the cell is a eukaryotic cell.

30. The composition according to claim 2, wherein the at least one nucleic acid molecule is selected from the group consisting of a deoxyribonucleic acid (DNA), a ribonucleic acid (RNA), a DNA/RNA hybrid and an expression vector encoding said nucleic acid molecule.

31. The composition according to claim 30, wherein the at least one nucleic acid molecule is an RNA selected from the group consisting of a short interfering RNA (siRNA), a microRNA (miRNA), a short hairpin RNA (shRNA), a messenger RNA (mRNA) and a CRISPR guide RNA.

32. The composition according to claim 30, wherein the expression vector encoding said nucleic acid molecule is a plasmid encoding said nucleic acid molecule or a plasmid expressing said nucleic acid molecule.

33. The composition according to claim 5, wherein the graft cationic polymer has a grafting ratio ranging from 5 to 30%.

34. The composition according to claim 33, wherein the graft cationic polymer has a grafting ratio of 20%.

35. The composition according to claim 6, wherein the graft cationic polymer has an average Mw of 6, 8, 10, 15, 22 or 30 kDa.

36. The composition according to claim 10, wherein one of $Z^4$, $Z^5$ represents $CH_3$.

37. The composition according to claim 11, wherein $Z^4$ and $Z^6$ represent $CH_3$.

38. The composition according to claim 12, wherein $Z^5$ and $Z^6$ represent $CH_3$.

39. The composition according to claim 13, wherein $Z^2$, $Z^4$ and $Z^6$ represent $CH_3$.

40. The method according to claim 20, wherein the cell, cell line or cells are selected from the group consisting of a mammalian cell, an insect cell, a primary cell, an adherent cell, a suspension cell, a dividing cell, a non-dividing cell, and a cancer cell, said cell, cell line or cells being optionally organized into spheroids, organoids, 2D or 3D cell culture, or provided as fibre or matrix culture, and/or within a bioreactor.

41. The method according to claim 24, wherein the recombinant virus is selected from the group consisting of an adeno-associated virus (AAV), a lentivirus (LV), an adenovirus, an oncolytic virus, and a baculovirus.

* * * * *